United States Patent
Urch et al.

(10) Patent No.: US 11,224,224 B2
(45) Date of Patent: Jan. 18, 2022

(54) THIOBENZOIMIDAZOLE AS FUNGICIDES

(71) Applicant: REDAG CROP PROTECTION LTD, Wigan (GB)

(72) Inventors: Christopher John Urch, Cheshire (GB); Roger John Butlin, Cheshire (GB); Stephania Christou, Cheshire (GB); Rebecca Kathryn Booth, Cheshire (GB)

(73) Assignee: REDAG CROP PROTECTION LTD., Wigan (GB)

( * ) Notice: Subject to any disclaimer, the term of this patent is extended or adjusted under 35 U.S.C. 154(b) by 0 days.

(21) Appl. No.: 16/473,071

(22) PCT Filed: Jan. 12, 2018

(86) PCT No.: PCT/GB2018/050077
§ 371 (c)(1),
(2) Date: Jun. 24, 2019

(87) PCT Pub. No.: WO2018/130838
PCT Pub. Date: Jul. 19, 2018

(65) Prior Publication Data
US 2020/0085053 A1 Mar. 19, 2020

(30) Foreign Application Priority Data
Jan. 13, 2017 (GB) .................................. 1700587

(51) Int. Cl.
| | |
|---|---|
| *A01N 43/713* | (2006.01) |
| *A01N 43/52* | (2006.01) |
| *A01N 43/54* | (2006.01) |
| *A01N 43/56* | (2006.01) |
| *A01N 43/80* | (2006.01) |
| *C07D 401/14* | (2006.01) |
| *C07D 403/04* | (2006.01) |
| *C07D 403/14* | (2006.01) |
| *C07D 413/14* | (2006.01) |
| *C07D 417/14* | (2006.01) |

(52) U.S. Cl.
CPC .......... *A01N 43/713* (2013.01); *A01N 43/52* (2013.01); *A01N 43/54* (2013.01); *A01N 43/56* (2013.01); *A01N 43/80* (2013.01); *C07D 401/14* (2013.01); *C07D 403/04* (2013.01); *C07D 403/14* (2013.01); *C07D 413/14* (2013.01); *C07D 417/14* (2013.01)

(58) Field of Classification Search
CPC ...... A01N 43/713; A01N 43/52; A01N 43/54; A01N 43/56; A01N 43/80; A01N 43/60; A01N 43/78; A01N 43/82; A01N 47/18; A01N 53/00; C07D 401/14; C07D 403/04; C07D 403/14; C07D 413/14; C07D 417/14; C07D 403/12; A61P 31/10
See application file for complete search history.

(56) References Cited

FOREIGN PATENT DOCUMENTS

| | | |
|---|---|---|
| EP | 1810677 A1 | 7/2007 |
| JP | 11021225 A | 1/1999 |
| WO | 2000043394 A1 | 7/2000 |
| WO | 2004047769 A2 | 6/2004 |
| WO | 2012136581 A1 | 10/2012 |
| WO | 2016055802 A1 | 4/2016 |
| WO | 2017178819 A1 | 10/2017 |

OTHER PUBLICATIONS

CAPLUS Registry Nos. 1976742-57-0, 1972441-96-5 and 1967558-21-9 [Database Registry Chemical Abstracts Service, Columbus, Ohio, Accession No. , Entered STN Aug. 21, 2016, Aug. 12, 2016, and Aug. 5, 2016, 1.p.*
Dighe, N.S., Design, synthesis, antimicrobial and anti-inflammatory activities of some N-{3-[2-(substituted sulfanyl)-1H-benzimidazol-1-yl]-4H-(substituted)}-1,2,4-triazole and 2-(substituted sulfanyl)-1-[5-substituted-1,3,International Journal of Pharma and Biosciences 2013 4(4):484-496.*
International Search Report and the Written Opinion for International Application No. PCT/GB2018/050077, dated Apr. 17, 2018, 15 pages.
Ahbachane, et al., Comptes Rendus de l'Academie des Sciences, Serie Ile: Chimie, vol. 3(4), 2000, (Ahabchane, Noureddine Hamou et al), "Synthesis of 2-pyrazolinyl-, isoxazolinyl-, 1,2,3-triazolyl-, and 1,3,4-oxadiazolylmethylthio-1-pyrazolylbenzimidazoles", pp. 313-319, ISSN: 1387-1609 see Chem. Abs. Acc. No. 2000:646407.
International Search Report issued in corresponding International Patent Application No. GB1700587.7, dated Nov. 27, 2017, 16 pages.
Dighe, N.S; et al, "Design, Synthesis, Antimicrobial and Anti-Inflammatory Activities of Some N-{3-[2-(Substituted Sulfanyl)-1H-Enzimidazol-1-yl]-4H(Substituted)}-1,2,4-Triazole and 2-(Substituted Sulfanyl)-1-[5-Substituted-1,3,4-Oxadiazol-2-yl]-1H-Benzimidazole Deriviatives", International Journal of Pharma and Bio Sciences, 2013m vol. 4(4), pp. 484-496.
Yu-Bin Bai, et al., "Synthesis and Antifungal Activity of 2-Chloromethyl-1H-benzimidazole Derivatives against Phytopathogenic Fungi in Vitro," dx.doi.org/10.1021/jf3053934, J. Agric. Food Chem. 2013, 61, 2789-2795.

(Continued)

*Primary Examiner* — John M Mauro
(74) *Attorney, Agent, or Firm* — Morgan, Lewis & Bockius LLP

(57) ABSTRACT

The present invention relates to 2-thiobenzimidazoles of formula (I) which are of use as fungicides.

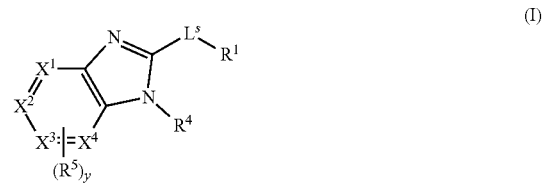

21 Claims, No Drawings

(56) References Cited

OTHER PUBLICATIONS

Examination Report for Australian Patent Application No. 2018207337 dated Jan. 20, 2021, 10 pages.
Examination Report for Indian Patent Application No. 201917027232 dated Feb. 11, 2021, 6 pages.

* cited by examiner

THIOBENZOIMIDAZOLE AS FUNGICIDES

This application is the U.S. national stage application of International (PCT) Patent Application Serial No. PCT/GB2018/050077, filed Jan. 12, 2018, which claims the benefit of GB Application No. 1700587.7, filed Jan. 13, 2017. The entire disclosure of each of these applications is hereby incorporated by reference.

The present invention relates to 2-thiobenzimidazoles and related compounds which are of use in the field of agriculture as fungicides.

Given the global increase in demand for food, there is an international need for new treatments to reduce food crop losses to disease, insects and weeds. Over 40% of crops are lost before harvest, and 10% post harvest, worldwide. Losses have actually increased since the mid-1990s.

A new threat contributing to this is the emergence of chemical-resistant organisms, for example, glyphosate-resistant weeds in USA and strobilurin-resistant strains of septoria fungal species.

Recent research also suggests that the geographical spread of many crop pests and diseases is increasing, possibly as a result of global warming.

WO2012/136581, WO2016/055802 and WO2017/178819 provide a range of tetrazole containing compounds that have proved active as fungicides.

An aim of certain embodiments of the present invention is to provide pesticides (e.g. fungicides) which have activity either non-selectively, i.e. broad spectrum activity, or which are active specifically against selective target organisms.

An aim of certain embodiments of the present invention is to provide compounds which are less persistent in the environment after use than prior art compounds. Alternatively or additionally, the compounds of the present invention may be less prone to bioaccumulation once in the food chain than prior art compounds.

Another aim of certain embodiments of the invention is to provide compounds which are less harmful to humans than prior art compounds.

Alternatively or additionally, the compounds of the invention may be less harmful than prior art compounds to one or more of the following groups: amphibians, fish, mammals (including domesticated animals such as dogs, cats, cows, sheep, pigs, goats, etc.), reptiles, birds, and beneficial invertebrates (e.g. bees and other insects, or worms), beneficial nematodes, beneficial fungi and nitrogen-fixing bacteria.

Certain compounds of the invention may be as active or more active than prior art compounds. They may have activity against organisms which have developed a resistance to prior art compounds. However, certain embodiments of the present invention may also concern compounds which have a lower level of activity relative to prior art compounds. These lower activity compounds are still effective as fungicides but may have other advantages relative to existing compounds such as, for example, a reduced environmental impact.

Certain compounds of the invention may be more selective than prior art compounds, i.e. they may have better, similar or even slightly lower activity than prior art compounds against target species but have a significantly lower activity against non-target species (e.g. the crops which are being protected).

Certain embodiments of the invention provide compounds that achieve one or more of the above aims. The compounds may be active in their own right or may metabolise or react in aqueous media to yield an active compound.

SUMMARY OF THE INVENTION

In a first aspect of the invention is provided a compound of formula (I):

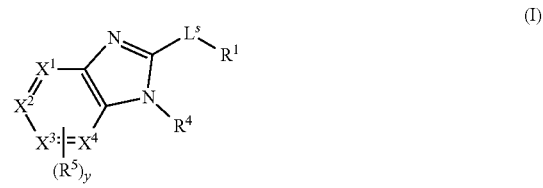

wherein $-L^s-$ is independently $-(CR^2R^3)_n-S-C(R^2R^3)_n-$;

wherein $X^1$, $X^2$, $X^3$ and $X^4$ are each selected from carbon and nitrogen; wherein no more than three of $X^1$, $X^2$, $X^3$ and $X^4$ are nitrogen;

$R^1$ is independently selected from $C(O)OR^6$, $C(O)NR^7R^8$, 5-, 6-, 9- or 10-membered heteroaryl group, wherein said heteroaryl group is optionally substituted with a single $R^9$ group and/or from 1 to 5 $R^{10}$ groups;

$R^2$ and $R^3$ are each independently selected from H, F, $C_1$-$C_4$-alkyl and $C_1$-$C_4$-haloalkyl;

or $R^2$ and $R^3$ together with the carbon to which they are attached form a $C_3$-$C_5$-cycloalkyl group;

$R^4$ is independently selected from 5- or 6-membered heteroaryl, optionally further substituted with from 1 to 4 $R^{11}$ groups;

$R^5$, $R^{10}$ and $R^{11}$ are each independently at each occurrence selected from: halo, nitro, cyano, $NR^{12}R^{13}$, $NR^{12}S(O)_2R^{12}$, $NR^{12}C(O)R^{12}$, $NR^{12}CONR^{12}R^{12}$, $NR^{12}CO_2R^{12}$, $OR^{12a}$, $SR^{12}$, $S(O)R^{12}$, $OS(O)_2R^{12}$, $S(O)_2R^{12}$, $S(O)_2NR^{12}R^{12}$, $CO_2R^{12}$, $C(O)R^{12}$, $CONR^{12}R^{12}$, $C_1$-$C_6$-alkyl, $C_2$-$C_6$-alkenyl, $C_2$-$C_6$-alkynyl, $C_1$-$C_6$-haloalkyl, phenyl, $C_3$-$C_6$-cycloalkyl, $_{3-6}$-heterocycloalkyl, 5- or 6-membered heteroaryl, and $-O-C_1$-$C_4$-haloalkyl;

$R^6$ and $R^7$ are each independently selected from H, $C_1$-$C_6$-alkyl, $C_1$-$C_6$-haloalkyl, $C_3$-$C_6$-alkenyl, $C_3$-$C_6$-alkynyl, and $C_0$-$C_3$-alkylene-$R^{14}$; wherein $R^{14}$ is independently selected from: $C_3$-$C_6$-cycloalkyl, 4- to 7-membered heterocycloalkyl, phenyl, 5- or 6-membered heteroaryl and $-O-C_1$-$C_4$-alkyl;

$R^8$, $R^{12}$, $R^{15}$, $R^{18}$ and $R^{22}$ are each independently at each occurrence selected from H, $C_1$-$C_6$-alkyl and $C_3$-$C_6$-cycloalkyl;

or $R^7$ and $R^8$ together with the nitrogen to which they are attached form a 4- to 7-membered heterocycloalkyl ring;

or where two $R^{12}$ groups are attached to the same nitrogen atom, the two $R^{12}$ groups together with the nitrogen atom to which they are attached may form a 4- to 7-membered heterocycloalkyl ring;

$R^9$ is $NR^{15}R^{16}$;

$R^{12a}$ is independently at each occurrence selected from H, $C_1$-$C_6$-alkyl, $C_1$-$C_6$-haloalkyl, and $C_3$-$C_6$-cycloalkyl;

$R^{13}$ is independently at each occurrence selected from H, $C_3$-$C_6$-cycloalkyl, $C_1$-$C_6$-alkyl, $C(O)-C_1$-$C_6$-alkyl, $C(O)O-C_1$-$C_6$-alkyl and $S(O)_2-C_1$-$C_6$-alkyl;

or $R^{13}$ and $R^{12}$ together with the carbon to which they are attached form a 4 to 7-membered heterocycloalkyl ring;

$R^{16}$ is independently selected from: H, $C_1$-$C_6$-alkyl, $C_3$-$C_7$-cycloalkyl, $C_1$-$C_4$-alkylene-$R^{16a}$, 4 to 7-membered heterocycloalkyl, 5-, 6-, 9 or 10-membered heteroaryl, C(S)-$L^1$-$R^{17}$ and C(O)-$L^1$-$R^{17}$;

$R^{16a}$ is independently selected from: $C_3$-$C_6$-cycloalkyl, 4- to 7-membered heterocycloalkyl, phenyl, 5- or 6-membered heteroaryl, —O—$C_0$-$C_3$-alkylene-$C_3$-$C_6$-cycloalkyl and —O—$C_1$-$C_4$-alkyl;

-$L^1$- is absent or is independently selected from —O—, —S—, and —$NR^{18}$—;

$R^{17}$ is independently selected from $C_1$-$C_8$-alkyl, $C_1$-$C_8$-haloalkyl, $C_3$-$C_8$-alkenyl, $C_3$-$C_8$-alkynyl, $C_0$-$C_3$-alkylene-$R^{19}$; and —$CR^{20}R^{20}L^2R^{21}$;

-$L^2$- is independently selected from —O—, —S— and —$NR^{22}$—;

$R^{20}$ is independently at each occurrence selected from F, H and $C_1$-$C_4$-alkyl;

$R^{21}$ is independently selected from H, $C_1$-$C_8$-alkyl, $C_1$-$C_8$-haloalkyl, $C_2$-$C_8$-alkenyl, $C_2$-$C_8$-alkynyl and $C_0$-$C_3$-alkylene-$R^{23}$;

$R^{19}$ and $R^{23}$ are each independently at each occurrence selected from $C_3$-$C_6$-cycloalkyl, $_{3-6}$-heterocycloalkyl, 5- or 6-membered heteroaryl and phenyl;

y is an integer selected from 0, 1, 2, 3 and 4;

n is independently at each occurrence an integer selected from 0, 1 and 2;

wherein where any $R^1$-$R^{23}$ group is or forms part of an alkyl, alkenyl, alkynyl, haloalkyl, cycloalkyl, heterocycloalkyl, phenyl or heteroaryl group, that alkyl, haloalkyl, cycloalkyl, heterocycloalkyl, phenyl or heteroaryl group is optionally substituted, where chemically possible, by 1 to 5 substituents which are each independently selected at each occurrence from: oxo, =$NR^a$, =$NOR^a$, halo, nitro, cyano, $NR^aR^b$, $NR^aS(O)_2R^a$, $NR^aC(O)R^a$, $NR^aCONR^aR^a$, $NR^aCO_2R^a$, $OR^a$, $SR^a$, $S(O)R^a$, $S(O)_2R^a$, $S(O)_2NR^aR^a$, $CO_2R^aC(O)R^a$, $CONR^aR^a$, $C_1$-$C_4$-alkyl, $C_2$-$C_4$-alkenyl, $C_2$-$C_4$-alkynyl and $C_1$-$C_4$-haloalkyl; wherein $R^a$ is independently at each occurrence selected from H and $C_1$-$C_4$ alkyl; and $R^b$ is independently at each occurrence selected from H, $C_3$-$C_6$-cycloalkyl, $C_1$-$C_4$-alkyl, C(O)—$C_1$-$C_4$-alkyl and $S(O)_2$—$C_1$-$C_4$-alkyl;

or an agronomically acceptable salt or N-oxide thereof.

In an embodiment, the compound of formula (I) is a compound of formula (Ia):

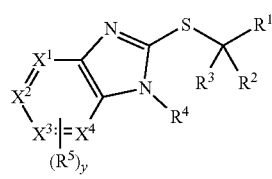

(Ia)

wherein $X^1$, $X^2$, $X^3$, $X^4$, $R^1$, $R^2$, $R^3$, $R^4$, $R^5$ and y are as described above for compounds of formula (I).

In an embodiment, the compound of formula (I) is a compound of formula (II):

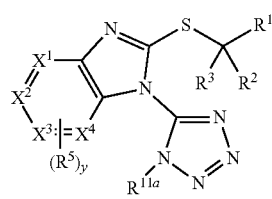

(II)

wherein $X^1$, $X^2$, $X^3$, $X^4$, $R^1$, $R^2$, $R^3$, $R^5$ and y are as described above for compounds of formula (I); and wherein $R^{11a}$ is independently selected from: H, $C_1$-$C_4$-alkyl, $C_3$-$C_4$-alkenyl, $C_3$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl. $R^{11a}$ may be selected from $C_1$-$C_4$-alkyl, $C_1$-$C_4$-haloalkyl and $C_3$-$C_6$-cycloalkyl.

In an embodiment, the compound of formula (I) is a compound of formula (III):

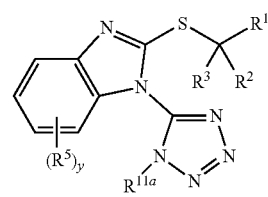

(III)

wherein $R^1$, $R^2$, $R^3$, $R^5$ and y are as described above for compounds of formula (I); and wherein $R^{11a}$ is independently selected from: H, $C_1$-$C_4$-alkyl, $C_3$-$C_4$-alkenyl, $C_3$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl. $R^{11a}$ may be selected from $C_1$-$C_4$-alkyl, $C_1$-$C_4$-haloalkyl and $C_3$-$C_6$-cycloalkyl.

In an embodiment, the compound of formula I is a compound of formula (IV):

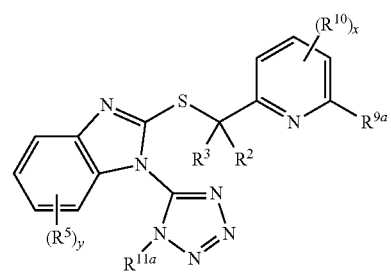

(IV)

wherein $R^2$, $R^3$, $R^5$, $R^{10}$ and y are as described above for compounds of formula (I); and wherein $R^{9a}$ is either absent or is $NR^{15}R^{16}$; and wherein $R^{11a}$ is independently selected from: H, $C_1$-$C_4$-alkyl, $C_3$-$C_4$-alkenyl, $C_3$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl; and x is an integer independently selected from 0, 1, 2, 3 and 4. $R^{11a}$ may be selected from $C_1$-$C_4$-alkyl, $C_3$-$C_4$-alkenyl, $C_3$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl.

In an embodiment, the compound of formula (I) is a compound of formula (V):

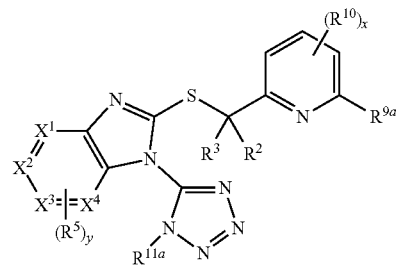

(V)

wherein $X^1$, $X^2$, $X^3$, $X^4$, $R^2$, $R^3$, $R^5$, $R^{10}$ and y are as described above for compounds of formula (I); and wherein $R^{9a}$ is either absent or is $NR^{15}R^{16}$; and wherein $R^{11a}$ is independently selected from: H, $C_1$-$C_4$-alkyl, $C_3$-$C_4$-alkenyl, $C_3$-$C_4$-alkynyl, phenyl, $C_3$-$C_6$-cycloalkyl, $_{3\text{-}6}$-heterocycloalkyl, 5- or 6-membered heteroaryl and $C_1$-$C_4$-haloalkyl; and x is an integer independently selected from 0, 1, 2, 3 and 4. $R^{11a}$ may be selected from $C_1$-$C_4$-alkyl, $C_3$-$C_4$-alkenyl, $C_3$-$C_4$-alkynyl, phenyl, $C_3$-$C_6$-cycloalkyl, $_{3\text{-}6}$-heterocycloalkyl, 5- or 6-membered heteroaryl and $C_1$-$C_4$-haloalkyl.

In an embodiment, the compound of formula (I) is a compound of formula (VI):

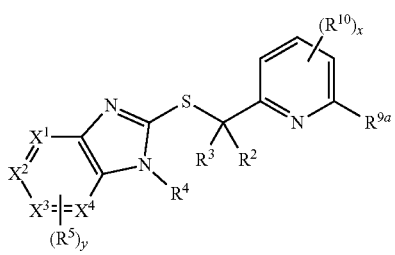

(VI)

wherein $X^1$, $X^2$, $X^3$, $X^4$, $R^2$, $R^3$, $R^4$, $R^5$, $R^{10}$ and y are as described above for compounds of formula (I); and wherein $R^{9a}$ is either absent or is $NR^{15}R^{16}$; and x is an integer independently selected from 0, 1, 2, 3 and 4.

In an embodiment, the compound of formula (I) is a compound of formula (VII):

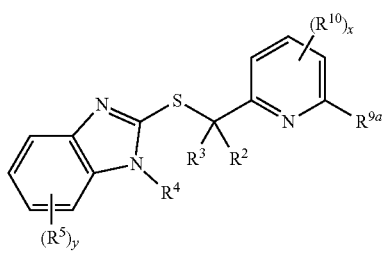

(VII)

wherein $R^2$, $R^3$, $R^4$, $R^5$, $R^{10}$ and y are as described above for compounds of formula (I); wherein $R^{9a}$ is either absent or is $NR^{15}R^{16}$; and wherein x is an integer independently selected from 0, 1, 2, 3 and 4.

In an embodiment, the compound of formula (I) is a compound of formula (VIII):

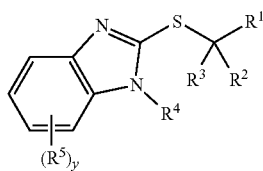

(VIII)

wherein $R^1$, $R^2$, $R^3$, $R^4$, $R^5$ and y are as described above for compounds of formula (I).

In an embodiment, the compound of formula I is a compound of formula (IX):

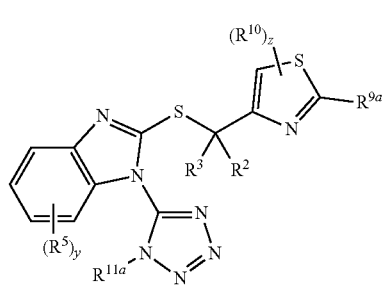

(IX)

wherein $R^2$, $R^3$, $R^5$, $R^{10}$ and y are as described above for compounds of formula (I); and wherein $R^{9a}$ is either absent or is $NR^{15}R^{16}$; and wherein $R^{11a}$ is independently selected from: H, $C_1$-$C_4$-alkyl, $C_3$-$C_4$-alkenyl, $C_3$-$C_4$-alkynyl, phenyl, $C_3$-$C_6$-cycloalkyl, $_{3\text{-}6}$-heterocycloalkyl, 5- or 6-membered heteroaryl and $C_1$-$C_4$-haloalkyl; and z is an integer independently selected from 0, 1 and 2. $R^{11a}$ may be selected from $C_1$-$C_4$-alkyl, $C_3$-$C_4$-alkenyl, $C_3$-$C_4$-alkynyl, phenyl, $C_3$-$C_6$-cycloalkyl, $_{3\text{-}6}$-heterocycloalkyl, 5- or 6-membered heteroaryl and $C_1$-$C_4$-haloalkyl.

In an embodiment, the compound of formula (I) is a compound of formula (X):

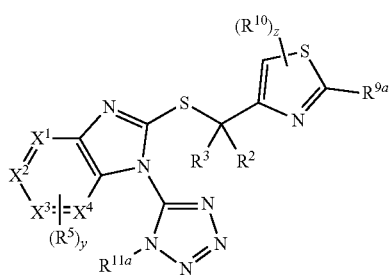

(X)

wherein $X^1$, $X^2$, $X^3$, $X^4$, $R^2$, $R^3$, $R^5$, $R^{10}$ and y are as described above for compounds of formula (I); and wherein $R^{9a}$ is either absent or is $NR^{15}R^{16}$; and wherein $R^{11a}$ is independently selected from: H, $C_1$-$C_4$-alkyl, $C_3$-$C_4$-alkenyl, $C_3$-$C_4$-alkynyl, phenyl, $C_3$-$C_6$-cycloalkyl, $_{3\text{-}6}$-heterocycloalkyl, 5- or 6-membered heteroaryl and $C_1$-$C_4$-haloalkyl; and z is an integer independently selected from 0, 1 and 2. $R^{11a}$ may be selected from $C_1$-$C_4$-alkyl, $C_3$-$C_4$-alkenyl, $C_3$-$C_4$-alkynyl, phenyl, $C_3$-$C_6$-cycloalkyl, $_{3\text{-}6}$-heterocycloalkyl, 5- or 6-membered heteroaryl and $C_1$-$C_4$-haloalkyl.

In an embodiment, the compound of formula (I) is a compound of formula (XI):

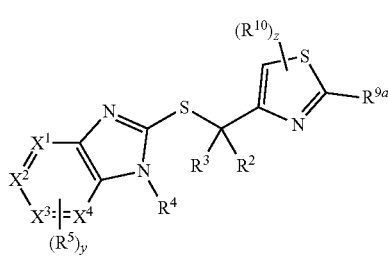

(XI)

wherein $X^1$, $X^2$, $X^3$, $X^4$, $R^2$, $R^3$, $R^4$, $R^5$, $R^{10}$ and y are as described above for compounds of formula (I); and wherein $R^{9a}$ is either absent or is $NR^{15}R^{16}$; and z is an integer independently selected from 0, 1 and 2.

In an embodiment, the compound of formula (I) is a compound of formula (XII):

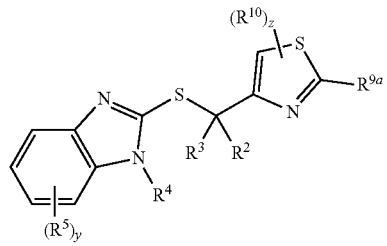

(XII)

wherein $R^2$, $R^3$, $R^4$, $R^5$, $R^{10}$ and y are as described above for compounds of formula (I); wherein $R^{9a}$ is either absent or is $NR^{15}R^{16}$; and wherein z is an integer independently selected from 0, 1 and 2.

For the absence of doubt, where $R^{9a}$ is absent, the carbon to which $R^{9a}$ is shown as being attached may be substituted with an $R^{10}$ group. Thus, in certain formulae above, where $R^{9a}$ is absent, it is chemically possible for x to be 4. Likewise, in certain formulae above, where $R^{9a}$ is absent, it is chemically possible for z to be 2.

The following embodiments apply to compounds of any of formulae (I)-(XII). These embodiments are independent and interchangeable. Any one embodiment may be combined with any other embodiment, where chemically allowed. In other words, any of the features described in the following embodiments may (where chemically allowable) be combined with the features described in one or more other embodiments. In particular, where a compound is exemplified or illustrated in this specification, any two or more of the embodiments listed below, expressed at any level of generality, which encompass that compound may be combined to provide a further embodiment which forms part of the present disclosure.

$-L^s-$ may be $—S—$. $-L^s-$ may be $—(CR^2R^3)—S—$. $-L^s-$ may be $—S—(CR^2R^3)—$, e.g. $—S—CH_2—$.

$X^1$ may be nitrogen. $X^1$ may be carbon. $X^2$ may be nitrogen. $X^2$ may be carbon. $X^3$ may be nitrogen. $X^3$ may be carbon. $X^4$ may be nitrogen. $X^4$ may be carbon. It may be that no more than two of $X^1$, $X^2$, $X^3$ and $X^4$ are nitrogen. It may be that no more than one of $X^1$, $X^2$, $X^3$ and $X^4$ are nitrogen. It may be that a single one of $X^1$, $X^2$, $X^3$ and $X^4$ is nitrogen. It may be that each of $X^1$, $X^2$, $X^3$ and $X^4$ are carbon.

$R^1$ may be a 5- or 6-membered heteroaryl group. $R^1$ may be a 5- or 6-membered heteroaryl group having a nitrogen atom in the ring neighbouring the carbon through which $R^1$ is connected to the rest of the molecule. Where such an $R^1$ group is substituted with an $R^9$ group, that $R^9$ group may be connected to the $R^1$ group at a carbon atom neighbouring the nitrogen atom that neighbours the carbon through which $R^1$ is connected to the rest of the molecule $R^1$ may be a 6-membered heteroaryl group. Thus, $R^1$ may be selected from pyridine, pyrimidine or pyrazine. $R^1$ may be a 6-membered heteroaryl group having a nitrogen atom in the ring neighbouring the carbon through which $R^1$ is connected to the rest of the molecule. In certain examples, $R^1$ is pyridine. Thus, $R^1$ may be 2-pyridine. $R^1$ may have the structure:

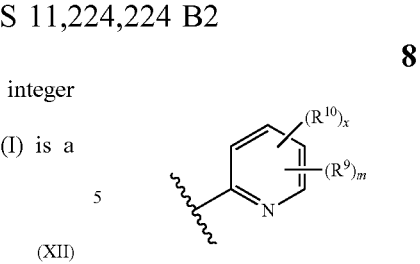

wherein x is an integer selected from 0, 1, 2, 3 and 4 and m is an integer selected from 0 and 1. It may be that m is 1. Thus, $R^1$ may have the structure:

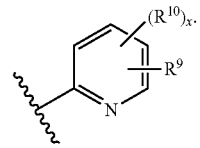

In certain embodiments, $R^1$ has the structure:

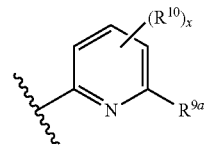

wherein x is an integer selected from 0, 1, 2, 3 and 4; and $R^{9a}$ is either absent or is $NR^{15}R^{16}$.

In certain embodiments, $R^1$ has the structure:

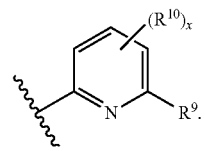

It may be however that $R^1$ is not substituted with $R^9$. Thus, $R^1$ may have the structure:

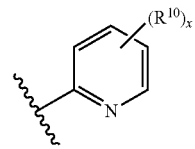

wherein x is an integer selected from 0, 1, 2, 3 and 4.

In certain embodiments, $R^1$ has the structure:

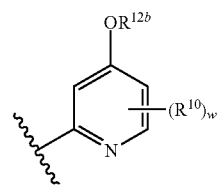

wherein $R^{12b}$ is independently selected from H, $C_1$-$C_6$-alkyl, $C_1$-$C_6$-haloalkyl, and $C_3$-$C_6$-cycloalkyl; and w is an integer selected from 0, 1, 2 and 3. It may be that $R^{12b}$ is independently selected from $C_1$-$C_6$-alkyl, $C_1$-$C_6$-haloalkyl, and $C_3$-$C_6$-cycloalkyl. It may be that $R^{12b}$ is independently selected from $C_1$-$C_6$-alkyl and $C_1$-$C_6$-haloalkyl.

w may be an integer from 0 to 2. w may be an integer from 1 to 3, e.g. from 1 to 2. w may be 1.

$R^{10}$ may be independently at each occurrence selected from halo, nitro, cyano, $NR^{12}R^{13}$, $NR^{12}S(O)_2R^{12}$, $NR^{12}C(O)R^{12}$, $NR^{12}CONR^{12}R^{12}$, $NR^{12}CO_2R^{12}$, $OR^{12a}$, $SR^{12}$, $S(O)R^{12}$, $S(O)_2R^{12}$, $OS(O)_2OR^{12}$, $S(O)_2NR_{12}R_{12}$, $CO_2R^{12}$, $C(O)R^{12}$, $CONR^{12}R^{12}$, $C_1$-$C_4$-alkyl, $C_3$-$C_4$-alkenyl, $C_3$-$C_4$-alkynyl, and $C_1$-$C_4$-haloalkyl. $R^{10}$ may be independently at each occurrence selected from halo, cyano, $C_1$-$C_4$-alkyl, O—$C_1$-$C_4$-alkyl and $C_1$-$C_4$-haloalkyl. $R^{10}$ may be independently at each occurrence selected from: halo, cyano, $C_1$-$C_4$-alkyl, $C_3$-$C_4$-alkenyl, $C_3$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl.

x may be an integer from 0 to 2. x may be an integer from 1 to 3, e.g. from 1 to 2. x may be 1. x may be 0. Thus, $R^1$ may be

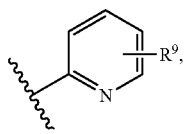

e.g.

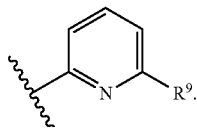

Alternatively, $R^1$ may be a 5-membered heteroaryl group. Thus, $R^1$ may be selected from oxazole, imidazole or thiazole. $R^1$ may be selected from oxazole and thiazole. In certain preferred examples, $R^1$ is thiazole. $R^1$ may be a 5-membered heteroaryl group having a nitrogen atom in the ring neighbouring the carbon through which $R^1$ is connected to the rest of the molecule. Thus, $R^1$ may be 4-thiazole or 4-oxazole. $R^1$ may be 4-thiazole. $R^1$ may be

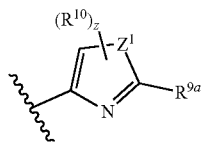

wherein $Z^1$ is independently selected from O and S; $R^{9a}$ is either absent or is $NR^{15}R^{16}$; and wherein z is an integer independently selected from 0, 1 and 2. $Z^1$ may be O. $Z^1$ may be S.

$R^1$ may be

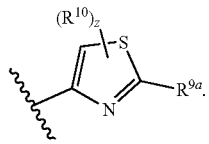

$R^1$ may be

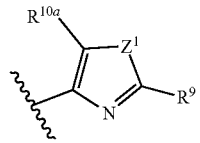

wherein $Z^1$ is independently selected from O and S; $R^{10a}$ is independently selected from: H, halo, nitro, cyano, $NR^{12}R^{13}$, $NR^{12}S(O)_2R^{12}$, $NR^{12}C(O)R^{12}$, $NR^{12}CONR^{12}R^{12}$, $NR^{12}CO_2R^{12}$, $OR^{12a}$, $SR^{12}$, $S(O)R^{12}$, $OS(O)_2R^{12}$, $S(O)_2R^{12}$, $S(O)_2NR^{12}R^{12}$, $CO_2R^{12}$, $C(O)R^{12}$, $CONR^{12}R^{12}$, $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl. $R^1$ may be

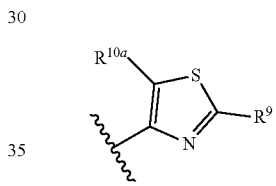

$R^{10a}$ may be independently selected from H, halo, nitro, cyano, $NR^{12}R^{13}$, $NR^{12}S(O)_2R^{12}$, $NR^{12}C(O)R^{12}$, $NR^{12}CONR^{12}R^{12}$, $NR^{12}CO_2R^{12}$, $OR^{12a}$, $SR^{12}$, $S(O)R^{12}$, $S(O)_2R^{12}$, $OS(O)_2OR^{12}$, $S(O)_2NR^{12}R^{12}$, $CO_2R^{12}$, $C(O)R^{12}$, $CONR^{12}R^{12}$, $C_1$-$C_4$-alkyl, $C_2$-$C_4$-alkenyl, $C_2$-$C_4$-alkynyl, and $C_1$-$C_4$-haloalkyl. $R^{10a}$ may be independently selected from: H, halo, cyano, $C_1$-$C_4$-alkyl and $C_1$-$C_4$-haloalkyl. $R^{10a}$ may be independently selected from: H, halo, cyano, $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl.

$R^{10a}$ may be $R^{10}$. $R^{10a}$ may thus be independently selected from: halo, nitro, cyano, $NR^{12}R^{13}$, $NR^{12}S(O)_2R^{12}$, $NR^{12}C(O)R^{12}$, $NR^{12}CONR^{12}R^{12}$, $NR^{12}CO_2R^{12}$, $OR^{12a}$, $SR^{12}$, $S(O)R^{12}$, $S(O)_2R^{12}$, $S(O)_2NR^{12}R^{12}$, $CO_2R^{12}$, $C(O)R^{12}$, $CONR^{12}R^{12}$, $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl. $R^{10a}$ may be independently selected from halo, nitro, cyano, $NR^{12}R^{13}$, $NR^{12}S(O)_2R^{12}$, $NR^{12}C(O)R^{12}$, $NR^{12}CONR^{12}R^{12}$, $NR^{12}CO_2R^{12}$, $OR^{12a}$, $SR^{12}$, $S(O)R^{12}$, $S(O)_2R^{12}$, $S(O)_2NR^{12}R^{12}$, $CO_2R^{12}$, $C(O)R^{12}$, $CONR^{12}R^{12}$, $C_1$-$C_4$-alkyl, $C_2$-$C_4$-alkenyl, $C_2$-$C_4$-alkynyl, and $C_1$-$C_4$-haloalkyl. $R^{10a}$ may be independently selected from: halo, cyano, $C_1$-$C_4$-alkyl and $C_1$-$C_4$-haloalkyl. $R^{10a}$ may be independently selected from: halo, cyano, $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl.

$R^{10a}$ may be H. Thus, $R^1$ may be

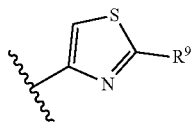

z may be 0.

$R^{9a}$ may be $NR^{15}R^{16}$;

$R^{15}$ may be $C_1$-$C_4$-alkyl, e.g. Me or Et. Preferably, however, $R^{15}$ is H.

$R^{16}$ may be independently selected from: H and $C_1$-$C_6$-alkyl.

$R^{16}$ may be independently selected from: $C_1$-$C_6$-alkyl and $C_1$-$C_4$-alkylene-$R^{16a}$. $R^{16a}$ may be independently selected from: $C_3$-$C_6$-cycloalkyl, phenyl and 5- or 6-membered heteroaryl. $R^{16a}$ may be independently selected from: $C_3$-$C_6$-cycloalkyl and phenyl. $R^{16a}$ may be 5- or 6-membered heteroaryl, e.g. 5- or 6-membered heteroaryl group having at least one nitrogen atom in the ring.

Illustrative $R^9$ groups include:

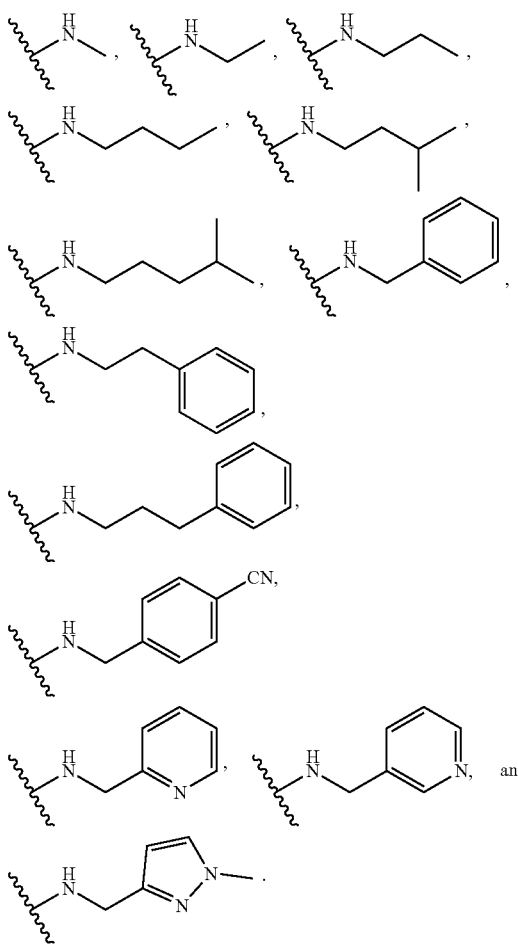

$R^{16}$ may be independently selected from 4 to 7-membered heterocycloalkyl and 5-, 6-, 9 or 10-membered heteroaryl. $R^{16}$ may be independently selected from 4 to 7-membered heterocycloalkyl and 5- or 6-membered heteroaryl.

In certain embodiments, $R^1$ has the structure:

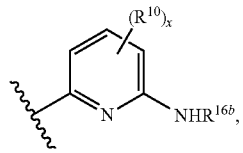

wherein $R^{16b}$ is independently selected from H, $C_1$-$C_6$-alkyl, $C_3$-$C_7$-cycloalkyl, $C_1$-$C_4$-alkylene-$R^{16a}$, 4 to 7-membered heterocycloalkyl, 5-, 6-, 9 or 10-membered heteroaryl. $R^{16b}$ may be independently selected from $C_1$-$C_6$-alkyl, $C_3$-$C_7$-cycloalkyl, $C_1$-$C_4$-alkylene-$R^{16a}$, 4 to 7-membered heterocycloalkyl, 5-, 6-, 9 or 10-membered heteroaryl.

$R^1$ may be

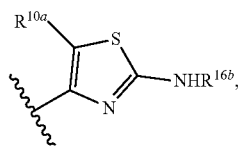

wherein $R^{16b}$ is independently selected from H, $C_1$-$C_6$-alkyl, $C_3$-$C_7$-cycloalkyl, $C_1$-$C_4$-alkylene-$R^{16a}$, 4 to 7-membered heterocycloalkyl, 5-, 6-, 9 or 10-membered heteroaryl. $R^{16b}$ may be independently selected from $C_1$-$C_6$-alkyl, $C_3$-$C_7$-cycloalkyl, $C_1$-$C_4$-alkylene-$R^{16a}$, 4 to 7-membered heterocycloalkyl, 5-, 6-, 9 or 10-membered heteroaryl.

Preferably, $R^{16}$ is selected from $C(S)$-$L^1$-$R^{17}$ and $C(O)$-$L^1$-$R^{17}$. $R^1$ may be $C(O)$-$L^1$-$R^{17}$.

-$L^1$- may be absent. In these embodiments, $R^{17}$ may be independently selected from: $C_1$-$C_8$-alkyl, $C_2$-$C_8$-alkenyl, $C_2$-$C_8$-alkynyl and $C_0$-$C_3$-alkylene-$R^{19}$. $R^{19}$ may be selected from $C_3$-$C_6$-cycloalkyl and phenyl. $R^{19}$ may be phenyl. $R^{19}$ may be $C_3$-$C_6$-cycloalkyl. $R^{17}$ may be independently selected from: $C_1$-$C_8$-alkyl and $C_0$-$C_3$-alkylene-$R^{19}$, where $R^{19}$ is selected from phenyl and $C_3$-$C_6$-cycloalkyl. $R^{17}$ may be independently selected from: $C_1$-$C_8$-alkyl and $C_0$-$C_3$-alkylene-$R^{19}$, where $R^{19}$ is $C_3$-$C_6$-cycloalkyl. Said $R^{17}$ and $R^{19}$ groups may be unsubstituted.

Illustrative $R^9$ groups include:

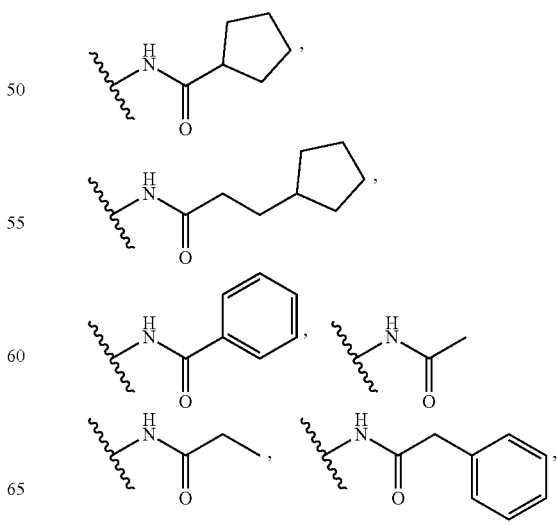

-continued

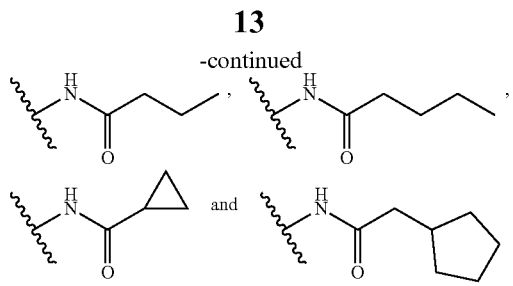

-L$^1$- may be absent. In these embodiments, R$^{17}$ may be independently selected from: $_{3-6}$-heterocycloalkyl, 5- or 6-membered heteroaryl and —CR$^{20}$R$^{20}$L$^2$R$^{21}$. R$^{17}$ may be independently selected from: $_{3-6}$-heterocycloalkyl, 5- or 6-membered heteroaryl. R$^{17}$ may be CR$^{20}$R$^{20}$L$^2$R$^{21}$.

R$^{20}$ is preferably at all occurrences independently selected from F, H and Me. R$^{20}$ may at all occurrences be selected from F and H. R$^{20}$ may at all occurrences be H. R$^{20}$ may at all occurrences be F.

-L$^2$- may be —NR$^{22}$—, e.g. NH. -L$^2$- may be —S—. -L$^2$- may be —O—.

R$^{17}$ may be CR$^{20}$R$^{20}$OR$^{21}$ or CR$^{20}$R$^{20}$SR$^{21}$, where R$^{21}$ is independently selected from C$_1$-C$_8$-alkyl, C$_1$-C$_8$-haloalkyl, C$_2$-C$_8$-alkenyl, C$_2$-C$_8$-alkynyl and C$_0$-C$_3$-alkylene-R$^{23}$ wherein R$^{23}$ is independently at each occurrence selected from C$_3$-C$_6$-cycloalkyl, $_{3-6}$-heterocycloalkyl, 5- or 6-membered heteroaryl and phenyl. R$^{21}$ may be independently selected from: C$_1$-C$_8$-alkyl, C$_2$-C$_8$-alkenyl, C$_2$-C$_8$-alkynyl and C$_0$-C$_3$-alkylene-R$^{23}$. R$^{23}$ may be selected from C$_3$-C$_6$-cycloalkyl and phenyl. R$^{23}$ may be phenyl. R$^{23}$ may be C$_3$-C$_6$-cycloalkyl. R$^{21}$ may be independently selected from: C$_1$-C$_8$-alkyl and C$_0$-C$_3$-alkylene-R$^{23}$, where R$^{23}$ is selected from phenyl and C$_3$-C$_6$-cycloalkyl. Said R$^{21}$ and R$^{23}$ groups may be unsubstituted. R$^{17}$ may be CR$^{21}$R$^{21}$OR$^{23}$, where R$^{23}$ is independently selected from: unsubstituted C$_1$-C$_8$-alkyl, unsubstituted C$_3$-C$_6$-cycloalkyl and unsubstituted phenyl.

Illustrative R$^9$ groups include:

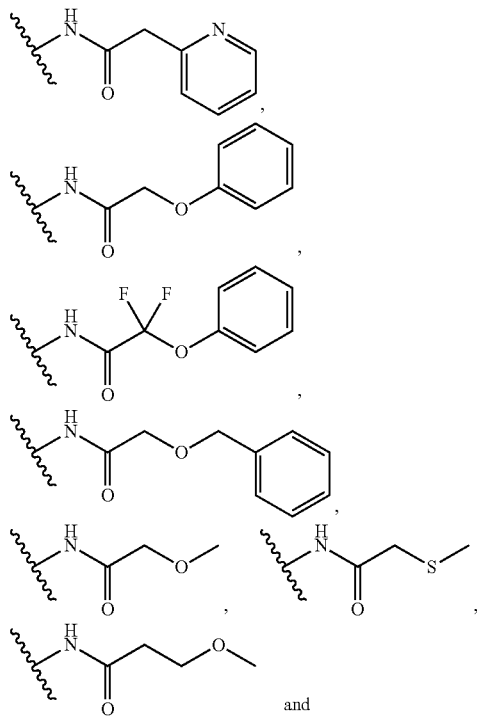

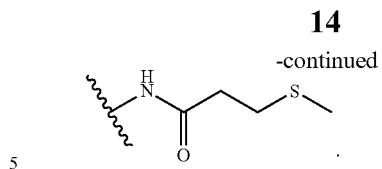

-L$^1$- may be independently selected from: —O—, —S— and —NR$^{18}$—. -L$^1$- may be —O—. In these embodiments, R$^{17}$ may be independently selected from: C$_1$-C$_8$-alkyl, C$_2$-C$_8$-alkenyl, C$_2$-C$_8$-alkynyl and C$_0$-C$_3$-alkylene-R$^{19}$. R$^{19}$ may be selected from C$_3$-C$_6$-cycloalkyl and phenyl. R$^{19}$ may be phenyl. R$^{19}$ may be C$_3$-C$_6$-cycloalkyl. R$^{17}$ may be independently selected from: C$_1$-C$_8$-alkyl and C$_0$-C$_3$-alkylene-R$^{19}$, where R$^{19}$ is selected from phenyl and C$_3$-C$_6$-cycloalkyl. R$^{17}$ may be independently selected from: C$_1$-C$_8$-alkyl and C$_0$-C$_3$-alkylene-R$^{19}$, where R$^{19}$ is C$_3$-C$_6$-cycloalkyl. Said R$^{17}$ and R$^{19}$ groups may be unsubstituted. R$^{17}$ may be C$_1$-C$_8$-alkyl. R$^{17}$ may be C$_3$-C$_8$-alkyl.

Illustrative R$^9$ groups include:

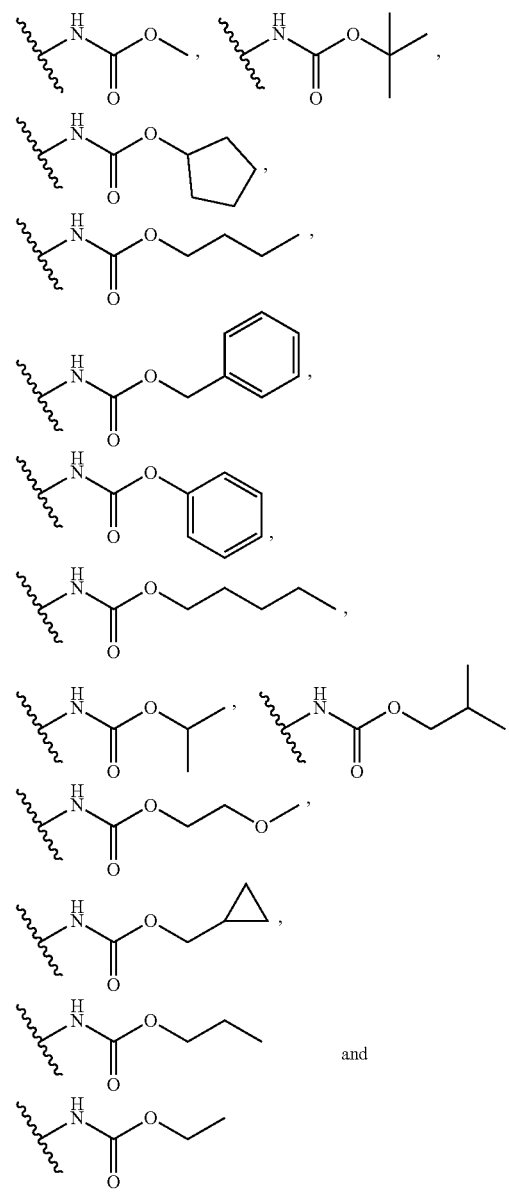

Specific examples of $R^1$ include:
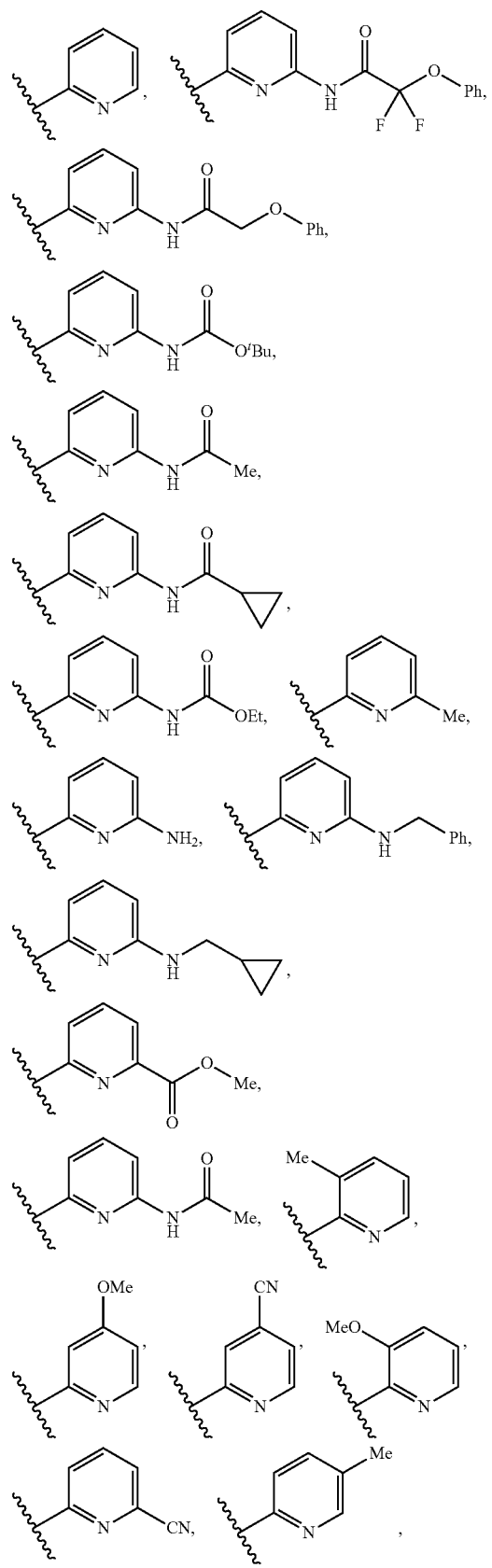
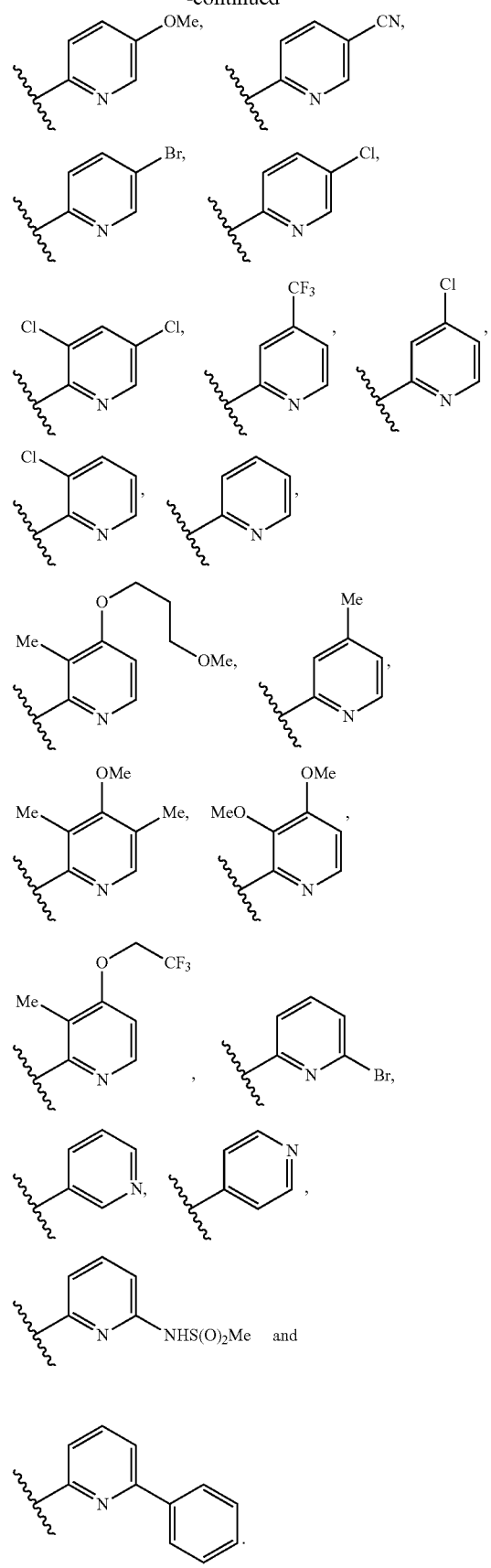

Further specific examples of $R^1$ include:

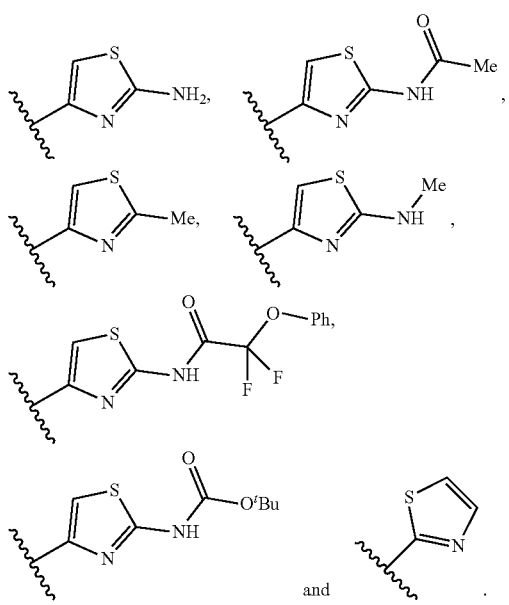

and

It may be that $R^2$ and $R^3$ are each independently selected from H, F, $C_1$-$C_4$-alkyl and $C_1$-$C_4$-haloalkyl. It may be that $R^2$ and $R^3$ are each independently selected from H, F, Me, $CF_3$ and Et. It may be that $R^2$ and $R^3$ are each independently selected from H and Me. It may be that $R^2$ and $R^3$ are each H.

$R^2$ and $R^3$ together with the carbon to which they are attached may form a $C_3$-$C_5$-cycloalkyl group. $R^2$ and $R^3$ together with the carbon to which they are attached may form a cyclopropyl group.

$R^4$ may be a 5- or 6-membered heteroaryl group having 1, 2, 3 or 4 nitrogen atoms in the ring. $R^4$ may be a 5-membered heteroaryl group having 1, 2, 3 or 4 nitrogen atoms in the ring. $R^4$ may be a 6-membered heteroaryl group having 1 or 2 nitrogen atoms in the ring.

$R^4$ may be substituted at a position adjacent to the point of connection of $R^4$ to the rest of the molecule with an $R^{11b}$ group, wherein $R^{11b}$ is selected from $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl. $R^4$ may be substituted at a position adjacent to the point of connection of $R^4$ to the rest of the molecule with an $R^{11b}$ group, wherein $R^{11b}$ is selected from chloro, bromo, $C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl. $R^4$ may be a 5- or 6-membered heteroaryl group having 1, 2, 3 or 4 nitrogen atoms in the ring, said heteroaryl group being substituted at a position adjacent to the point of connection of $R^4$ to the rest of the molecule with an $R^{11b}$ group. $R^4$ may be a 5-membered heteroaryl group having 1, 2, 3 or 4 nitrogen atoms in the ring, said heteroaryl group being substituted at a position adjacent to the point of connection of $R^4$ to the rest of the molecule with an $R^{11b}$ group. $R^4$ may be a 6-membered heteroaryl group having 1 or 2 nitrogen atoms in the ring, said heteroaryl group being substituted at a position ortho to the point of connection of $R^4$ to the rest of the molecule with an $R^{11b}$ group.

$R^4$ may be a tetrazole ring. Said tetrazole ring is substituted with a single $R^{11a}$ group; wherein $R^{11a}$ is independently selected from: $C_1$-$C_4$-alkyl, $C_3$-$C_4$-alkenyl, $C_3$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl. Said tetrazole will typically be attached to the rest of the molecule via the carbon atom of the tetrazole ring. $R^{11a}$ may be attached to a nitrogen atom neighbouring said carbon atom.

Thus, $R^4$ may be:

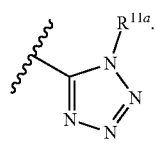

$R^{11a}$ may be selected from $C_1$-$C_4$-alkyl, $C_3$-$C_4$-alkenyl, $C_3$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl. $R^{11a}$ may be selected from $C_1$-$C_4$-alkyl, $C_1$-$C_4$-haloalkyl and $C_3$-$C_6$-cycloalkyl. $R^{11a}$ may be $C_1$-$C_4$-alkyl, e.g. methyl.

Thus, $R^4$ may be:

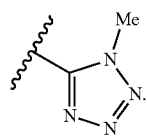 [SMILES: *c1nnnn1C]

$R^4$ may be selected from isoxazole, pyrazole or isothiazole. Thus, $R^4$ may be:

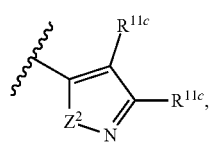

where $Z^2$ is selected from O, S and $NR^{11a}$; wherein $R^{11a}$ is independently selected from: H, $C_1$-$C_4$-alkyl, $C_3$-$C_4$-alkenyl, $C_3$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl; and wherein $R^{11c}$ is selected from H and $R^{11}$. $R^4$ may be:

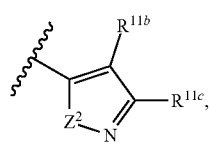

wherein $R^{11b}$ is selected from chloro, bromo, $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl; and wherein $R^{11c}$ is selected from H and $R^{11}$. $Z^2$ may be S. $Z^2$ may be O. $Z^2$ may be $NR^{11a}$.

Alternatively, $R^4$ may be:

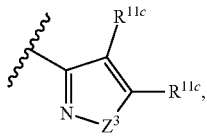

where $Z^3$ is selected from O, S and $NR^{11a}$; wherein $R^{11a}$ is independently selected from: H, $C_1$-$C_4$-alkyl, $C_3$-$C_4$-alkenyl, $C_3$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl; and wherein $R^{11c}$ is selected from H and $R^{11}$. $R^4$ may be:

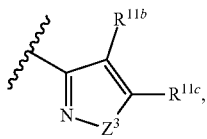

wherein $R^{11b}$ is selected from chloro, bromo, $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl; and wherein $R^{11c}$ is selected from H and $R^{11}$. $Z^3$ may be S. $Z^3$ may be O. $Z^3$ may be $NR^{11a}$.

Illustrative examples of $R^4$ include:

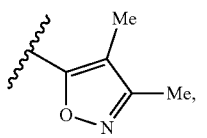 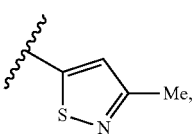

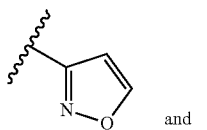 and 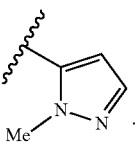

$R^4$ may be a 6-membered heteroaromatic ring. $R^4$ may be a pyridine. $R^4$ may be a 2-pyridine. $R^4$ may be a pyrazine. $R^4$ may be a pyridazine. Thus, $R^4$ may be:

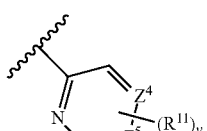

wherein $Z^4$ and $Z^5$ are each independently selected from nitrogen or carbon; and v is an integer from 0 to 4. For the absence of doubt, where $Z^4$ and/or $Z^5$ is carbon, said carbon may be substituted with an $R^{11}$ group.

$R^4$ may be

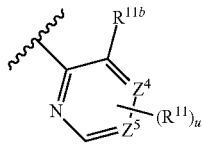

wherein $R^{11b}$ is selected from chloro, bromo, $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl; and wherein u is an integer from 0 to 3.

$Z^4$ may be carbon. $Z^4$ may be N. $Z^5$ may be carbon. $Z^5$ may be N. It may be that a single one of $Z^4$ and $Z^5$ is nitrogen. It may be that $Z^4$ and $Z^5$ are each carbon. It may be that $Z^4$ is carbon and $Z^5$ is nitrogen. It may be that $Z^5$ is carbon and $Z^4$ is nitrogen.

Illustrative examples of $R^4$ include:

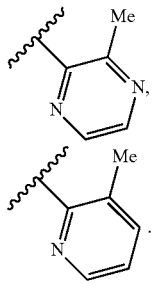 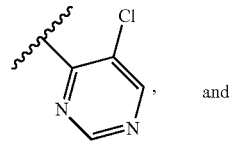 and

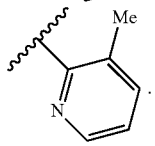

$R^{11a}$ may be independently selected from: H, $C_1$-$C_4$-alkyl, $C_3$-$C_4$-alkenyl and $C_3$-$C_4$-alkynyl. $R^{11a}$ may be independently selected from: H and $C_1$-$C_4$-alkyl. $R^{11a}$ may be independently selected from: $C_1$-$C_4$-alkyl, $C_3$-$C_4$-alkenyl and $C_3$-$C_4$-alkynyl. $R^{11a}$ may be H. $R^{11a}$ may be $C_1$-$C_4$-alkyl, e.g. methyl.

$R^{11b}$ may be selected from chloro, bromo, $C_1$-$C_4$-alkyl, $C_1$-$C_4$-haloalkyl and $C_3$-$C_6$-cycloalkyl. $R^{11b}$ may be selected from $C_1$-$C_4$-alkyl, $C_1$-$C_4$-haloalkyl and $C_3$-$C_6$-cycloalkyl. $R^{11b}$ may be $C_1$-$C_4$-alkyl, e.g. methyl.

$R^{11c}$ may be at all occurrences H.

v may be 1 or 2. u may be 1 or 2. v may be 0. u may be 0.

$R^{11}$ is independently at each occurrence selected from: halo, nitro, cyano, $NR^{12}R^{13}$, $NR^{12}S(O)_2R^{12}$, $NR^{12}C(O)R^{12}$, $NR^{12}CONR^{12}R^{12}$, $NR^{12}CO_2R^{12}$, $OR^{12a}$, $SR^{12}$, $S(O)R^{12}$, $S(O)_2R^{12}$, $S(O)_2NR^{12}R^{12}$, $OS(O)_2OR^{12}$, $CO_2R^{12}$, $C(O)R^{12}$, $CONR^{12}R^{12}$, $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl, $C_1$-$C_4$-haloalkyl and —O—$C_1$-$C_4$-haloalkyl. $R^{11}$ may be independently at each occurrence selected from halo, nitro, cyano, $NR^{12}R^{13}$, $NR^{12}S(O)_2R^{12}$, $NR^{12}C(O)R^{12}$, $NR^{12}CONR^{12}R^{12}$, $NR^{12}CO_2R^{12}$, $OR^{12a}$, $SR^{12}$, $S(O)R^{12}$, $S(O)_2R^{12}$, $S(O)_2NR^{12}R^{12}$, $OS(O)_2OR^{12}$, $CO_2R^{12}$, $C(O)R^{12}$, $CONR^{12}R^{12}$, $C_1$-$C_4$-alkyl, $C_2$-$C_4$-alkenyl, $C_2$-$C_4$-alkynyl, $C_1$-$C_4$-haloalkyl and —O—$C_1$-$C_4$-haloalkyl. $R^{11}$ may be independently at each occurrence selected from halo, cyano, $C_1$-$C_4$-alkyl and $C_1$-$C_4$-haloalkyl. $R^{11}$ may be independently at each occurrence selected from: halo, cyano, $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl.

y may be 0. Alternatively, y may be 1 or 2. $R^5$ may be independently at each occurrence selected from halo, cyano, $C_1$-$C_4$-alkyl and $C_1$-$C_4$-haloalkyl and —O—$C_1$-$C_4$-haloalkyl.

$X^1$ may be $CR^{5a}$, wherein $R^{5a}$ is selected from halo, cyano, nitro, $C_1$-$C_4$-alkyl and $C_1$-$C_4$-haloalkyl, O—$C_1$-$C_4$-alkyl and O—$C_1$-$C_4$-haloalkyl.

Thus,

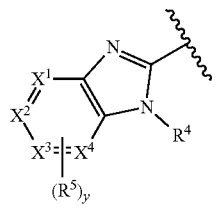

may be

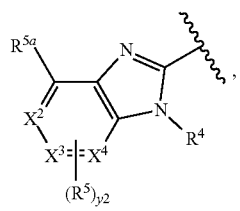

wherein $R^{5a}$ is selected from halo, cyano, nitro, $C_1$-$C_4$-alkyl and $C_1$-$C_4$-haloalkyl, O—$C_1$-$C_4$-alkyl and O—$C_1$-$C_4$-haloalkyl; and y2 is an integer independently selected from 0, 1, 2 and 3.

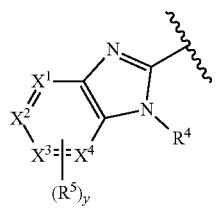

may be

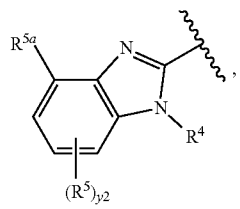

wherein $R^{5a}$ is selected from halo, cyano, nitro, $C_1$-$C_4$-alkyl and $C_1$-$C_4$-haloalkyl, O—$C_1$-$C_4$-alkyl and O—$C_1$-$C_4$-haloalkyl; and y2 is an integer independently selected from 0, 1, 2 and 3.

$R^{5a}$ may be selected from chloro, bromo, $C_1$-$C_4$-alkyl and $C_1$-$C_4$-haloalkyl, O—$C_1$-$C_4$-alkyl and O—$C_1$-$C_4$-haloalkyl. $R^{5a}$ may be chloro or bromo. $R^{5a}$ may be chloro.

$R^5$ may be selected independently at each occurrence from halo, cyano, $C_2$-$C_4$-alkynyl, $C_2$-$C_4$-alkenyl, $C_1$-$C_4$-alkyl and $C_1$-$C_4$-haloalkyl, O—$C_1$-$C_4$-alkyl and O—$C_1$-$C_4$-haloalkyl. $R^5$ may be selected independently at each occurrence from fluoro, chloro, $C_1$-$C_4$-alkyl and $C_1$-$C_4$-haloalkyl, O—$C_1$-$C_4$-alkyl and O—$C_1$-$C_4$-haloalkyl. $R^5$ may be selected independently at each occurrence from fluoro, chloro and O—$C_1$-$C_4$-alkyl.

The compound of formula (I) may be a compound selected from:

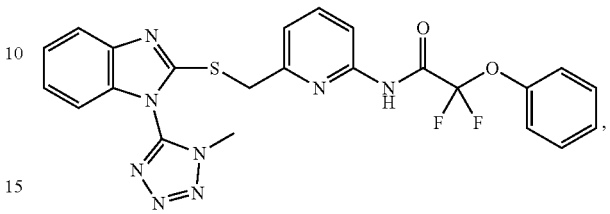

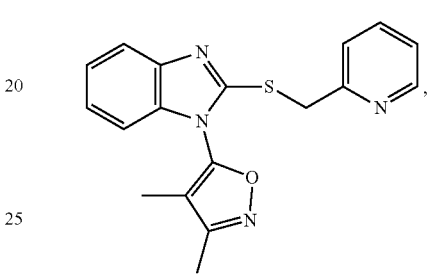

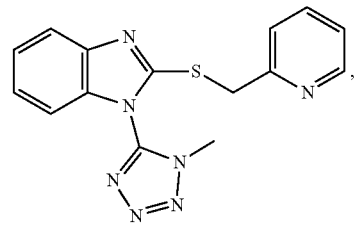

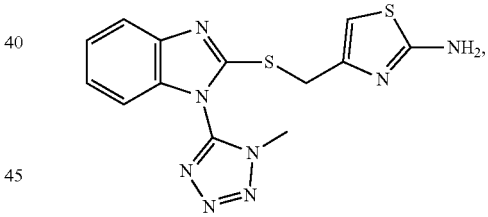

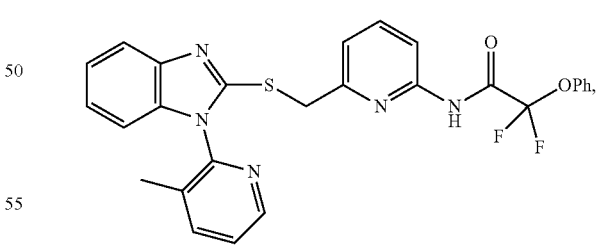

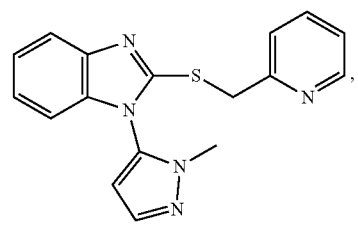

-continued
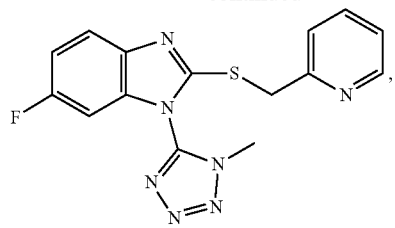
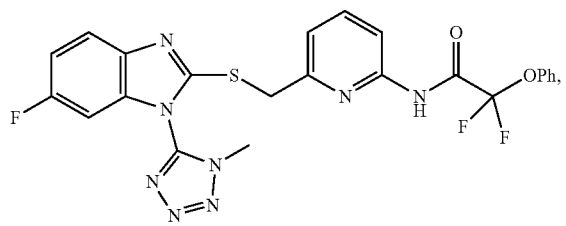
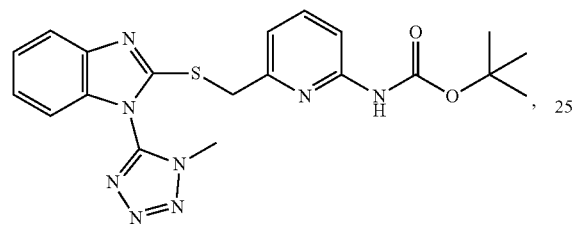
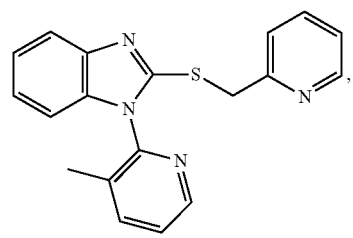
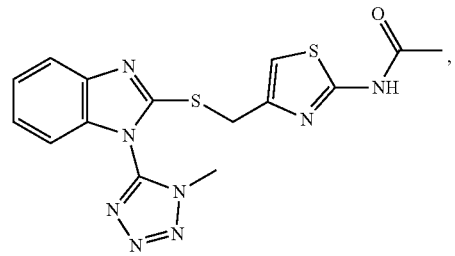
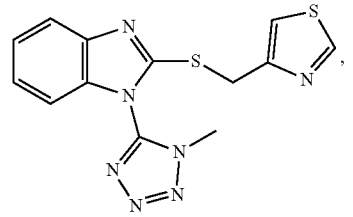
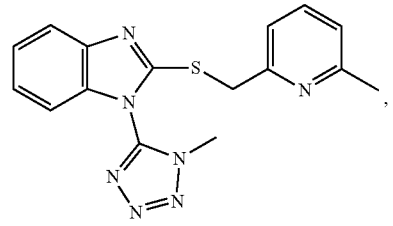
-continued
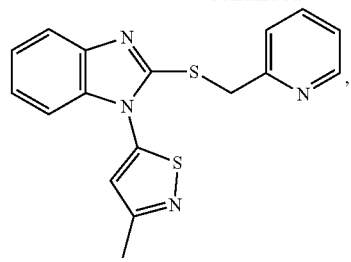
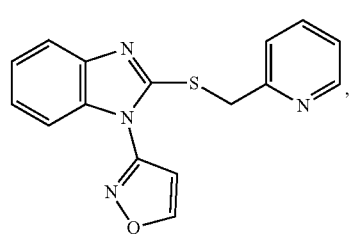
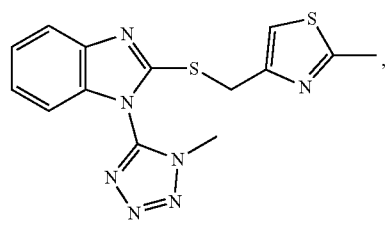
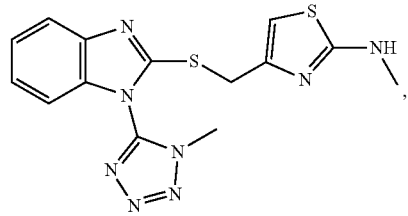
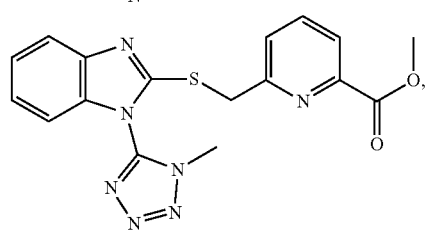
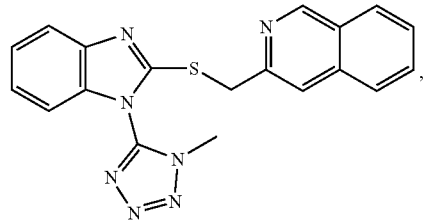
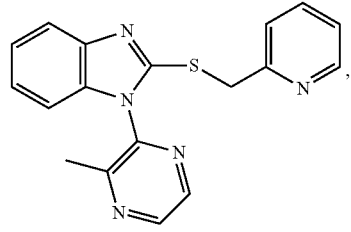

25
-continued
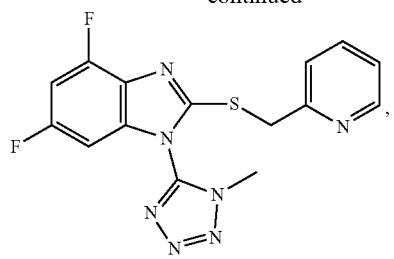
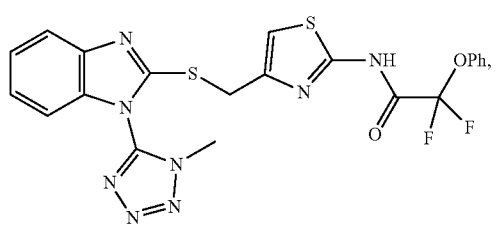
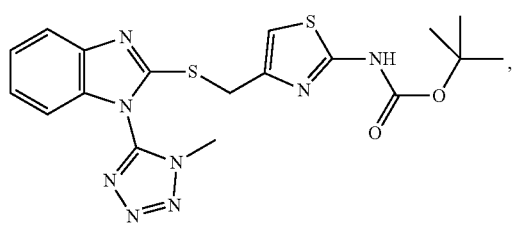
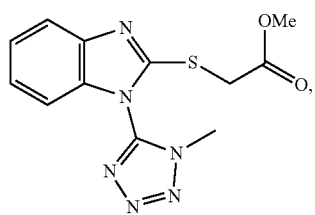
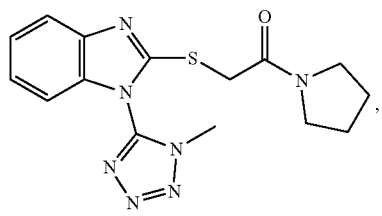
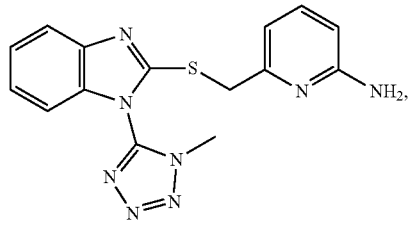
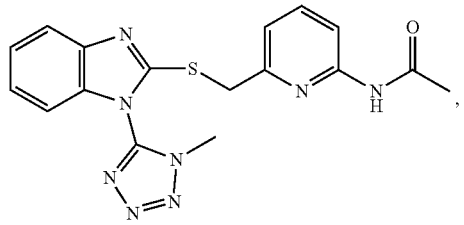
26
-continued
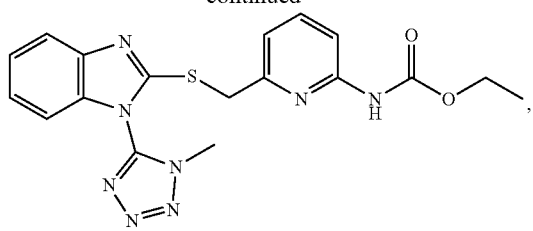
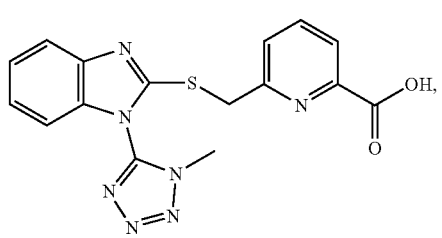
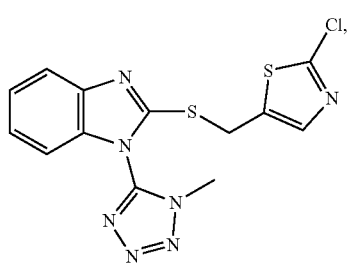
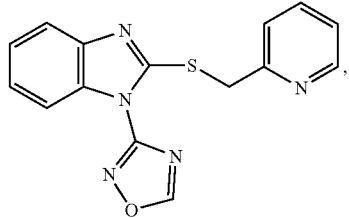
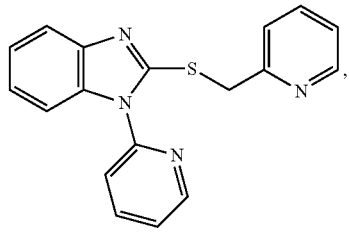
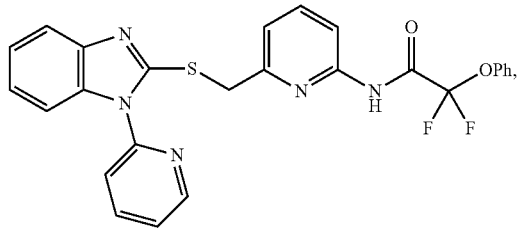
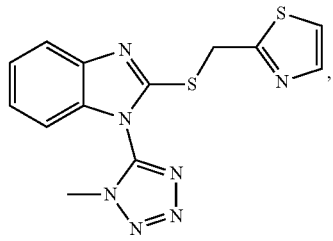

27
-continued
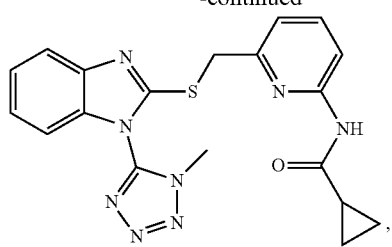
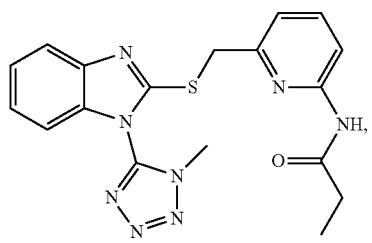
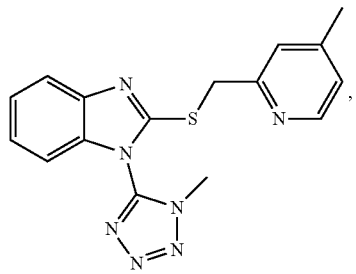
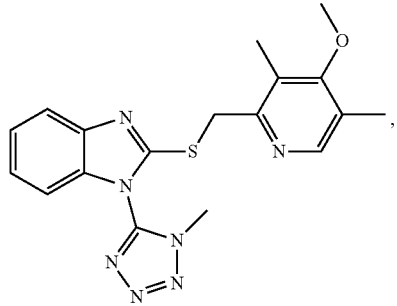
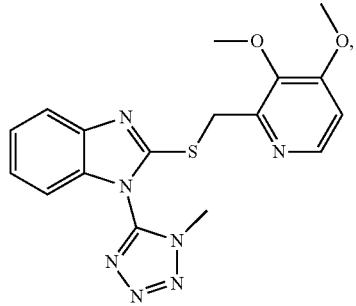
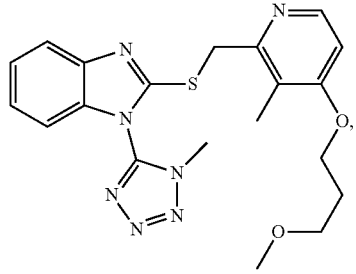
28
-continued
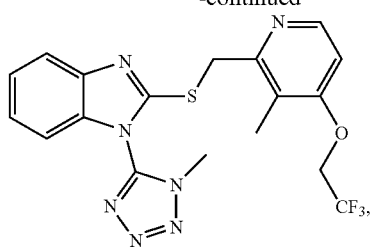
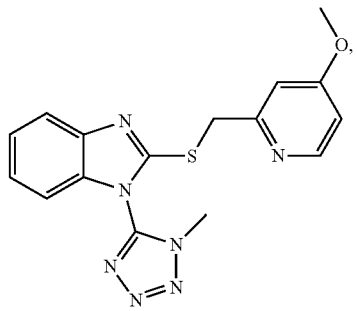
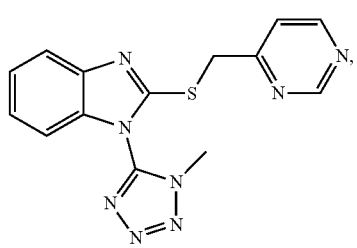
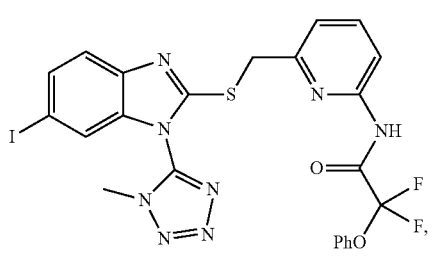
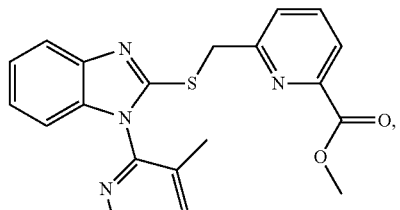
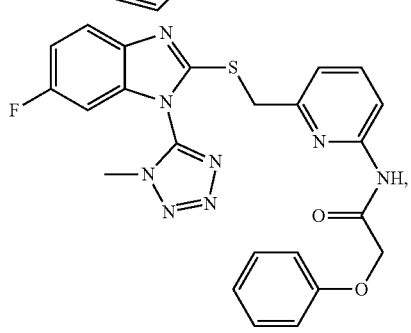

29
-continued
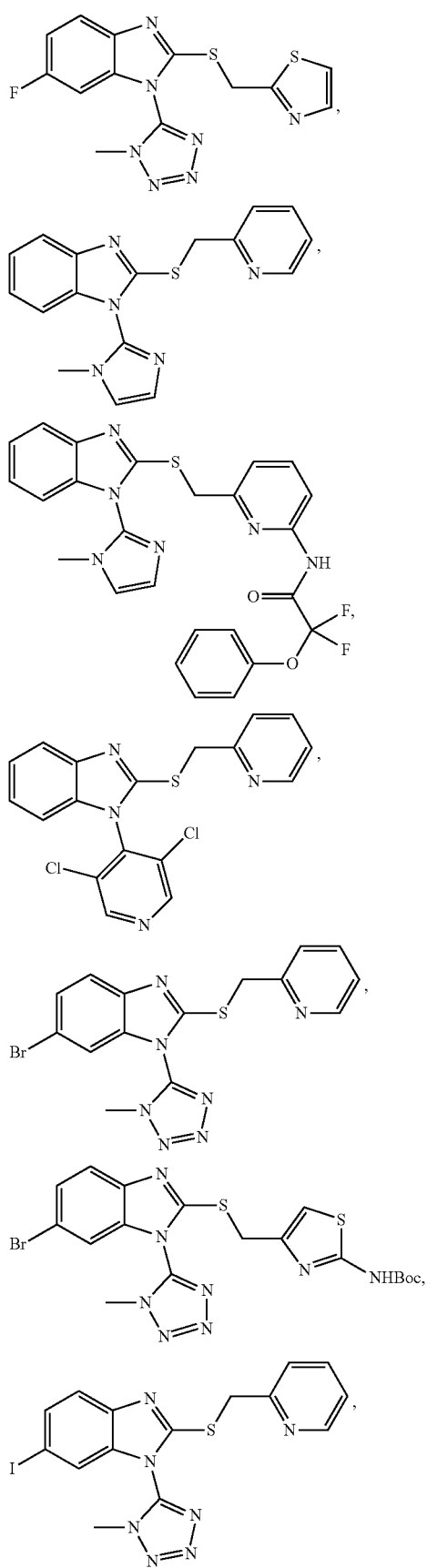
30
-continued
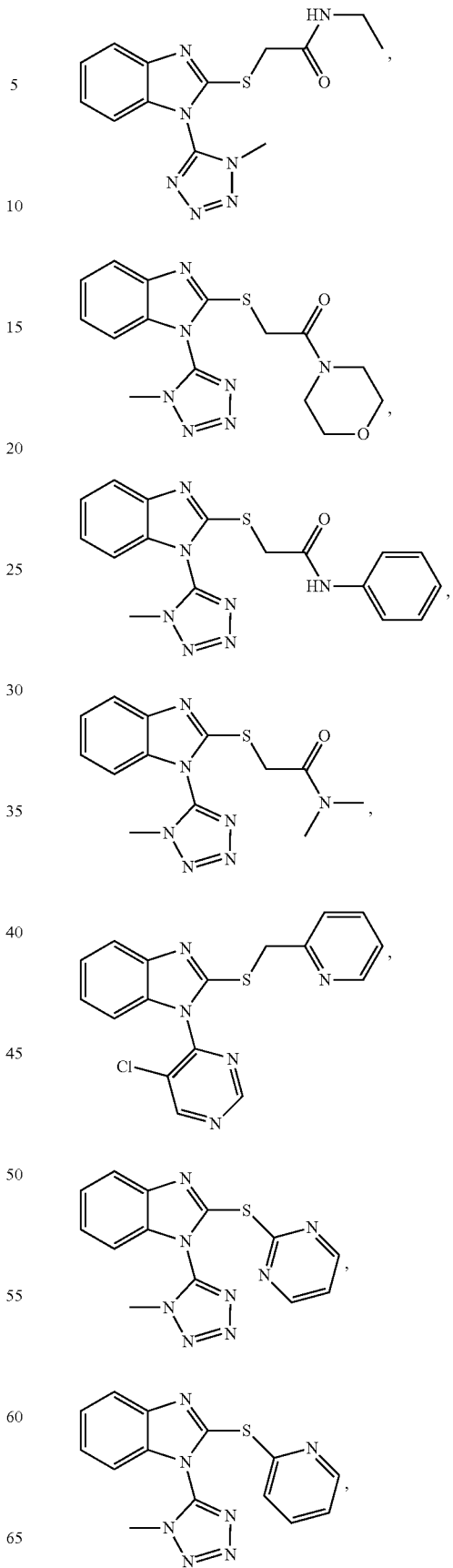

-continued
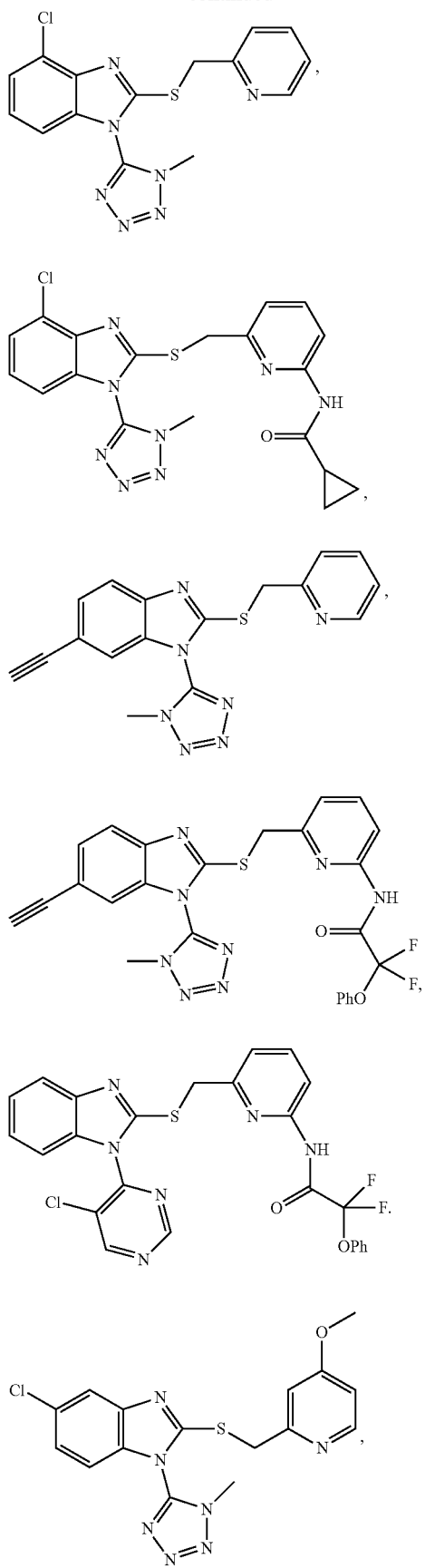
-continued
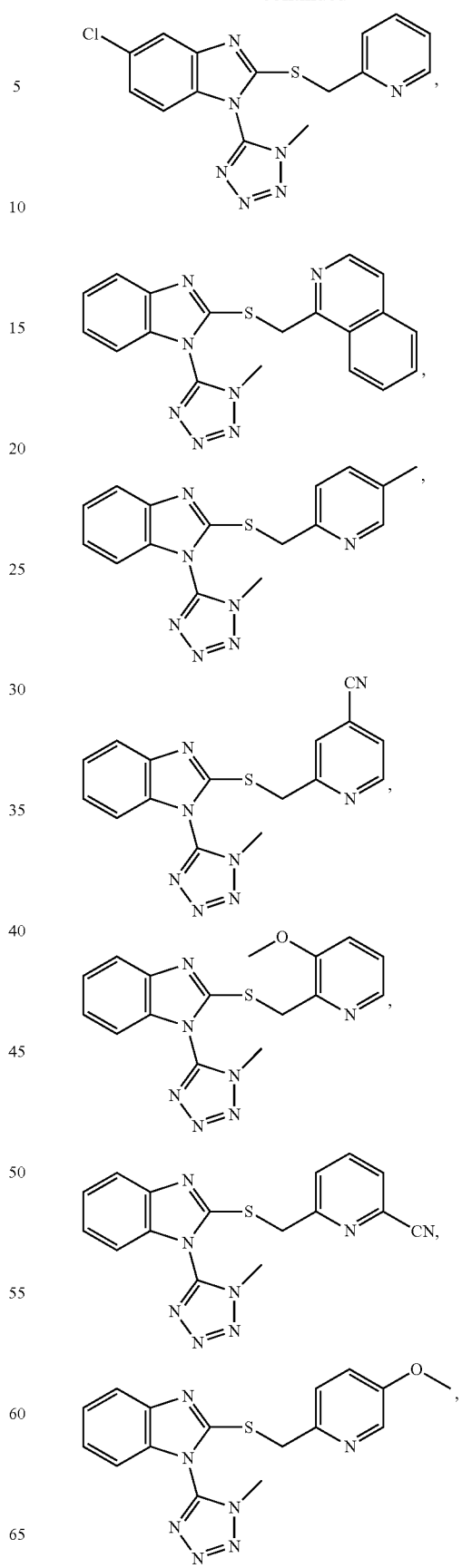

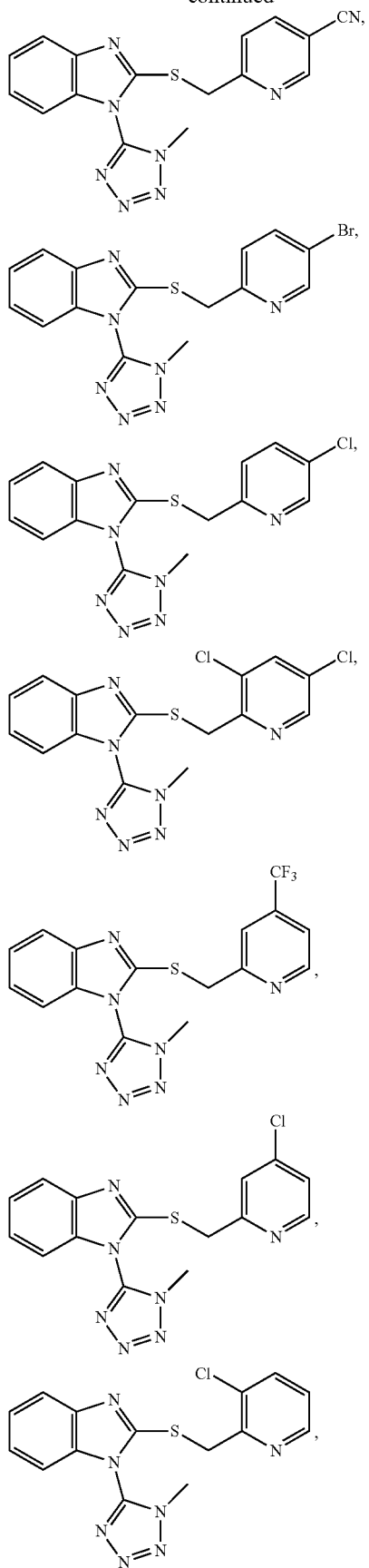
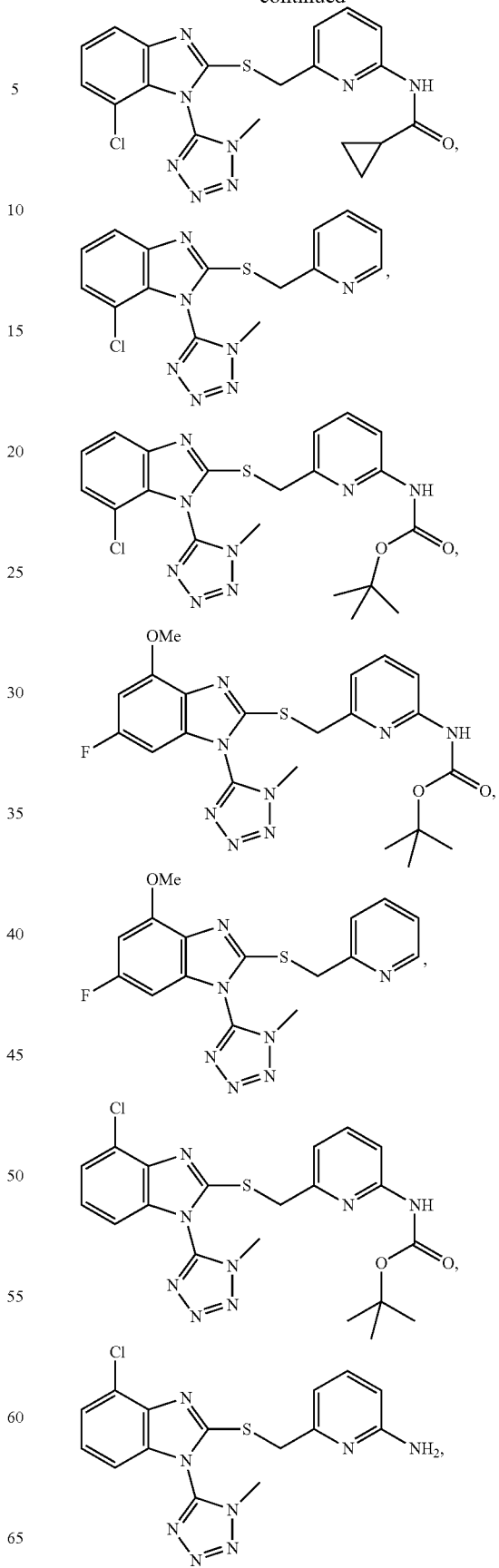

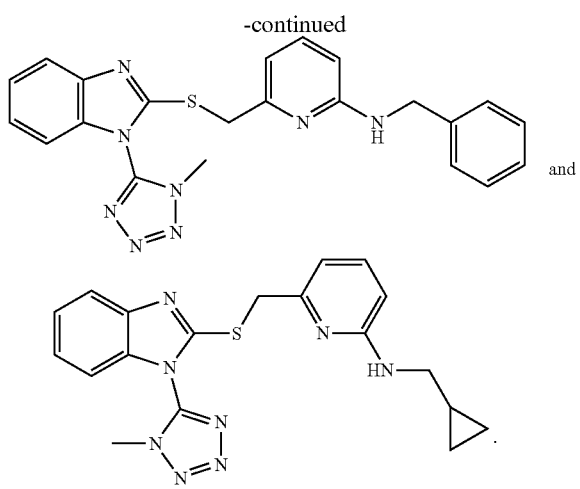

and

The invention may be as described in one of the following numbered paragraphs:

1. A compound of formula (Ib):

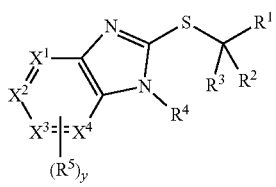

(Ib)

wherein $X^1$, $X^2$, $X^3$ and $X^4$ are each selected from carbon and nitrogen; wherein no more than three of $X^1$, $X^2$, $X^3$ and $X^4$ are nitrogen;

$R^1$ is independently selected from $C(O)OR^6$, $C(O)NR^7R^8$, 5-, 6-, 9- or 10-membered heteroaryl group, wherein said heteroaryl group is optionally substituted with a single $R^9$ group and/or from 1 to 5 $R^{10}$ groups;

$R^2$ and $R^3$ are each independently selected from H, F, $C_1$-$C_4$-alkyl and $C_1$-$C_4$-haloalkyl;

or $R^2$ and $R^3$ together with the carbon to which they are attached form a $C_3$-$C_5$-cycloalkyl group;

$R^4$ is independently selected from 5- or 6-membered heteroaryl, optionally further substituted with from 1 to 4 $R^{11}$ groups;

$R^5$, $R^{10}$ and $R^{11}$ are each independently at each occurrence selected from: halo, nitro, cyano, $NR^{12}R^{13}$, $NR^{12}S(O)_2R^{12}$, $NR^{12}C(O)R^{12}$, $NR^{12}CONR^{12}R^{12}$, $NR^{12}CO_2R^{12}$, $OR^{12}$, $SR^{12}$, $S(O)R^{12}$, $OS(O)_2R^{12}$, $S(O)_2R^{12}$, $S(O)_2NR^{12}R^{12}$, $CO_2R^{12}$, $C(O)R^{12}$, $CONR^{12}R^{12}$, $C_1$-$C_6$-alkyl, $C_2$-$C_6$-alkenyl, $C_2$-$C_6$-alkynyl, $C_1$-$C_6$-haloalkyl, phenyl, $C_3$-$C_6$-cycloalkyl, $_{3-6}$-heterocycloalkyl, 5- or 6-membered heteroaryl, and O—$C_1$-$C_4$-haloalkyl;

$R^6$ and $R^7$ are each independently selected from H, $C_1$-$C_6$-alkyl, $C_1$-$C_6$-haloalkyl, $C_2$-$C_6$-alkenyl, $C_2$-$C_6$-alkynyl, and $C_0$-$C_3$-alkylene-$R^{14}$; wherein $R^{14}$ is independently selected from: $C_3$-$C_6$-cycloalkyl, 4- to 7-membered heterocycloalkyl, phenyl, 5- or 6-membered heteroaryl and —O—$C_1$-$C_4$-alkyl;

$R^8$, $R^{12}$, $R^{15}$, $R^{18}$ and $R^{22}$ are each independently at each occurrence selected from H, $C_1$-$C_6$-alkyl and $C_3$-$C_6$-cycloalkyl;

or $R^7$ and $R^8$ together with the nitrogen to which they are attached form a 4- to 7-membered heterocycloalkyl ring;

or where two $R^{12}$ groups are attached to the same nitrogen atom, the two $R^{12}$ groups together with the nitrogen atom to which they are attached may form a 4- to 7-membered heterocycloalkyl ring;

$R^9$ is $NR^{15}R^{16}$;

$R^{13}$ is independently at each occurrence selected from H, $C_3$-$C_6$-cycloalkyl, $C_1$-$C_6$-alkyl, $C(O)$—$C_1$-$C_6$-alkyl and $S(O)_2$—$C_1$-$C_6$-alkyl;

or $R^{13}$ and $R^{12}$ together with the carbon to which they are attached form a 4 to 7-membered heterocycloalkyl ring;

$R^{16}$ is independently selected from: H, $C_1$-$C_6$-alkyl, 4 to 7-membered heterocycloalkyl, 5-, 6-, 9 or 10-membered heteroaryl, $C(S)$-$L^1$-$R^{17}$ and $C(O)$-$L^1$-$R^{17}$;

-$L^1$- is absent or is independently selected from —O—, —S—, and —$NR^{18}$—;

$R^{17}$ is independently selected from $C_1$-$C_8$-alkyl, $C_1$-$C_8$-haloalkyl, $C_2$-$C_8$-alkenyl, $C_2$-$C_8$-alkynyl, $C_0$-$C_3$-alkylene-$R^{19}$; and —$CR^{20}R^{20}L^2R^{21}$;

-$L^2$- is independently selected from —O—, —S— and —$NR^{22}$—;

$R^{20}$ is independently at each occurrence selected from F, H and $C_1$-$C_4$-alkyl;

$R^{21}$ is independently selected from H, $C_1$-$C_8$-alkyl, $C_1$-$C_8$-haloalkyl, $C_2$-$C_8$-alkenyl, $C_2$-$C_8$-alkynyl and $C_0$-$C_3$-alkylene-$R^{23}$;

$R^{19}$ and $R^{23}$ are each independently at each occurrence selected from $C_3$-$C_6$-cycloalkyl, $_{3-6}$-heterocycloalkyl, 5- or 6-membered heteroaryl and phenyl;

y is an integer selected from 0, 1, 2, 3 and 4;

wherein where any $R^1$-$R^{23}$ group is or forms part of an alkyl, alkenyl, alkynyl, haloalkyl, cycloalkyl, heterocycloalkyl, phenyl or heteroaryl group, that alkyl, haloalkyl, cycloalkyl, heterocycloalkyl, phenyl or heteroaryl group is optionally substituted, where chemically possible, by 1 to 5 substituents which are each independently selected at each occurrence from: oxo, =$NR^a$, =$NOR^a$, halo, nitro, cyano, $NR^aR^b$, $NR^aS(O)_2R^a$, $NR^aC(O)R^a$, $NR^aCONR^aR^a$, $NR^aCO_2R^a$, $OR^a$, $SR^a$, $S(O)R^a$, $S(O)_2R^a$, $S(O)_2NR^aR^a$, $CO_2R^aC(O)R^a$, $CONR^aR^a$, $C_1$-$C_4$-alkyl, $C_2$-$C_4$-alkenyl, $C_2$-$C_4$-alkynyl and $C_1$-$C_4$-haloalkyl; wherein $R^a$ is independently at each occurrence selected from H and $C_1$-$C_4$ alkyl; and $R^b$ is independently at each occurrence selected from H, $C_3$-$C_6$-cycloalkyl, $C_1$-$C_4$-alkyl, $C(O)$—$C_1$-$C_4$-alkyl and $S(O)_2$—$C_1$-$C_4$-alkyl;

or an agronomically acceptable salt or N-oxide thereof.

2. A compound of paragraph 1, wherein each of $X^1$, $X^2$, $X^3$ and $X^4$ are carbon.

3. A compound of paragraph 1, wherein a single one of $X^1$, $X^2$, $X^3$ and $X^4$ is nitrogen.

4. A compound of any one of paragraphs 1 to 3, wherein $R^1$ is a 5- or 6-membered heteroaryl group having a nitrogen atom in the ring neighbouring the carbon through which $R^1$ is connected to the rest of the molecule.

5. A compound of paragraph 4, wherein $R^1$ has the structure:

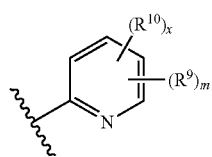

wherein x is an integer selected from 0, 1, 2 and 3; and m is an integer selected from 0 and 1.

6. A compound of paragraph 5, wherein $R^1$ has the structure:

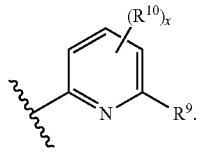

7. A compound of paragraph 4, wherein $R^1$ has the structure

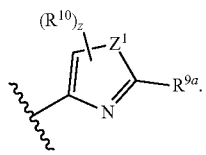

wherein $Z^1$ is independently selected from O and S; $R^{9a}$ is either absent or is $NR^{15}R^{16}$; and wherein z is an integer independently selected from 0, 1 and 2.

8. A compound of paragraph 7, wherein $R^1$ has the structure

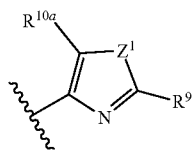

wherein $Z^1$ is independently selected from O and S; $R^{10a}$ is independently selected from: H, halo, nitro, cyano, $NR^{12}R^{13}$, $NR^{12}S(O)_2R^{12}$, $NR^{12}C(O)R^{12}$, $NR^{12}CONR^{12}R^{12}$, $NR^{12}CO_2R^{12}$, $OR^{12}$, $SR^{12}$, $S(O)R^{12}$, $OS(O)_2R^{12}$, $S(O)_2R^{12}$, $S(O)_2NR^{12}R^{12}$, $CO_2R^{12}$, $C(O)R^{12}$, $CONR^{12}R^{12}$, $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl.

9. A compound of paragraph 7 or paragraph 8, wherein $Z^1$ is S.

10. A compound of any one of paragraphs 1 to 9, wherein $R^{16}$ is selected from $C(S)$-$L^1$-$R^{17}$ and $C(O)$-$L^1$-$R^{17}$.

11. A compound of any one of paragraphs 1 to 10, wherein $R^2$ and $R^3$ are each H.

12. A compound of any one of paragraphs 1 to 11, wherein $R^4$ is substituted at a position adjacent to the point of connection of $R^4$ to the rest of the molecule with an $R^{11b}$ group, wherein $R^{11b}$ is selected from $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl.

13. A compound of paragraph 12, wherein $R^4$ has the structure:

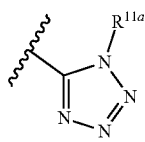

wherein $R^{11a}$ is selected from $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl. $R^{11a}$ may be selected from $C_1$-$C_4$-alkyl, $C_1$-$C_4$-haloalkyl and $C_3$-$C_6$-cycloalkyl.

14. A compound of paragraph 13, wherein $R^{11a}$ is $C_1$-$C_4$-alkyl.

15. A compound of any one of paragraphs 1 to 14, wherein y is 0.

16. A method for controlling fungal diseases, the method comprising applying an agronomically effective and substantially non-phytotoxic quantity of a compound of any one of paragraphs 1 to 15 to seeds of plants, to plants themselves or to an area where it is intended that plants will grow.

17. A use of a compound of any one of paragraphs 1 to 15 to control fungal diseases.

18. A fungicidal composition comprising an effective and non-phytotoxic amount of an active compound of any one of paragraphs 1 to 15.

19. A compound of formula (Ic):

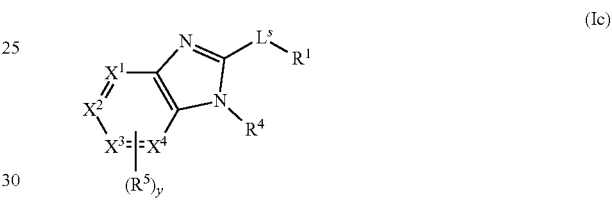

wherein -$L^s$- is independently —$(CR^2R^3)_n$—S—$C(R^2R^3)_n$—;

wherein $X^1$, $X^2$, $X^3$ and $X^4$ are each selected from carbon and nitrogen; wherein no more than three of $X^1$, $X^2$, $X^3$ and $X^4$ are nitrogen;

$R^1$ is independently selected from $C(O)OR^6$, $C(O)NR^7R^8$, 5-, 6-, 9- or 10-membered heteroaryl group, wherein said heteroaryl group is optionally substituted with a single $R^9$ group and/or from 1 to 5 $R^{10}$ groups;

$R^2$ and $R^3$ are each independently selected from H, F, $C_1$-$C_4$-alkyl and $C_1$-$C_4$-haloalkyl;

or $R^2$ and $R^3$ together with the carbon to which they are attached form a $C_3$-$C_5$-cycloalkyl group;

$R^4$ is independently selected from 5- or 6-membered heteroaryl, optionally further substituted with from 1 to 4 $R^{11}$ groups;

$R^5$, $R^{10}$ and $R^{11}$ are each independently at each occurrence selected from: halo, nitro, cyano, $NR^{12}R^{13}$, $NR^{12}S(O)_2R^{12}$, $NR^{12}C(O)R^{12}$, $NR^{12}CONR^{12}R^{12}$, $NR^{12}CO_2R^{12}$, $OR^{12a}$, $SR^{12}$, $S(O)R^{12}$, $OS(O)_2R^{12}$, $S(O)_2R^{12}$, $S(O)_2NR^{12}R^{12}$, $CO_2R^{12}$, $C(O)R^{12}$, $CONR^{12}R^{12}$, $C_1$-$C_6$-alkyl, $C_2$-$C_6$-alkenyl, $C_2$-$C_6$-alkynyl, $C_1$-$C_6$-haloalkyl, phenyl, $C_3$-$C_6$-cycloalkyl, $_{3-6}$-heterocycloalkyl, 5- or 6-membered heteroaryl, and —O—$C_1$-$C_4$-haloalkyl;

$R^6$ and $R^7$ are each independently selected from H, $C_1$-$C_6$-alkyl, $C_2$-$C_6$-alkenyl, $C_2$-$C_6$-alkynyl, and $C_0$-$C_3$-alkylene-$R^{14}$; wherein $R^{14}$ is independently selected from: $C_3$-$C_6$-cycloalkyl, 4- to 7-membered heterocycloalkyl, phenyl, 5- or 6-membered heteroaryl and —O—$C_1$-$C_4$-alkyl;

$R^8$, $R^{12}$, $R^{15}$, $R^{18}$ and $R^{22}$ are each independently at each occurrence selected from H, $C_1$-$C_6$-alkyl and $C_3$-$C_6$-cycloalkyl;

or $R^7$ and $R^8$ together with the nitrogen to which they are attached form a 4- to 7-membered heterocycloalkyl ring;

or where two $R^{12}$ groups are attached to the same nitrogen atom, the two $R^{12}$ groups together with the nitrogen atom to which they are attached may form a 4- to 7-membered heterocycloalkyl ring;

$R^9$ is $NR^{15}R^{16}$;

$R^{12a}$ is independently at each occurrence selected from H, $C_1$-$C_6$-alkyl, $C_1$-$C_6$-haloalkyl, and $C_3$-$C_6$-cycloalkyl;

$R^{13}$ is independently at each occurrence selected from H, $C_3$-$C_6$-cycloalkyl, $C_1$-$C_6$-alkyl, C(O)—$C_1$-$C_6$-alkyl, C(O)O—$C_1$-$C_6$-alkyl and $S(O)_2$—$C_1$-$C_6$-alkyl;

or $R^{13}$ and $R^{12}$ together with the carbon to which they are attached form a 4 to 7-membered heterocycloalkyl ring;

$R^{16}$ is independently selected from: H, $C_1$-$C_6$-alkyl, 4 to 7-membered heterocycloalkyl, 5-, 6-, 9 or 10-membered heteroaryl, C(S)-$L^1$-$R^{17}$ and C(O)-$L^1$-$R^{17}$;

-$L^1$- is absent or is independently selected from —O—, —S—, and —$NR^{18}$—;

$R^{17}$ is independently selected from $C_1$-$C_8$-alkyl, $C_1$-$C_8$-haloalkyl, $C_2$-$C_8$-alkenyl, $C_2$-$C_8$-alkynyl, $C_0$-$C_3$-alkylene-$R^{19}$; and —$CR^{20}R^{20}L^2R^{21}$;

-$L^2$- is independently selected from —O—, —S— and —$NR^{22}$—;

$R^{20}$ is independently at each occurrence selected from F, H and $C_1$-$C_4$-alkyl;

$R^{21}$ is independently selected from H, $C_1$-$C_8$-alkyl, $C_1$-$C_8$-haloalkyl, $C_2$-$C_8$-alkenyl, $C_2$-$C_8$-alkynyl and $C_0$-$C_3$-alkylene-$R^{23}$;

$R^{19}$ and $R^{23}$ are each independently at each occurrence selected from $C_3$-$C_6$-cycloalkyl, $_{3-6}$-heterocycloalkyl, 5- or 6-membered heteroaryl and phenyl;

y is an integer selected from 0, 1, 2, 3 and 4;

n is independently at each occurrence an integer selected from 0, 1 and 2;

wherein where any $R^1$-$R^{23}$ group is or forms part of an alkyl, alkenyl, alkynyl, haloalkyl, cycloalkyl, heterocycloalkyl, phenyl or heteroaryl group, that alkyl, haloalkyl, cycloalkyl, heterocycloalkyl, phenyl or heteroaryl group is optionally substituted, where chemically possible, by 1 to 5 substituents which are each independently selected at each occurrence from: oxo, =$NR^a$, =$NOR^a$, halo, nitro, cyano, $NR^aR^b$, $NR^aS(O)_2R^a$, $NR^aC(O)R^a$, $NR^aCONR^aR^a$, $NR^aCO_2R^a$, $OR^a$, $SR^a$, $S(O)R^a$, $S(O)_2R^a$, $S(O)_2NR^aR^a$, $CO_2R^aC(O)R^a$, $CONR^aR^a$, $C_1$-$C_4$-alkyl, $C_2$-$C_4$-alkenyl, $C_2$-$C_4$-alkynyl and $C_1$-$C_4$-haloalkyl; wherein $R^a$ is independently at each occurrence selected from H and $C_1$-$C_4$ alkyl; and $R^b$ is independently at each occurrence selected from H, $C_3$-$C_6$-cycloalkyl, $C_1$-$C_4$-alkyl, C(O)—$C_1$-$C_4$-alkyl and $S(O)_2$—$C_1$-$C_4$-alkyl;

or an agronomically acceptable salt or N-oxide thereof.

20. A compound of paragraph 19, wherein $L^s$ is —S—C($R^2R^3$)—.

21. A compound of paragraph 19 or paragraph 20, wherein each of $X^1$, $X^2$, $X^3$ and $X^4$ are carbon.

22. A compound of paragraph 19 or paragraph 20, wherein a single one of $X^1$, $X^2$, $X^3$ and $X^4$ is nitrogen.

23. A compound of any one of paragraphs 19 to 22, wherein $R^1$ is a 5- or 6-membered heteroaryl group having a nitrogen atom in the ring neighbouring the carbon through which $R^1$ is connected to the rest of the molecule.

24. A compound of paragraph 23, wherein $R^1$ has the structure:

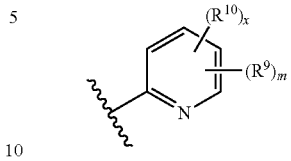

wherein x is an integer selected from 0, 1, 2, 3 and 4; and m is an integer selected from 0 and 1.

25. A compound of paragraph 24, wherein $R^1$ has the structure:

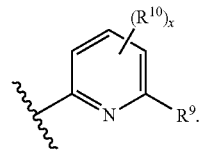

26. A compound of paragraph 23, wherein $R^1$ has the structure

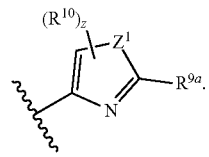

wherein $Z^1$ is independently selected from O and S; $R^{9a}$ is either absent or is $NR^{15}R^{16}$; and wherein z is an integer independently selected from 0, 1 and 2.

27. A compound of paragraph 26, wherein $R^1$ has the structure

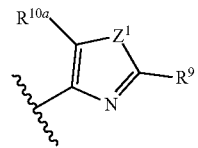

wherein $Z^1$ is independently selected from O and S; $R^{10a}$ is independently selected from: H, halo, nitro, cyano, $NR^{12}R^{13}$, $NR^{12}S(O)_2R^{12}$, $NR^{12}C(O)R^{12}$, $NR^{12}CONR^{12}R^{12}$, $NR^{12}CO_2R^{12}$, $OR^{12a}$, $SR^{12}$, $S(O)R^{12}$, $OS(O)_2R^{12}$, $S(O)_2R^{12}$, $S(O)_2NR^{12}R^{12}$, $CO_2R^{12}$, $C(O)R^{12}$, $CONR^{12}R^{12}$, $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl.

28. A compound of paragraph 26 or paragraph 27, wherein $Z^1$ is S.

29. A compound of any one of paragraphs 19 to 28, wherein $R^{16}$ is selected from C(S)-$L^1$-$R^{17}$ and C(O)-$L^1$-$R^{17}$.

30. A compound of any one of paragraphs 19 to 29, wherein $R^2$ and $R^3$ are each H.

31. A compound of any one of paragraphs 19 to 30, wherein $R^4$ is substituted at a position adjacent to the point of connection of $R^4$ to the rest of the molecule with an $R^{11b}$ group, wherein $R^{11b}$ is selected from $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl.

32. A compound of paragraph 31, wherein $R^4$ has the structure:

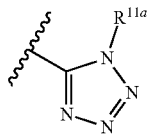

wherein $R^{11a}$ is selected from $C_1$-$C_4$-alkyl, $C_3$-$C_4$-alkenyl, $C_3$-$C_4$-alkynyl, phenyl, $C_0$-$C_6$-cycloalkyl, $_{3-6}$-heterocycloalkyl, 5- or 6-membered heteroaryl and $C_1$-$C_4$-haloalkyl.

33. A compound of paragraph 32, wherein $R^{11a}$ is $C_1$-$C_4$-alkyl.

34. A compound of any one of paragraphs 19 to 33, wherein y is 0.

35. A method for controlling fungal diseases, the method comprising applying an agronomically effective and substantially non-phytotoxic quantity of a compound of any one of paragraphs 19 to 34 to seeds of plants, to plants themselves or to an area where it is intended that plants will grow.

36. A use of a compound of any one of paragraphs 19 to 34 to control fungal diseases.

37. A fungicidal composition comprising an effective and non-phytotoxic amount of an active compound of any one of paragraphs 19 to 34.

DETAILED DESCRIPTION

The term $C_m$-$C_n$ refers to a group with m to n carbon atoms.

The term "alkyl" refers to a monovalent linear or branched saturated hydrocarbon chain. For example, $C_1$-$C_6$-alkyl may refer to methyl, ethyl, n-propyl, iso-propyl, n-butyl, sec-butyl, tert-butyl, n-pentyl and n-hexyl. The alkyl groups may be unsubstituted or substituted by one or more substituents. Specific substituents for each alkyl group independently may be fluorine, $OR^a$ or $NHR^a$.

The term "alkylene" refers to a bivalent linear saturated hydrocarbon chain. For example, $C_1$-$C_3$-alkylene may refer to methylene, ethylene or propylene. The alkylene groups may be unsubstituted or substituted by one or more substituents. Specific substituents for each alkylene group independently may be methyl, fluorine, $OR^a$ or $NHR^a$. For the absence of doubt, a $C_0$-alkylene is a bond.

The term "haloalkyl" refers to a hydrocarbon chain substituted with at least one halogen atom independently chosen at each occurrence from: fluorine, chlorine, bromine and iodine. The halogen atom may be present at any position on the hydrocarbon chain. For example, $C_1$-$C_6$-haloalkyl may refer to chloromethyl, fluoromethyl, trifluoromethyl, chloroethyl e.g. 1-chloromethyl and 2-chloroethyl, trichloroethyl e.g. 1,2,2-trichloroethyl, 2,2,2-trichloroethyl, fluoroethyl e.g. 1-fluoromethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl. A haloalkyl group may be a fluoroalkyl group, i.e. a hydrocarbon chain substituted with at least one fluorine atom. Thus, a haloalkyl group may have any amount of halogen substituents. The group may contain a single halogen substituent, it may have two or three halogen substituents, or it may be saturated with halogen substituents.

The term "alkenyl" refers to a branched or linear hydrocarbon chain containing at least one double bond. The double bond(s) may be present as the E or Z isomer. The double bond may be at any possible position of the hydrocarbon chain. For example, "$C_2$-$C_6$-alkenyl" may refer to ethenyl, propenyl, butenyl, butadienyl, pentenyl, pentadienyl, hexenyl and hexadienyl. The alkenyl groups may be unsubstituted or substituted by one or more substituents. Specific substituents for any saturated carbon atom in each alkenyl group independently may be fluorine, $OR^a$ or $NHR^a$.

The term "alkynyl" refers to a branched or linear hydrocarbon chain containing at least one triple bond. The triple bond may be at any possible position of the hydrocarbon chain. For example, "$C_2$-$C_6$-alkynyl" may refer to ethynyl, propynyl, butynyl, pentynyl and hexynyl. The alkynyl groups may be unsubstituted or substituted by one or more substituents. Specific substituents for any saturated carbon atom in each alkynyl group independently may be fluorine, $OR^a$ or $NHR^a$.

The term "cycloalkyl" refers to a saturated hydrocarbon ring system containing 3, 4, 5 or 6 carbon atoms. For example, "$C_3$-$C_6$-cycloalkyl" may refer to cyclopropyl, cyclobutyl, cyclopentyl, cyclohexyl. The cycloalkyl groups may be unsubstituted or substituted by one or more substituents. Specific substituents for each cycloalkyl group independently may be fluorine, $OR^a$ or $NHR^a$.

The term "$_{y-z}$-membered heterocycloalkyl" refers to a y- to z-membered heterocycloalkyl group. Thus it may refer to a monocyclic or bicyclic saturated or partially saturated group having from y to z atoms in the ring system and comprising 1 or 2 heteroatoms independently selected from O, S and N in the ring system (in other words 1 or 2 of the atoms forming the ring system are selected from O, S and N). By partially saturated it is meant that the ring may comprise one or two double bonds. This applies particularly to monocyclic rings with from 5 to 6 members. The double bond will typically be between two carbon atoms but may be between a carbon atom and a nitrogen atom. A heterocycloalkyl group may mean a saturated heterocycloalkyl group. Examples of heterocycloalkyl groups include; piperidine, piperazine, morpholine, thiomorpholine, pyrrolidine, tetrahydrofuran, tetrahydrothiophene, dihydrofuran, tetrahydropyran, dihydropyran, dioxane, azepine. A heterocycloalkyl group may be unsubstituted or substituted by one or more substituents. Specific substituents for any saturated carbon atom in each heterocycloalkyl group may independently be fluorine, $OR^a$ or $NHR^a$.

Aryl groups may be any aromatic carbocyclic ring system (i.e. a ring system containing $2(2n+1)\pi$ electrons). Aryl groups may have from 6 to 12 carbon atoms in the ring system. Aryl groups will typically be phenyl groups. Aryl groups may be naphthyl groups or biphenyl groups.

In any of the above aspects and embodiments, heteroaryl groups may be any aromatic (i.e. a ring system containing $2(2n+1)\pi$ electrons) 5 or 6 membered ring system comprising from 1 to 4 heteroatoms independently selected from O, S and N (in other words from 1 to 4 of the atoms forming the ring system are selected from O, S and N). Thus, any heteroaryl groups may be independently selected from: 5 membered heteroaryl groups in which the heteroaromatic ring is substituted with 1-4 heteroatoms independently selected from O, S and N; and 6-membered heteroaryl groups in which the heteroaromatic ring is substituted with 1-3 (e.g. 1-2) nitrogen atoms. Specifically, heteroaryl groups may be independently selected from: pyrrole, furan, thiophene, pyrazole, imidazole, oxazole, isoxazole, triazole, oxadiazole, thiadiazole, tetrazole; pyridine, pyridazine, pyrimidine, pyrazine, triazine.

It may be that, in any group which is an aryl or heteroaryl group, that aryl or heteroaryl group may be unsubstituted or is optionally substituted, where chemically possible, by 1 to 5 substituents which are each independently selected at each occurrence from: halo, nitro, cyano, $NR^aR^a$, $NR^aS(O)_2R^a$, $NR^aC(O)R^a$, $NR^aCONR^aR^a$, $NR^aCO_2R^a$, $OR^a$, $SR^a$, $S(O)R^a$, $S(O)_2R^a$, $S(O)_2NR^aR^a$, $CO_2R^aC(O)R^a$, $CONR^aR^a$, $CR^bR^bNR^aR^a$, $CR^bR^bOR^a$, $C_1$-$C_4$-alkyl, $C_2$-$C_4$-alkenyl, $C_2$-$C_4$-alkynyl and $C_1$-$C_4$-haloalkyl; wherein $R^a$ is as described above for formula I.

Compounds of the invention containing one or more asymmetric carbon atoms can exist as two or more stereoisomers. Where a compound of the invention contains a double bond such as a C=C or C=N group, geometric cis/trans (or Z/E) isomers are possible. Where structural isomers are interconvertible via a low energy barrier, tautomeric isomerism ('tautomerism') can occur. This can take the form of proton tautomerism in compounds of the invention containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of the invention, including compounds exhibiting more than one type of isomerism, and mixtures of one or more thereof. Also included are acid addition or base salts wherein the counter ion is optically active, for example, d-lactate or l-lysine, or racemic, for example, dl-tartrate or dl-arginine.

The compounds of the invention may be obtained, stored and/or used in the form of an agronomically acceptable salt. Suitable salts include, but are not limited to, salts of acceptable inorganic acids such as hydrochloric, sulfuric, phosphoric, nitric, carbonic, boric, sulfamic, and hydrobromic acids, or salts of agronomically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulfonic, toluenesulfonic, benzenesulfonic, salicylic, sulfanilic, aspartic, glutamic, edetic, stearic, palmitic, oleic, lauric, pantothenic, tannic, ascorbic and valeric acids. Suitable salts also include salts of inorganic and organic bases, e.g. counterions such as Na, Ca, K, Li, Mg, ammonium, trimethylsulfonium. The compounds may also be obtained, stored and/or used in the form of an N-oxide.

Cis/trans isomers may be separated by conventional techniques well known to those skilled in the art, for example, chromatography and fractional crystallisation.

Conventional techniques for the preparation/isolation of individual enantiomers when necessary include chiral synthesis from a suitable optically pure precursor or resolution of the racemate (or the racemate of a salt or derivative) using, for example, chiral high pressure liquid chromatography (HPLC). Thus, chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and for specific examples, 0 to 5% by volume of an alkylamine e.g. 0.1% diethylamine. Concentration of the eluate affords the enriched mixture.

Alternatively, the racemate (or a racemic precursor) may be reacted with a suitable optically active compound, for example, an alcohol, or, in the case where the compound of the invention contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, "Stereochemistry of Organic Compounds" by E. L. Eliel and S. H. Wilen (Wiley, 1994).

The activity of the compounds of the present invention can be assessed by a variety of in silico, in vitro and in vivo assays. In silico analysis of a variety of compounds has been demonstrated to be predictive of ultimate in vitro and even in vivo activity.

The present invention also includes all environmentally acceptable isotopically-labelled compounds of formulae (I) to (XII) and their syntheses, wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

Isotopically-labelled compounds can generally be prepared by conventional techniques known to those skilled in the art or by processes analogous to those described using an appropriate isotopically-labelled reagent in place of the non-labelled reagent previously employed.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

If appropriate, the compounds of the invention can, at certain concentrations or application rates, be used as fungicides.

According to another aspect of the present invention, there is provided a method for controlling the fungal diseases of plants, crops or seeds, the method comprising applying an agronomically effective and substantially non-phytotoxic quantity of a compound according to the invention to the seeds of the plants, to the plants themselves or to the area where it is intended that the plants will grow.

The pesticide may be applied as a seed treatment, foliar application, stem application, drench or drip application (chemigation) to the seed, the plant or to the fruit of the plant or to soil or to inert substrate (e.g. inorganic substrates like sand, rockwool, glasswool; expanded minerals like perlite, vermiculite, zeolite or expanded clay), Pumbe, Pyroclastic materials or stuff, synthetic organic substrates (e.g. polyurethane) organic substrates (e.g. peat, composts, tree waste products like coir, wood fibre or chips, tree bark) or to a liquid substrate (e.g. floating hydroponic systems, Nutrient Film Technique, Aeroponics).

In a further aspect, the present invention also relates to a fungicidal composition comprising an effective and non-phytotoxic amount of an active compound of the invention. The composition may further comprise one or more additional fungicides.

The term "effective and non-phytotoxic amount" means an amount of pesticide according to the invention which is sufficient to control or destroy any of the targeted pests present or liable to appear on the crops and which does not have any significant detrimental effect on the crops or indeed has a positive effect on plant vigour and yield in the absence of target organism. The amount will vary depending on the pest to be controlled, the type of crop, the climatic conditions and the compounds included in the pesticidal composition. This amount can be determined by systematic field trials, which are within the capabilities of a person skilled in the art.

Depending on their particular physical and/or chemical properties, the active compounds of the invention can be formulated as solutions, emulsions, suspensions, powders, foams, pastes, granules, aerosols, microencapsulations in polymeric substances and in coating materials for seed, and also as ULV cold and warm fogging formulations.

The active compounds can be used neat, or in the form of a formulation, e.g. ready-to-use solutions, emulsions, water- or oil-based suspensions, powders, wettable powders, pastes, soluble powders, dusts, soluble granules, granules for broadcasting, suspoemulsion concentrates, natural substances impregnated with active compound, synthetic substances impregnated with active compound, fertilizers and also microencapsulations in polymeric substances. Application may be carried out, for example, by watering, spraying, atomizing, broadcasting, dusting, foaming, spreading, etc. It is also possible to apply the active compounds by the ultra-low volume method or to inject the preparation of active compound or the active compound itself into the soil. It is also possible to treat the seed of the plants.

Formulations containing the compounds of the invention are produced in a known manner, for example by mixing the compounds with extenders (e.g. liquid solvents and/or solid carriers), optionally with the use of surfactants (e.g. emulsifiers and/or dispersants and/or foam-formers). The formulations are prepared either in factories/production plants or alternatively before or during the application.

Auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulfones and sulfoxides (such as dimethyl sulfoxide).

If the extender used is water, it is also possible to use, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and also their ethers and esters, ketones such as acetone, methyl ethyl ketone, methyl isobutyl ketone or cyclohexanone, strongly polar solvents such as dimethylformamide and dimethyl sulfoxide.

Suitable solid carriers are: for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and also protein hydrolysates; suitable dispersants are nonionic and/or ionic substances, for example from the classes of the alcohol-POE and/or -POP ethers, acid and/or POP-POE esters, alkylaryl and/or POP-POE ethers, fat- and/or POP-POE adducts, POE- and/or POP-polyol derivatives, POE- and/or POP-sorbitan- or -sugar adducts, alkyl or aryl sulfates, alkyl- or arylsulfonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulfonic acid derivatives, unmodified and modified celluloses, aromatic and/or aliphatic sulfonic acids and their adducts with formaldehyde.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

Further additives may be mineral and vegetable oils. It is also possible to add colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc. Other possible additives are perfumes, mineral or vegetable, optionally modified oils and waxes.

The formulations may also comprise stabilizers, e.g. low-temperature stabilizers, preservatives, antioxidants, light stabilizers or other agents which improve chemical and/or physical stability.

The formulations generally comprise between 0.01 and 98% by weight of active compound, preferably between 0.1 and 95% and particularly preferably between 0.5 and 90%.

The active compounds according to the invention can also be used as a mixture with other known fungicides, for example, to improve the activity spectrum or to reduce or slow the development of resistance.

A mixture with other known active compounds such as nematicides, acaricides, herbicides, insecticides, bactericides or other fungicides, or with fertilizers and growth regulators, safeners or semiochemicals is also possible.

Exemplary application rates of the active compounds according to the invention are: when treating leaves: from 0.1 to 10 000 g/ha, preferably from 10 to 1000 g/ha, particularly preferably from 50 to 300 g/ha (when the application is carried out by watering or dripping, it is even possible to reduce the application rate, especially when inert substrates such as rock wool or perlite are used); when treating seed: from 2 to 200 g per 100 kg of seed, preferably from 2.5 to 150 g per 100 kg of seed, and particularly preferably from 2.5 to 25 g per 100 kg of seed, very particularly preferably from 2.5 to 12.5 g per 100 kg of seed; when treating the soil: from 0.1 to 10 000 g/ha, preferably from 1 to 5000 g/ha.

The compositions according to the invention are suitable for protecting any plant variety which is employed in agriculture, in the greenhouse, in forests or in horticulture and, in particular, cereals (e.g. wheat, barley, rye, millet and oats), maize, cotton, soya beans, rice, potatoes, sunflowers, beans, coffee, beet (for example sugar beet and fodder beet), peanuts, vegetables (e.g. tomatoes, cucumbers, onions and lettuce), lawns, fruit and nut trees (e.g. apples, pears, peaches, nectarines, apricots, hazelnut, pecan, macadamia, pistachio), soft fruit (e.g. strawberries, raspberries, blackcurrants, redcurrants), grapevines, bananas, cocoa and ornamental plants.

The active compounds of the invention, in combination with good plant tolerance and favourable toxicity to warm-blooded animals and being tolerated well by the environment, are suitable for protecting plants and plant organs, for increasing the harvest yields, for improving the quality of the harvested material and for controlling pests, in particular fungal diseases, which are encountered in agriculture, in horticulture, in animal husbandry, in forests, in gardens and leisure facilities, in the protection of stored products and of materials, and in the hygiene sector. They may be preferably employed as crop protection agents.

Use as Fungicides

The compounds of the invention have activity as fungicides.

The following are illustrative examples of agricultural pests that may be controlled by fungicidal compounds:

Oomycete diseases such as: *Albugo* diseases caused for example by *Albugo Candida; Bremia* diseases, caused for example by *Bremia lactucae; Peronospora* diseases, caused for example by *Peronospora pisi* or *P. brassicae; Phytophthora* diseases, caused for example by *Phytophthora infestans; Plasmopara* diseases, caused for example by *Plasmopara viticola; Pseudoperonospora* diseases, caused for example by *Pseudoperonospora humuli* or *Pseudoperonospora cubensis; Pythium* diseases, caused for example by *Pythium ultimum;*

The compounds of the invention may be active against a broad spectrum of oomycete fungal diseases. Alternatively, they may be active specifically against certain oomycete diseases but not others.

Notable oomycete fungal diseases are:
*Plasmopara viticola*
*Phytophthora infestans*
*Pythium ultimum*
*Bremia lactuca*
*Peronospora* spp In additional to their fungicidal activity, the compounds of the invention may also have some activity against other microbes, e.g. bacteria.

The fungicidal compounds of the invention may also be used in the treatment of fungal diseases of humans and animals (e.g. mammals). Likewise, the bactericidal compounds of the invention may be used in the treatment of bacterial diseases of humans and animals. Thus, the invention includes a method of treating a fungal or bacterial disease, the method comprising administering a therapeutic amount of an antifungal agent of the invention to a subject (e.g. a human subject) in need thereof. The compound may be formulated for topical administration to the infected area of the body or it may be formulated for oral or parenteral administration.

Synthesis

The skilled person will appreciate that adaptation of methods known in the art could be applied in the manufacture of the compounds of the present invention.

For example, the skilled person will be immediately familiar with standard textbooks such as "Comprehensive Organic Transformations—A Guide to Functional Group Transformations", R C Larock, Wiley-VCH (1999 or later editions); "March's Advanced Organic Chemistry—Reactions, Mechanisms and Structure", M B Smith, J. March, Wiley, (5th edition or later); "Advanced Organic Chemistry, Part B, Reactions and Synthesis", F A Carey, R J Sundberg, Kluwer Academic/Plenum Publications, (2001 or later editions); "Organic Synthesis—The Disconnection Approach", S Warren (Wiley), (1982 or later editions); "Designing Organic Syntheses" S Warren (Wiley) (1983 or later editions); "Heterocyclic Chemistry", J. Joule (Wiley 2010 edition or later); ("Guidebook To Organic Synthesis" R K Mackie and D M Smith (Longman) (1982 or later editions), etc., and the references therein as a guide.

The skilled person is familiar with a range of strategies for synthesising organic and particularly heterocyclic molecules and these represent common general knowledge as set out in text books such as Warren "Organic Synthesis: The Disconnection Approach"; Mackie and Smith "Guidebook to Organic Chemistry"; and Clayden, Greeves, Warren and Wothers "Organic Chemistry".

The skilled chemist will exercise his judgement and skill as to the most efficient sequence of reactions for synthesis of a given target compound and will employ protecting groups as necessary. This will depend inter alia on factors such as the nature of other functional groups present in a particular substrate. Clearly, the type of chemistry involved will influence the choice of reagent that is used in the said synthetic steps, the need, and type, of protecting groups that are employed, and the sequence for accomplishing the protection/deprotection steps. These and other reaction parameters will be evident to the skilled person by reference to standard textbooks and to the examples provided herein.

Sensitive functional groups may need to be protected and deprotected during synthesis of a compound of the invention. This may be achieved by conventional methods, for example as described in "Protective Groups in Organic Synthesis" by T W Greene and P G M Wuts, John Wiley & Sons Inc. (1999), and references therein.

Throughout this specification these abbreviations have the following meanings:

| | |
|---|---|
| CDI—carbonyldiimidazole | DCM—dichloromethane |
| DDQ—2,3-dichloro-5,6-dicyano-1,4-benzoquinone | DIPEA—diisopropylethylamine |
| DMAP—N,N-dimethyl-4-aminopyridine | DMF—N,N-dimethylformamide |
| DMSO—dimethylsulfoxide | Im—imidazole |
| LDA—lithium diisopropylamide | NBS—N-bromosuccinimide |
| PE—petroleum ether | PMB—para-methoxybenzyl |
| TBAF—tetrabutylammonium fluoride | Tf—trifluoromethylsulfonyl |
| THF—tetrahydrofuran | TMS—trimethylsilyl |
| TCDI—thiocarbonyldiimidazole | TBSO—t-butyldimethylsilyloxy |
| HATU—1-[Bis(dimethylamino)methylene]-1H-1,2,3-triazolo[4,5-b]pyridinium 3-oxide hexafluorophosphate | |

Certain compounds of the invention can be made according to the general synthetic scheme below. Certain compounds of the invention can be made according to or by methods analogous to the methods described in Examples 1 to 90.

General Synthetic Scheme

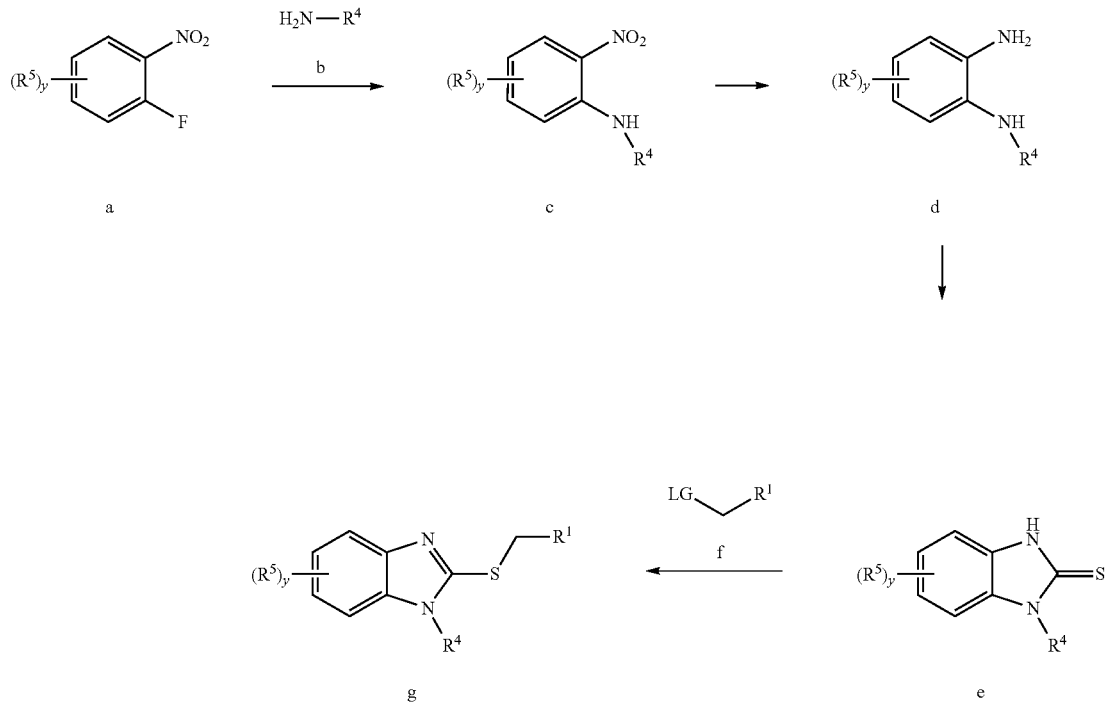

Certain compounds of the invention can be made starting from ortho-fluoro nitro benzenes a. Treatment with amine b in the presence of a base (e.g. NaH in DMF) can provide nitroanilines of formula c. Reduction of the nitro group to an amine (e.g. using ammonium formate and palladium on carbon in ethanol) can provide the diamines d. Compounds of formula e can be formed (e.g. by treating with TCDI in THF or DMF). Reaction with electrophile f (in which LG is a leaving group, for example OTf, Cl, Br, I) provides compounds of formula g, a subset of compounds of the invention (Scheme A).

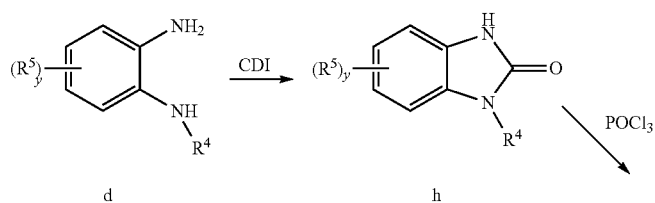

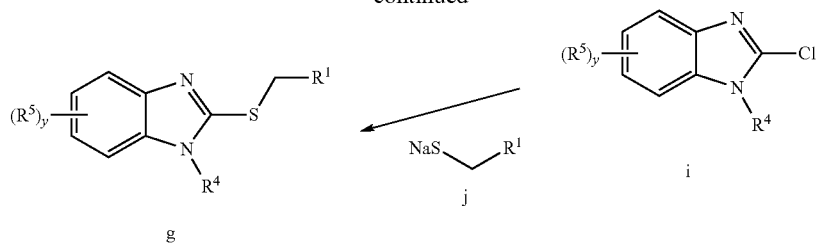

Alternatively, certain compounds of the invention can be made starting from diamine d. Treatment with carbonyl diimidazole (e.g. in THF at room temperature or in DMF at elevated temperatures) can provide ureas of formula h. Treatment with phosphorus oxychloride (e.g. at reflux) can provide chlorobenzimidazoles of formula i. Reaction with a sodium thiolate j (e.g. in DMF at room temperature) provides compounds of formula g, a subset of compounds of the invention (Scheme B).

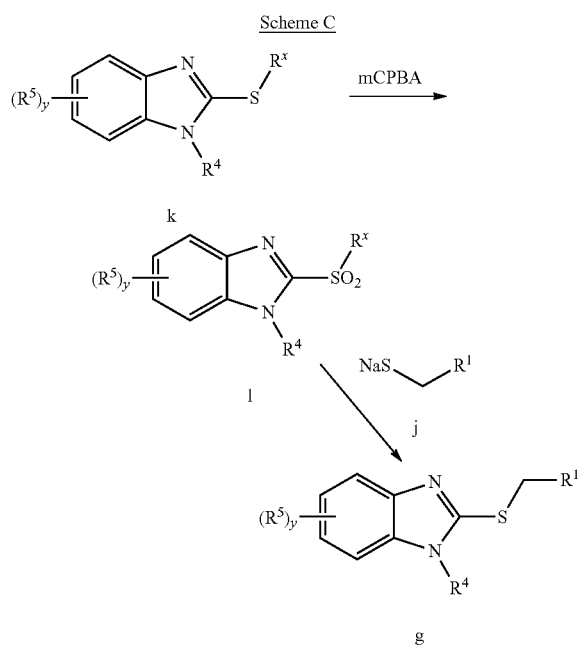

As a further alternative, certain compounds of the invention can be made from thiobenzimidazoles of formula k (a subset of compounds of formula g in which $R^x$ can be any convenient group). Treatment with mCPBA (e.g. in DCM at room temperature) can give sulfones of formula I. Reaction with a sodium thiolate j (e.g. in DMF at room temperature) provides compounds of formula g, a subset of compounds of the invention (Scheme C).

Analytical Procedures

Flash chromatography was carried out using a Biotage Isolera 4, with Biotage® SNAP KP-Sil cartridges, packed with 50 μm silica particles with a surface area of 500 m²/g, or alternative cartridges (e.g. Puriflash, produced by Interchim) where stated. Visualisation was carried out with UV light (254 nm) and by staining with either potassium permanganate, phosphomolybdic acid (PMA) or ninhydrin solutions.

All $^1$H NMR spectra were obtained on a Bruker AVIII 400 with 5 mm QNP or Bruker AVI 500 with 5 mm QNP or Bruker DPX 300. Chemical shifts are expressed in parts per million (δ) and are referenced to the solvent. Coupling constants J are expressed in Hertz (Hz).

MS was carried out on a Waters Alliance ZQ MS, using a YMC-Triart C18 50×2 mm, 5 micron LC column (solvent: 5-90% gradient of acetonitrile in water (with 1% by volume of 28% (by weight) aqueous ammonia solution)) by Method A or C, or (solvent: 5-90% gradient of acetonitrile in water (with 1% formic acid) by Method B or D. Flow rate 0.8 mL/min. Wavelengths were 254 and 210 nM.

Method A (5 Minute Basic pH)

Column: YMC-Triart C18 50×2 mm, 5 μm. Flow rate: 0.8 mL/min. Injection volume: 5 μL.

| Mobile Phase | A | $H_2O$ | | |
|---|---|---|---|---|
| | B | $CH_3CN$ | | |
| | C | 50% $H_2O$/50% $CH_3CN$ + 1.0% ammonia (aq.) | | |
| Time (min) | | A (%) | B (%) | C (%) |
| 0 | | 95 | 0 | 5 |
| 4 | | 0 | 95 | 5 |
| 4.4 | | 0 | 95 | 5 |
| 4.5 | | 95 | 5 | 0 |
| 4.5 | | | STOP | |

Method B (5 Minute Acidic pH)

Column: YMC-Triart C18 50×2 mm, 5 μm. Flow rate: 0.8 mL/min. Injection volume: 5 μL.

| Mobile Phase | A | $H_2O$ | | |
|---|---|---|---|---|
| | B | $CH_3CN$ | | |
| | C | 50% $H_2O$/50% $CH_3CN$ + 1.0% formic acid | | |
| Time (min) | | A (%) | B (%) | C (%) |
| 0 | | 95 | 0 | 5 |
| 4 | | 0 | 95 | 5 |
| 4.4 | | 0 | 95 | 5 |
| 4.5 | | 95 | 5 | 0 |
| 4.5 | | | STOP | |

Method C (15 Minute Basic pH)

Column YMC Triart-C18 50×2 mm, 5 μm Flow rate: 0.8 mL/min. Injection volume: 10 μL

| Mobile Phase | A | $H_2O$ | | |
|---|---|---|---|---|
| | B | $CH_3CN$ | | |
| | C | 50% $H_2O$/50% $CH_3CN$ + 1.0% ammonia (aq.) | | |
| Time (min) | | A (%) | B (%) | C (%) |
| 0 | | 95 | 0 | 5 |
| 2.0 | | 95 | 0 | 5 |
| 12.0 | | 0 | 95 | 5 |

-continued

| | | | |
|---|---|---|---|
| 14.0 | 0 | 95 | 5 |
| 14.2 | 95 | 0 | 5 |

Method D (15 Minute Acidic pH)

Column YMC Triart-C18 50×2 mm, 5 µm Flow rate: 0.8 mL/min. Injection volume: 10 µL

| Mobile Phase | A | H$_2$O | |
| | B | CH$_3$CN | |
| | C | 50% H$_2$O/50% CH$_3$CN + 1.0% formic acid | |

| Time (min) | A (%) | B (%) | C (%) |
|---|---|---|---|
| 0 | 95 | 0 | 5 |
| 2.0 | 95 | 0 | 5 |
| 12.0 | 0 | 95 | 5 |
| 14.0 | 0 | 95 | 5 |
| 14.2 | 95 | 0 | 5 |

Alternatively MS was carried on a Waters Acquity UPLC-QDA UV-MS system using Method E (high pH) or Method F (low pH):

Method F (3.5 Minute Acidic pH)

Mobile phases: Water (A)/Acetonitrile (B) both with 0.1% (v/v) Formic Acid

| Time | % A | % B | Flow rate (mL/min) |
|---|---|---|---|
| Initial | 98 | 2 | 1.0 |
| 0.2 | 98 | 2 | 1.0 |
| 2.5 | 2 | 98 | 1.0 |
| 3.0 | 2 | 98 | 1.0 |
| 3.1 | 98 | 2 | 1.0 |
| 3.5 | 98 | 2 | 1.0 |

Column: CSH C18 2.1×50 mm, 1.7 µm@50° C.

All reagents were obtained from commercial suppliers and used as supplied unless otherwise stated.

All examples are named using ChemBioDraw Ultra 14.0.

Reactions were conducted at ambient temperature (RT) unless otherwise stated.

Synthetic Intermediates 2,2-Difluoro-2-phenoxy acetic acid A

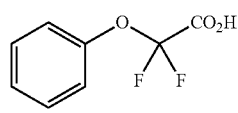 [SMILES: O=C(O)C(F)(F)Oc1ccccc1]

Sodium hydride (4.36 g, 109 mmol) was added in several portions to a stirred solution of phenol (5.00 g, 53.1 mmol) and chlorodifluoroacetic acid (4.50 mL, 53.1 mmol) in 1,4-dioxane (200 mL) at 0° C. and the reaction mixture was stirred at 0° C. until effervescence ceased. The reaction mixture was slowly heated to 101° C. and was allowed to reflux for 16 hours. The mixture was concentrated in vacuo. Ethyl acetate (300 mL) and water (200 mL) were added and the biphasic mixture was stirred vigorously for 30 minutes at room temperature. The pH of the separated aqueous phase was adjusted to pH 8 with 5 M hydrochloric acid (to pH 1) then saturated aqueous sodium bicarbonate. The solution was extracted with ethyl acetate (2×150 mL) to remove unreacted phenol and these extracts were discarded. The aqueous phase was acidified to pH 1 with 5M HCl and extracted with ethyl acetate (3×150 mL). The organic layers were combined, washed with brine, dried (MgSO$_4$), filtered and concentrated to give 2,2-difluoro-2-phenoxyacetic acid A (7.36 g, 74%) as a pale brown oil, purity ca. 90% by NMR.

$^1$H NMR (500 MHz, CDCl$_3$) δ 9.36 (br. s, 1H), 7.44-7.31 (m, 2H), 7.35-7.18 (m, 3H); LCMS (method A): 0.89 min (187.2, [M-H]$^-$)

6-[(tert-Butyl(dimethyl)silyl)oxymethyl]pyridin-2-amine B

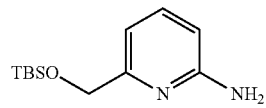 [SMILES: CC(C)(C)[Si](C)(C)OCc1cccc(N)n1]

A solution of (6-aminopyridin-2-yl)methanol (2.98 g, 24.0 mmol) in DMF (20 mL) was treated with imidazole (3.44 g, 50.5 mmol) and tert-butyldimethylchlorosilane (3.80 g, 25.2 mmol) at 25° C. After 22 h the solution was diluted with EtOAc (100 mL), washed with water (3×100 mL) and brine, dried (MgSO$_4$) and concentrated to give 6-(((tert-butyldimethylsilyl)oxy)methyl)pyridin-2-amine B (5.85 g, 100%) as a waxy solid.

$^1$H NMR (500 MHz, CDCl$_3$) δ 7.48-7.41 (m, 1H), 6.86 (dd, J=7.4, 0.8 Hz, 1H), 6.37 (dd, J=8.1, 0.7 Hz, 1H), 4.66 (s, 2H), 4.39 (s, 2H), 0.95 (s, 9H), 0.11 (s, 6H); LCMS (method A): 3.38 min (239, MH$^+$)

N-[6-[(tert-Butyl(dimethyl)silyl)oxymethyl]-2-pyridyl]-2,2-difluoro-2-phenoxy-acetamide C

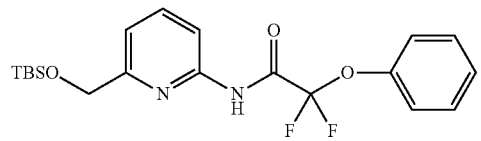 [SMILES: CC(C)(C)[Si](C)(C)OCc1cccc(NC(=O)C(F)(F)Oc2ccccc2)n1]

HATU (4.78 g, 12.6 mmol) was added to a stirred solution of 6-(((tert-butyldimethylsilyl)oxy)methyl)pyridin-2-amine B (2.00 g, 8.39 mmol), 2,2-difluoro-2-phenoxyacetic acid A (1.89 g, 10.1 mmol) and N,N-diisopropylamine (5.85 mL, 33.6 mmol) in DMF (5 mL). The mixture was heated to 50° C. and stirred for 16 hours then diluted with water and extracted with ethyl acetate (3×50 mL). The combined organic extracts were washed with water (3×50 mL), brine (50 mL), dried (MgSO$_4$) and concentrated to give a brown oil. This oil was purified by column chromatography on silica eluting with 2-16% EtOAc/PE to give N-(6-(((tert-butyldimethylsilyl)oxy)methyl)pyridin-2-yl)-2,2-difluoro-2-phenoxyacetamide C (2.68 g, 78%) as a colourless oil.

$^1$H NMR (500 MHz, CDCl$_3$) δ 8.70 (br. S, 1H), 8.09 (d, J=8.2 Hz, 1H), 7.79 (t, J=7.9 Hz, 1H), 7.40-7.32 (m, 3H), 7.29-7.22 (m, 3H), 4.72 (s, 2H), 0.95 (s, 9H), 0.11 (s, 6H).

N-(6-(((tert-Butyldimethylsilyl)oxy)methyl)pyridin-2-yl)cyclopropanecarboxamide C1

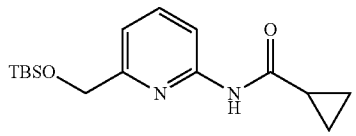 [SMILES: CC(C)(C)[Si](C)(C)OCc1cccc(NC(=O)C2CC2)n1]

Following the same procedure as for C, but using cyclopropanecarboxylic acid in place of 2,2-difluoro-2-phenoxyacetic acid and stirring at RT for 2 hours and then at 50° C. for 18 hours, with purification by column chromatography on silica, eluting with 0-20% EtOAc/PE, the title compound C1 was obtained in 57% yield.

$^1$H NMR (500 MHz, CDCl$_3$) δ 8.03 (d, J=8.3 Hz, 1H), 7.70 (t, J=7.9 Hz, 1H), 7.21 (d, J=7.5 Hz, 1H), 4.71 (s, 2H), 1.57-1.47 (m, 1H), 1.10 (m, 2H), 0.95 (s, 9H), 0.89 (dt, J=7.2, 4.2 Hz, 2H), 0.12 (s, 6H); LCMS (method A): 3.90 min, (307.4, MH$^+$).

N-(6-(((tert-Butyldimethylsilyl)oxy)methyl)pyridin-2-yl)-2-phenoxyacetamide C2

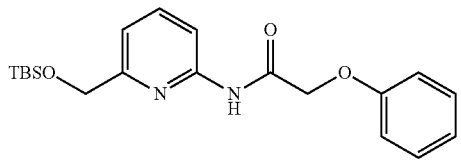 [SMILES: CC(C)(C)[Si](C)(C)OCc1cccc(NC(=O)COc2ccccc2)n1]

Phenoxyacetyl chloride (0.58 mL, 4.2 mmol) was added to a stirred solution of 6-(((tert-butyldimethylsilyl)oxy)methyl)pyridin-2-amine B (1.0 g, 5.0 mmol) and triethylamine (0.59 mL, 4.2 mmol) in DCM (15 mL). After 2 hours the reaction mixture was concentrated in vacuo and the residue was chromatographed on silica eluting with 10-60% EtOAc/PE to give N-(6-(((tert-butyldimethylsilyl)oxy)methyl)pyridin-2-yl)-2-phenoxyacetamide C2 (1.5 g, 98%) as a colourless oil.

$^1$H NMR (500 MHz, CDCl$_3$) δ 8.83 (s, 1H), 8.13 (d, J=8.2 Hz, 1H), 7.75 (t, J=7.9 Hz, 1H), 7.35 (t, J=8.0 Hz, 2H), 7.29 (d, J=7.6 Hz, 1H), 7.05 (t, J=7.4 Hz, 1H), 7.01 (d, J=8.0 Hz, 2H), 4.73 (s, 2H), 4.62 (s, 2H), 0.96 (s, 9H), 0.12 (s, 6H); LCMS (method A): 4.23 min (374.6, MH$^+$).

N-(6-(((tert-Butyldimethylsilyl)oxy)methyl)pyridin-2-yl)propionamide C3

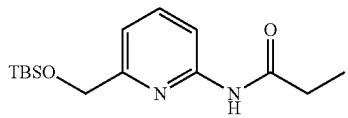 [SMILES: CCC(=O)Nc1cccc(CO[Si](C)(C)C(C)(C)C)n1]

Following the same procedure as for C2, but using propionyl chloride in place of phenoxyacetyl chloride and with stirring at RT overnight followed by removal of solvent in vacuo the title compound C3 was obtained as a white gum that was used directly in next step without chromatographic purification. LCMS (method B): 3.58 min (295.3, MH$^+$).

2,2-Difluoro-N-[6-(hydroxymethyl)-2-pyridyl]-2-phenoxy-acetamide D

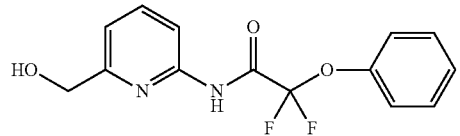 [SMILES: O=C(Nc1cccc(CO)n1)C(F)(F)Oc1ccccc1]

TBAF [1M solution in THF] (5.11 mL, 5.11 mmol) was added to a solution of N-(6-(((tert-butyldimethylsilyl)oxy)methyl)pyridin-2-yl)-2,2-difluoro-2-phenoxyacetamide C (1.74 g, 4.26 mmol) in THF (20 mL) at 0° C. and the reaction mixture was stirred at 0° C. for 3.5 hours. The mixture was diluted with ethyl acetate (10 mL), washed with water (20 mL) and brine (20 mL), dried (MgSO$_4$) and concentrated in vacuo to give a pale yellow oil which was chromatographed on silica eluting with 10-100% EtOAc/PE to give 2,2-difluoro-N-(6-(hydroxymethyl)pyridin-2-yl)-2-phenoxyacetamide D (1.15 g, 92%) as a pale yellow solid.

$^1$H NMR (500 MHz, CDCl$_3$) δ 8.76 (br s, 1H), 8.16 (d, J=8.2 Hz, 1H), 7.80 (t, J=7.9 Hz, 1H), 7.42 (t, J=7.9 Hz, 2H), 7.30 (t, J=9.5 Hz, 3H), 7.13 (d, J=7.6 Hz, 1H), 4.74 (s, 2H), 3.19 (br s, 1H).

Following the same procedure as for Synthetic Intermediate ("Int.") D, substituting the 2,2-difluoro-2-phenoxyacetate starting material ("SM") C with the required amide, there were thus obtained the following hydroxy intermediates:

| Int. | R$^1$ | SM | Yield | RT$^a$ | MH$^+$ |
|---|---|---|---|---|---|
| D1 | Cyclopropyl- | C1 | 82% | 1.03 (B) | 193.2 |
| D2 | Phenoxymethyl- | C2 | 50% | 1.91 (B) | 260.1 |
| D3 | Ethyl- | C3 | 82% | 0.92 (B) | 181.1 |

$^a$RT = LCMS retention time in minutes using indicated Method (A-D or -E)

N-(6-(Bromomethyl)pyridin-2-yl)-2,2-difluoro-2-phenoxyacetamide E

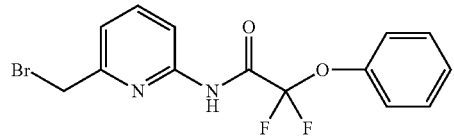 [SMILES: O=C(Nc1cccc(CBr)n1)C(F)(F)Oc1ccccc1]

A solution of 2,2-difluoro-N-(6-(hydroxymethyl)pyridin-2-yl)-2-phenoxyacetamide D (150 mg, 0.51 mmol) and carbon tetrabromide (186 mg, 0.56 mmol) in dry DCM (2 mL) was treated with triphenylphosphine (140 mg, 0.535 mmol) and stirred at RT for 24 hours. The reaction mixture was loaded directly onto silica (25 g Biotage KP-Sil cartridge) and eluted with 0-50% EtOAc/PE to give N-(6-(bromomethyl)pyridin-2-yl)-2,2-difluoro-2-phenoxyacetamide E (140 mg, 69%) as a colourless oil.

$^1$H NMR (500 MHz, CDCl$_3$) δ 8.79 (s, 1H), 8.19 (dd, J=8.2, 0.4 Hz, 1H), 7.80 (t, J=7.9 Hz, 1H), 7.44-7.39 (m, 2H), 7.32-7.27 (m, 4H), 4.46 (s, 2H).

2-(Bromomethyl)thiazole E1

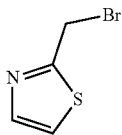

Following the same procedure as for E, but using 2-(hydroxymethyl)-1,3-thiazole in place of Int. D and stirring at RT for 1 h, with purification on silica eluting with 10-40% EtOAc/PE, the title compound E1 was obtained in 94% yield as a pale yellow oil. The product was unstable so was used immediately in the next step.

LCMS (method B): 1.84 min (178.0 and 180.0, MH$^+$, Br isotopes)

1-(1-Methyl-1H-tetrazol-5-yl)-1,3-dihydro-2H-benzo[d]imidazol-2-one F

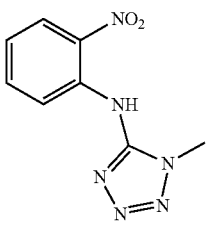

A stirred, ice-cooled suspension of 5-amino-1-methyltetrazole (5 g, 50.5 mmol) in dry DMF (40 mL) was treated with sodium hydride (60% in mineral oil, 3.03 g, 76 mmol) and stirred a further 15 min then about ⅔ of the 1-fluoro-2-nitrobenzene (5.32 ml, 50.5 mmol) was added dropwise over 15 min so as to maintain the internal temp around 20° C. or lower (did not exceed 25° C.). More sodium hydride (1.11 g, 27.8 mmol) was then added, followed dropwise by the remainder of the fluoronitrobenzene (in DMF, 2 mL) over a further 10 min. The dark red solution was stirred whilst warming to room temperature over 2.5 h then diluted cautiously with water (250 mL) and washed with Et$_2$O (250 mL). The aq. layer was acidified with 5M aq. HCl (13 mL, to pH 1). The solid was collected, washed with a little water (ca. 2×15 mL) and dried in vacuo to give 1-methyl-N-(2-nitrophenyl)-1H-tetrazol-5-amine F (9.29 g, 84%) as a yellow solid.

$^1$H NMR (500 MHz, CDCl$_3$) δ 10.59 (s, 1H), 8.76 (dd, J=8.6, 1.2 Hz, 1H), 8.32 (dd, J=8.5, 1.5 Hz, 1H), 7.75 (s, 1H), 7.17 (s, 1H), 4.06 (s, 3H); LCMS (method B): 2.21 min (221, MH$^+$).

Following the same procedure as for Synthetic Intermediate ("Int.") F, substituting 1-fluoro-2-nitrobenzene and/or 5-amino-1-methyltetrazole with the required o-fluoronitrobenzene (optionally substituted with $(R^5)_y$) and/or aminoheterocycle ($R^4$—NH$_2$), and generally with all of the NaH added at the start of the reaction, there were thus obtained the following intermediates:

| Int. | $(R^5)_y$ | $R^4$—NH$_2$ | Yield | RT$^a$ | MH$^+$ |
|---|---|---|---|---|---|
| F1 | y = 0 | 2-amino-3-methylpyridine | 53% | 3.16 (B) | 230.1 |
| F2 | y = 0 | 5-amino-1-methylpyrazole | 39%$^b$ | 2.37 (B) | 219.1 |
| F3 | y = 0 | 5-amino-3,4-dimethylisoxazole | 85%$^b$ | 2.82 (B) | 234.1 |
| F4 | 4-F | 5-amino-1-methyltetrazole | 57% | 2.32 (B) | 239.1 |
| F5 | y = 0 | 5-amino-3-methylisothiazole | 68% | 2.80 (B) | 236.1 |
| F6 | y = 0 | 3-aminoisoxazole | 85% | 2.74 (B) | 206.1 |
| F7 | y = 0 | 2-amino-3-methylpyrazine | 53%$^b$ | 2.80 (B) | 231.1 |
| F8 | 4,6-F$_2$ | 5-amino-1-methyltetrazole | 58% | 2.35 (B) | 257.1 |
| F9 | y = 0 | 1-methyl-1H-imidazol-2-amine | 38%$^b$ | 1.46 (B) | 219.1 |
| F10 | y = 0 | 4-amino-3,5-dichloropyridine | 31%$^b$ | 3.06 (B) | 285.9 |
| F11 | 4-Br | 5-amino-1-methyltetrazole | 80% | 2.70 (A) | 299.1 |
| F12 | 4-I | 5-amino-1-methyltetrazole | 66% | 2.71 (B) | 347.0 |
| F13 | 6-Cl | 5-amino-1-methyltetrazole | 97%$^c$ | 2.45 (B) | 255.1 |

$^a$RT = LCMS retention time in minutes using indicated Method (A-D or F);
$^b$Product obtained using an aqueous work-up, extracting with EtOAc, followed by chromatography on silica eluting with 0-50% EtOAc/PE;
$^c$Product obtained using an aqueous work-up, extracting with EtOAc, no further purification was required.

N-1-(1-Methyl-1H-tetrazol-5-yl)benzene-1,2-diamine G

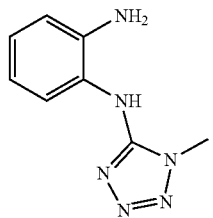 [SMILES: Cn1nnnc1Nc1ccccc1[N+](=O)[O-]]

A stirred suspension of 1-methyl-N-(2-nitrophenyl)-1H-tetrazol-5-amine F (2.46 g, 11.17 mmol) in ethanol (80 ml) under N$_2$ was treated with 10% palladium on activated charcoal (0.1 g) then ammonium formate (2.82 g, 44.7 mmol) and the mixture was heated under reflux for 6 h then cooled and filtered through Celite under N$_2$. The filter was washed with EtOAc and the combined filtrates were concentrated in vacuo to give crude product, 1.77 g, as a reddish solid. This material was loaded onto SiO$_2$ (5 g) and chromatographed on silica (24 g Puriflash) eluting with 0-10% MeOH/DCM to give N-1-(1-methyl-1H-tetrazol-5-yl)benzene-1,2-diamine G (1.3 g, 61%), as a red solid.

¹H NMR (500 MHz, DMSO) δ 8.15 (s, 1H), 7.19 (dd, J=7.8, 1.5 Hz, 1H), 6.96-6.89 (m, 1H), 6.74 (dd, J=8.0, 1.4 Hz, 1H), 6.56 (td, J=7.7, 1.5 Hz, 1H), 5.05 (s, 2H), 3.84 (s, 3H); LCMS (method A): 1.38 min (191, MH⁺).

Following the same procedure as for Synthetic Intermediate ("Int.") G, substituting the nitroaryl starting material ("SM") F with the required nitroaryl, there were thus obtained the following aniline intermediates:

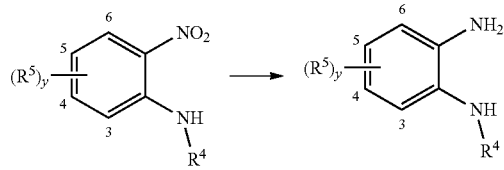

| SM | (R⁵)ᵧ | R⁴ | Aniline | Yield | RTᵃ | MH⁺ |
|---|---|---|---|---|---|---|
| F1 | y = 0 | 2-(3-methyl)pyridyl | G1ᵇ | 100% | 0.94(B) | 200.1 |
| F2 | y = 0 | 1-methylpyrazol-5-yl | G2 | 85% | 1.20(B) | 189.1 |
| F4 | 4-F | 1-methyltetrazol-5-yl | G4ᵇ | 100% | 1.12(B) | 209.1 |
| F8 | 4,6-F₂ | 1-methyltetrazol-5-yl- | G8ᵇ | 80% | 1.60(B) | 227.1 |
| F9 | y = 0 | 1-methylimidazol-2-yl | G9ᵇ | 100% | 0.80(B) | 189.2 |

ᵃRT = LCMS retention time in minutes using indicated Method (A-D or F);
ᵇProduct used directly in next step without need for chromatographic purification.

N¹-(3,4-Dimethylisoxazol-5-yl)benzene-1,2-diamine
G3

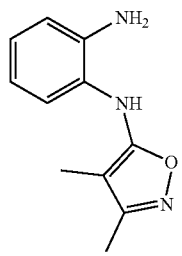

Sodium hydrogen carbonate (209 mg, 2.49 mmol) then sodium hydrosulfite (649 mg, 3.73 mmol) were added to a stirred solution of 3,4-dimethyl-N-(2-nitrophenyl)isoxazol-5-amine F3 (290 mg, 1.24 mmol) in THF (3 mL) and water (1.5 mL). The reaction mixture was stirred at 60° C. for 22 h then quenched with water (5 mL) and extracted into EtOAc (2×10 mL). The combined organics were washed with brine, dried (MgSO₄) and chromatographed on silica (10 g Biotage Snap KP-Sil column) eluting with 0-5% MeOH/DCM to give N¹-(3,4-dimethylisoxazol-5-yl)benzene-1,2-diamine G3 (160 mg, 63%) as an orange solid.

¹H NMR (500 MHz, CDCl₃) δ 7.04 (dd, J=7.9, 1.2 Hz, 1H), 6.97 (td, J=7.7, 1.4 Hz, 1H), 6.85-6.79 (m, 2H), 5.76 (s, 1H), 2.16 (s, 3H), 1.65 (s, 3H); LCMS (method B): 1.78 min (204.2, MH⁺).

N¹-(3-Methylisothiazol-5-yl)benzene-1,2-diamine
G5

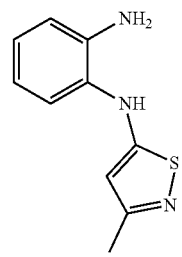

A mixture of zinc powder (556 mg, 8.50 mmol) with aqueous HCl (1M, 4 mL) was stirred for 10 min. then filtered, washed to neutrality with water then PE and dried under reduced pressure (10 min.). A mixture of 3-methyl-N-(2-nitrophenyl)isothiazol-5-amine F5 (200 mg, 0.85 mmol) and the activated zinc (556 mg, 8.50 mmol) in acetic acid (8 mL) was stirred at room temperature for 2 h. The mixture was diluted with DCM and filtered through diatomaceous earth. The filtrates were washed with saturated aq. NaHCO₃ and brine, dried (MgSO₄) and concentrated to give N¹-(3-methylisothiazol-5-yl)benzene-1,2-diamine G5 (180 mg, 100%) as a dark red viscous oil, pure enough for use directly in the next step.

¹H NMR (500 MHz, CDCl₃) δ 7.25-7.22 (m, 1H), 7.04 (dd, J=7.7, 1.3 Hz, 1H), 6.82 (t, J=7.3 Hz, 2H), 6.21 (s, 1H), 2.33 (s, 3H); LCMS (method B): 1.81 min (206.1, MH⁺).

N¹-(Isoxazol-3-yl)benzene-1,2-diamine G6

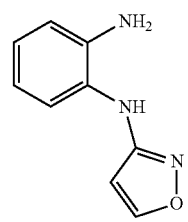 [SMILES: Nc1ccccc1Nc1ccon1]

Using the same procedure as for G3, except that the reaction time was 4 h at 60° C., N-(2-nitrophenyl)isoxazol-3-amine F6 was used as starting material instead of F3, and the product was purified by chromatography eluting with 0-100% EtOAc/PE, there was thus obtained N¹-(isoxazol-3-yl)benzene-1,2-diamine G6 (31% yield) as an orange solid.

¹H NMR (500 MHz, CDCl₃) δ 8.12 (d, J=1.6 Hz, 1H), 7.28-7.25 (m, 1H), 7.03-6.98 (m, 1H), 6.84-6.76 (m, 2H), 6.05 (s, J=17.8 Hz, 1H), 5.99 (d, J=1.8 Hz, 1H). LCMS (method B): 1.21 min (176.2, MH⁺).

$N^1$-(3-Methylpyrazin-2-yl)benzene-1,2-diamine G7

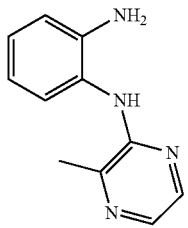

Using the same procedure as for G6, except that 3-methyl-N-(2-nitrophenyl)pyrazin-2-amine F7 was used as starting material instead of F6, and no chromatography was required following the extractive work-up, there was thus obtained $N^1$-(3-methylpyrazin-2-yl)benzene-1,2-diamine G7 (34% yield) as an orange solid.

$^1$H NMR (500 MHz, CDCl$_3$) δ 7.97 (d, J=2.7 Hz, 1H), 7.89 (d, J=2.8 Hz, 1H), 7.33 (dd, J=7.8, 1.3 Hz, 1H), 7.10 (td, J=7.8, 1.4 Hz, 1H), 6.91-6.84 (m, 2H), 6.03 (s, 1H), 2.56 (s, 3H); LCMS (method B): 1.09 min (201.1, MH$^+$).

$N^1$-(3,5-Dichloropyridin-4-yl)benzene-1,2-diamine G10

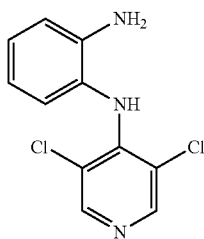 [SMILES: Nc1ccccc1Nc1c(Cl)cncc1Cl]

3,5-Dichloro-N-(2-nitrophenyl)pyridin-4-amine F10 (288 mg, 1.01 mmol) was dissolved in ethanol (5 mL). Ammonium chloride (163 mg, 3.04 mmol) was dissolved in water (0.5 mL) and added to the reaction along with iron (113 mg, 2.03 mmol). The reaction was heated at 70° C. for 18 hours. Only 40% product by LCMS so more iron (113 mg, 2.03 mmol) and a saturated solution of NH$_4$Cl (aq) (1 mL) was added and the reaction was stirred for 2 hours.

The reaction mixture was then filtered through Celite and washed with EtOAc (60 mL). The organics were washed with water (30 mL), brine, dried (MgSO$_4$) and evaporated in vacuo to give $N^1$-(3,5-dichloropyridin-4-yl)benzene-1,2-diamine G10 (225 mg, 57%) as a yellow solid.

$^1$H NMR (500 MHz, CDCl$_3$) δ 8.30 (s, 2H), 7.07 (t, J=7.7 Hz, 1H), 6.80 (d, J=8.0 Hz, 1H), 6.77 (d, J=7.6 Hz, 1H), 6.71 (t, J=7.6 Hz, 1H), 5.97 (s, 1H). LCMS (Method A): 2.43 min (220.1, MH$^+$).

5-Bromo-$N^1$-(1-methyl-1H-tetrazol-5-yl)benzene-1,2-diamine G11

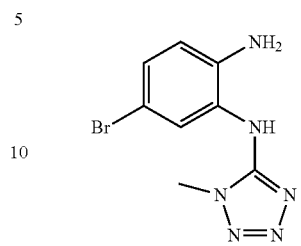

A solution of potassium carbonate (231 mg, 1.67 mmol) and sodium hydrosulfite (262 mg, 1.51 mmol) in water (2 mL) was added dropwise to a mixture of N-(5-bromo-2-nitrophenyl)-1-methyl-1H-tetrazol-5-amine F11 (100 mg, 0.334 mmol) and 1,1'-di-n-octyl-4,4'-bipyridinium dibromide (6.4 mg, 0.020 mmol) in DCM (4 mL). The mixture was stirred at 35° C. for 16 hours and quenched with water (10 mL) and extracted into DCM (2×20 mL). The organics were washed with brine, dried (MgSO$_4$) and evaporated in vacuo. The residue was chromatographed on silica, eluting with 0-10% EtOAc/PE, to give 5-bromo-$N^1$-(1-methyl-1H-tetrazol-5-yl)benzene-1,2-diamine G11 (46 mg, 51%).

$^1$H NMR (500 MHz, CDCl$_3$) δ 7.27 (d, J=9.4 Hz, 1H), 7.08 (d, J=8.0 Hz, 1H), 6.66 (d, J=8.4 Hz, 1H), 3.74 (s, 3H); LCMS (method B): 1.79 min (271.1, MH$^+$).

5-Iodo-$N^1$-(1-methyl-1H-tetrazol-5-yl)benzene-1,2-diamine G12

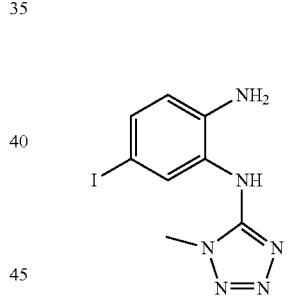

A solution of potassium carbonate (1.34 g, 9.69 mmol) and sodium hydrosulfite (1.69 g, 9.69 mmol) in water (2 mL) was added dropwise to a mixture of N-(5-iodo-2-nitrophenyl)-1-methyl-1H-tetrazol-5-amine F12 (559 mg, 1.62 mmol) and 1,1'-di-n-octyl-4,4'-bipyridinium dibromide (31 mg, 0.080 mmol) in DCE (48 mL). The mixture was stirred at 60° C. for 40 h. The reaction did not go to completion, so THF (10 mL) was added and the reaction was stirred at 60° C. for a further 24 hours. The reaction was quenched by the addition of water (50 mL), acidified with citric acid and extracted into DCM (2×50 mL). The organics were washed with brine, dried (MgSO$_4$) and evaporated in vacuo. The residue was chromatographed on silica, eluting with 20-100% EtOAc/PE to give 5-iodo-$N^1$-(1-methyl-1H-tetrazol-5-yl)benzene-1,2-diamine G12 (280 mg, 55%) as a yellow gum.

$^1$H NMR (500 MHz, CDCl$_3$) δ 7.92 (s, 1H), 7.72 (s, 1H), 7.57 (s, 1H), 6.91 (d, J=8.2 Hz, 1H), 4.19 (s, 3H), 3.74 (s, 2H); LCMS (method B): 1.93 min (317.1, MH$^+$).

3-Chloro-N[1]-(1-methyl-1H-tetrazol-5-yl)benzene-1,2-diamine G13

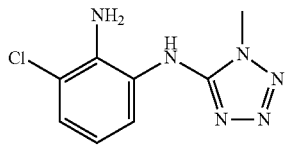

A solution of N-(3-chloro-2-nitrophenyl)-1-methyl-1H-tetrazol-5-amine F13 (2.00 g, 7.85 mmol) in MeOH (150 mL) was treated with water (50 mL), iron (1.76 g, 32.0 mmol) and ammonium chloride (2.5 g, 47 mmol) then heated under reflux for 20 hours. The mixture was cooled, filtered through Celite (and filter washed with MeOH) and concentrated. The solid was partitioned between EtOAc (100 mL; not fully soluble) and water (100 mL) and the organics washed further with water (100 mL) and brine then dried (MgSO$_4$) to give a maroon solid (0.98 g). Residual solid left in the separatory funnel after decantation of EtOAc solution was dissolved in ca. 20% MeOH/DCM, dried (MgSO$_4$) and concentrated to give an off-white solid (0.74 g). Combined this gave 3-chloro-N[1]-(1-methyl-1H-tetrazol-5-yl)benzene-1,2-diamine G13 (1.72 g, 97%); both samples identical by NMR.

$^1$H NMR (500 MHz, DMSO) δ 8.37 (s, 1H), 7.19 (dd, J=7.9, 1.4 Hz, 1H), 7.12 (dd, J=8.0, 1.4 Hz, 1H), 6.58 (t, J=8.0 Hz, 1H), 5.27 (s, 2H), 3.86 (s, 3H); LCMS (method A): 1.86 min (225.1, MH$^+$).

1-(1-Methyl-1H-tetrazol-5-yl)-1,3-dihydro-2H-benzo[d]imidazole-2-thione H

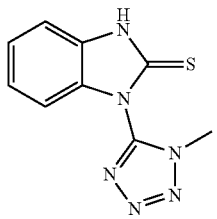 [SMILES: Cn1nnnc1-n1c(=S)[nH]c2ccccc21]

A suspension of N[1]-(1-methyl-1H-tetrazol-5-yl)benzene-1,2-diamine G (923 mg, 4.85 mmol) in dry THF (25 mL) was treated with thiocarbonyldiimidazole (1.30 g, 7.29 mmol), stirred under nitrogen at room temperature for 75 min. then diluted with water (100 mL) and cooled with ice/water. The solid was collected, washed with water and dried in vacuo to give 1-(1-methyl-1H-tetrazol-5-yl)-1,3-dihydro-2H-benzo[d]imidazole-2-thione H (962 mg, 85%) as a pale pink solid.

$^1$H NMR (500 MHz, DMSO) δ 13.66 (s, 1H), 7.36-7.29 (m, 2H), 7.29-7.20 (m, 1H), 7.10 (d, J=8.0 Hz, 1H), 4.08 (s, 3H); LCMS (method B): 1.96 min (233.1, MH$^+$).

Following the same procedure as for Synthetic Intermediate H, with the appropriate aniline starting material in place of N[1]-(1-methyl-1H-tetrazol-5-yl)benzene-1,2-diamine G, except that an extractive work-up followed by chromatography on silica was carried out if a solid was not obtained upon dilution with water, there were thus obtained the following intermediates:

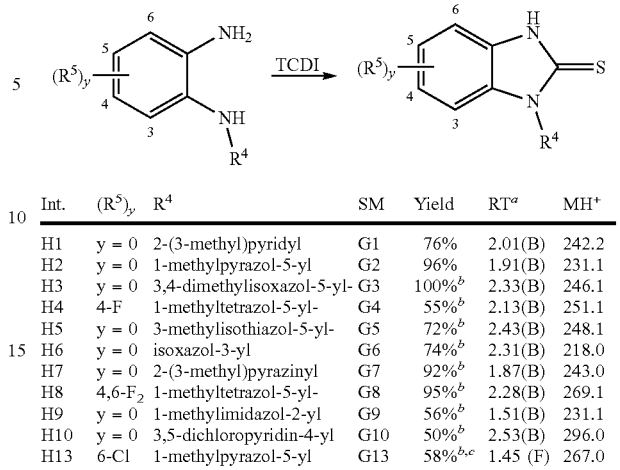

| Int. | (R$^5$)$_y$ | R$^4$ | SM | Yield | RT$^a$ | MH$^+$ |
|---|---|---|---|---|---|---|
| H1 | y = 0 | 2-(3-methyl)pyridyl | G1 | 76% | 2.01(B) | 242.2 |
| H2 | y = 0 | 1-methylpyrazol-5-yl | G2 | 96% | 1.91(B) | 231.1 |
| H3 | y = 0 | 3,4-dimethylisoxazol-5-yl- | G3 | 100%$^b$ | 2.33(B) | 246.1 |
| H4 | 4-F | 1-methyltetrazol-5-yl- | G4 | 55%$^b$ | 2.13(B) | 251.1 |
| H5 | y = 0 | 3-methylisothiazol-5-yl- | G5 | 72%$^b$ | 2.43(B) | 248.1 |
| H6 | y = 0 | isoxazol-3-yl | G6 | 74%$^b$ | 2.31(B) | 218.0 |
| H7 | y = 0 | 2-(3-methyl)pyrazinyl | G7 | 92%$^b$ | 1.87(B) | 243.0 |
| H8 | 4,6-F$_2$ | 1-methyltetrazol-5-yl- | G8 | 95%$^b$ | 2.28(B) | 269.1 |
| H9 | y = 0 | 1-methylimidazol-2-yl | G9 | 56%$^b$ | 1.51(B) | 231.1 |
| H10 | y = 0 | 3,5-dichloropyridin-4-yl | G10 | 50%$^b$ | 2.53(B) | 296.0 |
| H13 | 6-Cl | 1-methylpyrazol-5-yl | G13 | 58%$^{b,c}$ | 1.45 (F) | 267.0 |

$^a$RT = LCMS retention time in minutes using indicated Method (A-D or F);
$^b$Extractive work-up followed by chromatography;
$^c$DMF added as co-solvent and heated to 70° C. for 68 h.

6-Bromo-1-(1-methyl-1H-tetrazol-5-yl)-1,3-dihydro-2H-benzo[d]imidazole-2-thione H11

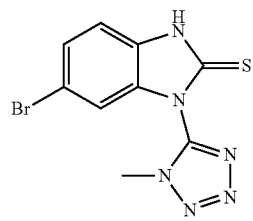 [SMILES: Cn1nnnc1-n1c(=S)[nH]c2ccc(Br)cc21]

Ethylxanthic acid potassium salt (464 mg, 2.88 mmol) was added to a solution of 5-bromo-N[1]-(1-methyl-1H-tetrazol-5-yl)benzene-1,2-diamine G11 (258 mg, 0.959 mmol) in EtOH (4 mL) and water (0.2 mL) and the reaction mixture was heated at reflux for 60 hours. The reaction mixture was diluted with water, acidified with a saturated aqueous solution of ammonium chloride and extracted into EtOAc (2×20 mL). The organics were washed with water (3×20 mL) and brine, dried (MgSO$_4$), filtered and concentrated in vacuo to give 6-bromo-1-(1-methyl-1H-tetrazol-5-yl)-1,3-dihydro-2H-benzo[d]imidazole-2-thione H11 (268 mg, 90%) as a pink solid.

1H NMR (500 MHz, CDCl3) δ 7.21 (d, J=8.5 Hz, 1H), 6.97-6.95 (m, 1H), 6.94 (s, 1H), 3.95 (s, 3H). LCMS (Method B): 2.50 mins (312.9, MH$^+$).

6-Iodo-1-(1-methyl-1H-tetrazol-5-yl)-1,3-dihydro-2H-benzo[d]imidazole-2-thione H12

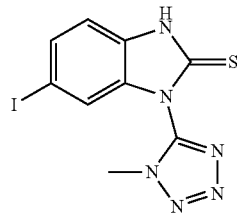 [SMILES: Cn1nnnc1-n1c(=S)[nH]c2ccc(I)cc21]

Following the same procedure as for H11, but using 5-iodo-$N^1$-(1-methyl-1H-tetrazol-5-yl)benzene-1,2-diamine G12 in place of G11, and with purification by chromatography on silica, eluting with 20-100% EtOAc/PE, the title compound H12 was obtained in 69% yield.

$^1$H NMR (500 MHz, CDCl$_3$) δ 7.49 (dd, J=8.4, 1.5 Hz, 1H), 7.22 (d, J=1.2 Hz, 1H), 6.92 (dd, J=8.4, 1.6 Hz, 1H), 4.05 (d, J=1.6 Hz, 3H); LCMS (method B): 2.56 mins, (359.0, MH$^+$).

1-(5-Chloropyrimidin-4-yl)-1,3-dihydro-2H-benzo[d]imidazole-2-thione H14

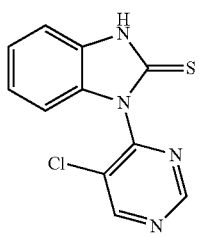 [SMILES: S=c1[nH]c2ccccc2n1-c1ncncc1Cl]

A solution of 1-(5-chloropyrimidin-4-yl)-2-(methylsulfonyl)-1H-benzo[d]imidazole T1 (24.5 mg, 0.079 mmol) in dry DMF (0.5 mL) was treated with potassium thioacetate (15 mg, 0.13 mmol) and stirred at 85° C. for 4 hours. Thiourea (22 mg, 0.29 mmol) was added and the mixture was heated to 90° C. for 6 hours then cooled, diluted with EtOAc (20 mL), washed with water (3×20 mL) and brine, dried (MgSO$_4$) and chromatographed on silica eluting with 30-40% EtOAc/PE to give 1-(5-chloropyrimidin-4-yl)-1,3-dihydro-2H-benzo[d]imidazole-2-thione H14 (8.5 mg, 41%), used directly in the next reaction.

LCMS (method B): 2.03 min (263.0, MH$^+$) purity ca. 90% by UV.

N-(4-(Chloromethyl)thiazol-2-yl)-2,2-difluoro-2-phenoxyacetamide I

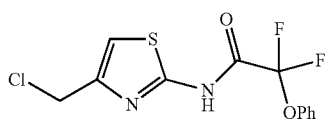 [SMILES: O=C(Nc1nc(CCl)cs1)C(F)(F)Oc1ccccc1]

N-(3-Dimethylaminopropyl)-N-ethylcarbodiimide hydrochloride (127 mg, 0.66 mmol) was added to a solution of 2,2-difluoro-2-phenoxyacetic acid (100 mg, 0.53 mmol), 4-chloromethyl-thiazol-2-ylamine hydrochloride (108 mg, 0.585 mmol) and 4-(dimethylamino)pyridine (65 mg, 0.53 mmol) in dichloromethane (4 mL) at RT and the reaction mixture was stirred for 76 hours then evaporated to dryness. The residue was redissolved in ethyl acetate (20 mL) and washed with water (3×20 mL) and brine (20 mL), dried (MgSO$_4$) and concentrated in vacuo. This crude product was purified by chromatography on silica (25 g Puriflash cartridge) eluting with 10-100% EtOAc/PE to give N-(4-(chloromethyl)thiazol-2-yl)-2,2-difluoro-2-phenoxyacetamide I (48 mg, 28%) as a colourless gum.

$^1$H NMR (500 MHz, CDCl$_3$) δ 9.75 (s, 1H), 7.45-7.38 (m, 2H), 7.34-7.29 (m, 1H), 7.25 (d, J=8.7 Hz, 2H), 7.09 (s, 1H), 4.61 (t, J=2.8 Hz, 2H); LCMS (method B): 3.08 min (319.1, MH$^+$).

4-(((tert-Butyldimethylsilyl)oxy)methyl)thiazol-2-amine J

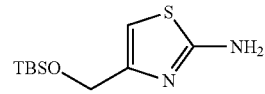

Following the procedure described for Intermediate B but using (2-aminothiazol-4-yl)methanol in place of (6-aminopyridin-2-yl)methanol and with purification by column chromatography on silica eluting with 2-40% EtOAc/PE, the title compound J was obtained in 71% yield.

$^1$H NMR (500 MHz, CDCl$_3$) δ 6.38 (s, 1H), 5.11 (s, 2H), 4.62 (br s, 2H), 0.93 (s, 9H), 0.10 (s, 6H); LCMS (method A) 3.24 min (245.2, MH$^+$).

tert-Butyl N-tert-butoxycarbonyl-N-[4-[(tert-butyl(dimethyl)silyl)oxymethyl]thiazol-2-yl]carbamate K

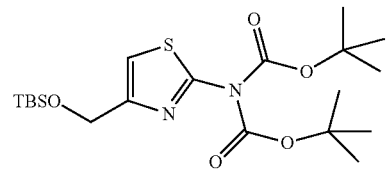 [SMILES: CC(C)(C)OC(=O)N(C(=O)OC(C)(C)C)c1nc(CO[Si](C)(C)C(C)(C)C)cs1]

4-(Dimethylamino)pyridine (0.013 g, 0.11 mmol) and di-tert-butyl dicarbonate (2.36 g, 10.8 mmol) were added to a solution of 4-(((tert-butyldimethylsilyl)oxy)methyl)thiazol-2-amine J (1.32 g, 5.42 mmol) in dichloromethane (10 mL) and the reaction mixture was stirred at RT for 18 hours. The mixture was diluted with DCM (100 mL), washed with water (50 mL) and brine (50 mL), dried (MgSO$_4$) and concentrated to give a dark yellow oil. This crude product was purified by chromatography on silica eluting with 2-18% EtOAc/PE to give the title compound K (1.0 g, 42%) as a pale yellow oil.

$^1$H NMR (500 MHz, CDCl$_3$) δ 7.02 (t, J=1.2 Hz, 1H), 4.76 (d, J=1.3 Hz, 2H), 1.50 (s, 18H), 0.93 (s, 9H), 0.10 (s, 6H); LCMS (method A): 4.36 (467.1, (M+Na$^+$).

tert-Butyl N-tert-butoxycarbonyl-N-[4-(hydroxymethyl)thiazol-2-yl]carbamate L

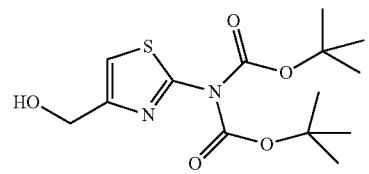 [SMILES: CC(C)(C)OC(=O)N(C(=O)OC(C)(C)C)c1nc(CO)cs1]

TBAF (1 M solution in THF) (2.17 mL, 2.17 mmol) was added to a solution of tert-butyl N-tert-butoxycarbonyl-N-[4-[(tert-butyl(dimethyl)silyl)oxymethyl]thiazol-2-yl]carbamate K (0.877 g, 1.97 mmol) in THF (10 mL) at 0° C. and the reaction mixture was stirred at 0° C. for 4 hours then allowed to warm to RT over 16 hours. The mixture was diluted with EtOAc (20 mL), washed with water (20 mL)

and brine (20 mL), dried (MgSO$_4$) and concentrated to give the title compound L (0.456 g, 70%) as a pale green oil, used without further purification.

$^1$H NMR (500 MHz, CDCl$_3$) δ 6.99 (t, J=0.9 Hz, 1H), 4.68 (d, J=0.9 Hz, 2H), 1.52 (s, 18H); LCMS (method A): 2.88 min (331, MH$^+$).

tert-Butyl (4-(hydroxymethyl)thiazol-2-yl)carbamate M

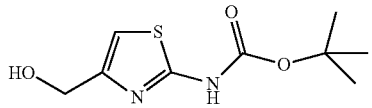

A solution of tert-butyl N-tert-butoxycarbonyl-N-[4-(hydroxymethyl)thiazol-2-yl]carbamate L (111 mg, 0.336 mmol) in THF (8 mL) was treated with a solution of lithium hydroxide monohydrate (28.2 mg, 0.672 mmol) in water (2 mL) and methanol (2 mL). The mixture was stirred at 50° C. for 90 minutes then treated with saturated aqueous ammonium chloride solution (to pH 8), diluted with ethyl acetate (20 mL), washed with water (3×20 mL) and brine (20 mL), dried (MgSO$_4$) and chromatographed on silica (12 g Puriflash cartridge) eluting with 10-100% EtOAc/PE to give the title compound M (41 mg, 53%) as a colourless oil.

$^1$H NMR (500 MHz, CDCl$_3$) δ 6.76 (s, 1H), 4.59 (s, 2H), 1.56 (s, 9H); LCMS (method A): 2.05 min (229.2, (M-H)$^-$).

tert-Butyl (4-(bromomethyl)thiazol-2-yl)carbamate N

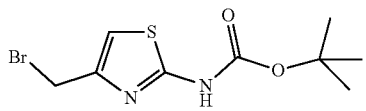

A solution of tert-butyl (4-(hydroxymethyl)thiazol-2-yl)carbamate M (37 mg, 0.16 mmol) in DCM (2 mL) was treated with triphenylphosphine (44.3 mg, 0.169 mmol) and carbon tetrabromide (55.9 mg, 0.169 mmol). The reaction mixture was stirred at RT for 16 hours then concentrated in vacuo and purified by chromatography on silica (12 g Puriflash cartridge) eluting with 10-100% EtOAc/PE to give the title compound N (19 mg, 40%) as a colourless gum.

$^1$H NMR (500 MHz, CDCl$_3$) δ 9.48 (s, 1H), 6.88 (s, 1H), 4.51 (s, 2H), 1.55 (s, 9H); LCMS (method F): 1.85 min (295.0, MH$^+$).

2-(6-(((1-Methyl-1H-tetrazol-5-yl)-1H-benzo[d]imidazol-2-yl)thio)methyl)pyridin-2-yl)isoindoline-1,3-dione O

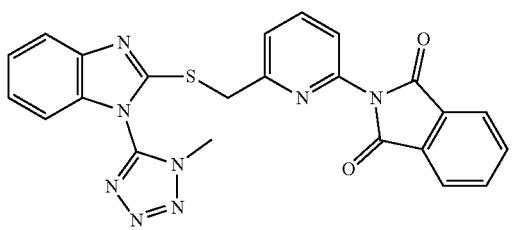 [SMILES: Cn1nnnc1-n1c(SCc2cccc(N3C(=O)c4ccccc4C3=O)n2)nc2ccccc21]

Using the method described in Example 1, substituting the halide E with 2-(6-(bromomethyl)pyridin-2-yl)isoindoline-1,3-dione (prepared as described in J. Med. Chem., 2007, 50, 1124), there was thus obtained the title compound O in 70% yield (triturated with Et$_2$O after chromatographic purification).

$^1$H NMR (500 MHz, CDCl$_3$) δ 7.96 (dd, J=5.5, 3.0 Hz, 2H), 7.88-7.79 (m, 3H), 7.78 (d, J=8.0 Hz, 1H), 7.62 (d, J=7.7 Hz, 1H), 7.36 (td, J=7.8, 1.1 Hz, 1H), 7.33-7.27 (m, 2H), 7.05 (d, J=8.0 Hz, 1H), 4.80 (s, 2H), 3.86 (s, 3H); LCMS (method B): 2.78 min (469.2, MH$^+$).

(6-(2,2-Difluoro-2-phenoxyacetamido)pyridin-2-yl)methyl methanesulfonate P

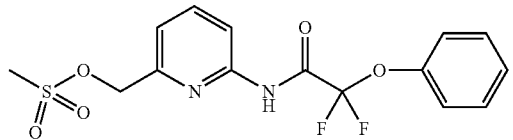 [SMILES: CS(=O)(=O)OCc1cccc(NC(=O)C(F)(F)Oc2ccccc2)n1]

An ice-cooled solution of 2,2-difluoro-N-(6-(hydroxymethyl)pyridin-2-yl)-2-phenoxyacetamide D (108 mg, 0.37 mmol) in DCM (1 mL) was treated with methanesulfonyl chloride (0.030 mL, 0.39 mmol) then triethylamine (0.054 ml, 0.39 mmol) and stirred for 40 min. The mixture was diluted with DCM (20 mL), washed with water (20 mL) and brine, dried (MgSO$_4$) and chromatographed on silica (12 g Puriflash cartridge) eluting with 30-50% EtOAc/PE to give (6-(2,2-difluoro-2-phenoxyacetamido)pyridin-2-yl)methyl methanesulfonate P (132 mg, 77%) as a colourless gum.

$^1$H NMR (500 MHz, CDCl$_3$) δ 8.78 (s, 1H), 8.25 (d, J=8.3 Hz, 1H), 7.86 (t, J=7.9 Hz, 1H), 7.45-7.37 (m, 2H), 7.32 (t, J=4.8 Hz, 1H), 7.31-7.26 (m, 3H), 5.24 (s, 2H), 3.08 (s, 3H); LCMS (method B): 2.95 min (373.1, MH$^+$)

Following the same procedure as for Synthetic Intermediate ("Int.") P, substituting 2,2-difluoro-N-(6-(hydroxymethyl)pyridin-2-yl)-2-phenoxyacetamide starting material ("SM") D with the required alcohol, there were thus obtained the following mesylated intermediates P1-P10:

| Int. | R⌒OH | Yield | RT$^a$ | MH$^+$ |
|---|---|---|---|---|
| P1[b] | D1 | 100% | 1.40 (B) | 271.2 |
| P2 | D2 | 50% | 2.82 (B) | 337.1 |
| P3[b] | D3 | 91% | 1.87 (B) | 259.1 |
| P4[b] | 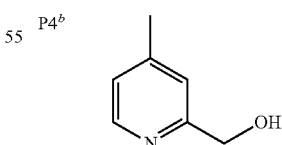 | 75% | 1.20 (B) | 202.2 |
| P5[b] | 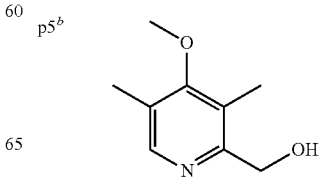 | 90% | 1.44 (B) | 246.1 |

-continued

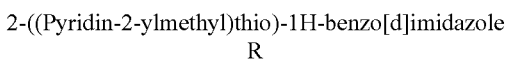

| Int. | R-OH | Yield | RT[a] | MH+ |
|---|---|---|---|---|
| P6[b] | | 100% | 1.28 (B) | 248.2 |
| P7[b] | | 96% | 1.50 (B) | 290.1 |
| P8[b] | | 100% | 2.05 (B) | 300.1 |
| P9[b] | | 100% | 0.96 (B) | 218.1 |
| P10[b] | | 80% | 1.04 (B) | 189.1 |

[a]RT = LCMS retention time in minutes using indicated Method (A-D or F);
[b]Product used directly in next step without need for chromatographic purification.

Pyridin-2-ylmethyl 4-methylbenzenesulfonate Q

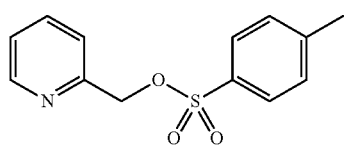 [SMILES: Cc1ccc(S(=O)(=O)OCc2ccccn2)cc1]

Powdered potassium hydroxide (1.74 g, 31.0 mmol) was added to an ice-cooled solution of 2-pyridylcarbinol (2.0 mL, 21 mmol) in THF (100 mL). The mixture was stirred vigorously for 30 minutes then treated with 4-toluenesulfonyl chloride (5.14 g, 26.9 mmol). The reaction mixture was allowed to slowly warm to RT and stirred for 5 hours at RT. The reaction was quenched by the addition of a saturated aqueous solution of sodium hydrogen carbonate (80 mL) and extracted with EtOAc (3×50 mL). The organics were washed with brine, dried (MgSO$_4$) and concentrated in vacuo. The crude residue was chromatographed on silica, eluting with 20-40% EtOAc/PE to give pyridin-2-ylmethyl 4-methylbenzenesulfonate Q (4.36 g, 80%) as a pale orange solid.

$^1$H NMR (500 MHz, CDCl$_3$) δ 8.52 (d, J=4.7 Hz, 1H), 7.84 (d, J=8.3 Hz, 2H), 7.71 (td, J=7.7, 1.6 Hz, 1H), 7.43 (d, J=7.8 Hz, 1H), 7.34 (d, J=8.1 Hz, 2H), 7.23 (dd, J=7.2, 5.0 Hz, 1H), 5.14 (s, 2H), 2.45 (s, 3H); LCMS (method B): 2.54 min (264.2, MH+).

2-((Pyridin-2-ylmethyl)thio)-1H-benzo[d]imidazole R

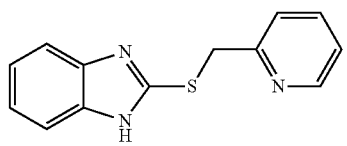 [SMILES: c1ccc(CSc2nc3ccccc3[nH]2)nc1]

A solution of 2-mercaptobenzimidazole (3.06 g, 20.4 mmol) in DMF (18 mL) was treated with 2-(chloromethyl)pyridine hydrochloride (3.51 g, 21.4 mmol) and caesium carbonate (15.2 g, 46.7 mmol) and stirred at RT for 4 hours then diluted with EtOAc (150 mL), washed with water (3×150 mL) and brine, dried (MgSO$_4$) and concentrated to give 2-((pyridin-2-ylmethyl)thio)-1H-benzo[d]imidazole R (4.63 g, 94%) as an off-white solid.

$^1$H NMR (500 MHz, CDCl$_3$) δ 8.66 (ddd, J=4.9, 1.7, 0.9 Hz, 1H), 7.77 (td, J=7.7, 1.8 Hz, 1H), 7.61-7.55 (m, 2H), 7.44-7.39 (m, 1H), 7.33 (ddd, J=7.6, 4.9, 1.1 Hz, 1H), 7.25-7.19 (m, 2H), 4.41 (s, 2H); LCMS (method B): 1.54 min (242.1, MH+).

1-(1-Methyl-1H-tetrazol-5-yl)-2-(methylthio)-1H-benzo[d]imidazole S

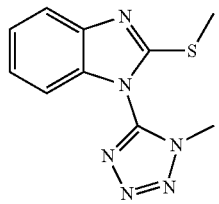 [SMILES: CSc1nc2ccccc2n1-c1nnnn1C]

A solution of 1-(1-methyl-1H-tetrazol-5-yl)-1,3-dihydro-2H-benzo[d]imidazole-2-thione H (373 mg, 1.61 mmol) in dry DMF (3 mL) was treated with iodomethane (0.113 mL, 1.82 mmol) then caesium carbonate (740 mg, 2.27 mmol) and the mixture was stirred at RT under nitrogen for 40 min. The solution was diluted with water (20 mL) and extracted with EtOAc (25 mL). The organics were washed further with water (2×25 mL) and brine, dried (MgSO$_4$) and chromatographed on silica, eluting with 0-1% MeOH/DCM, to give 1-(1-methyl-1H-tetrazol-5-yl)-2-(methylthio)-1H-benzo[d]imidazole S (341 mg, 86%) as a red solid.

$^1$H NMR (500 MHz, CDCl$_3$) δ 7.75 (d, J=8.0 Hz, 1H), 7.39-7.32 (m, 1H), 7.30-7.21 (m, 1H), 7.04 (d, J=8.0 Hz, 1H), 3.98 (s, 3H), 2.81 (s, 3H); LCMS (method B) 2.35 min (247.1, MH+).

1-(5-Chloropyrimidin-4-yl)-2-(methylthio)-1H-benzo[d]imidazole S1

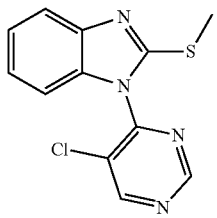 [SMILES: CSc1nc2ccccc2n1-c1ncncc1Cl]

A stirred solution of 4,5-dichloropyrimidine (206 mg, 1.38 mmol) and 2-methylthiobenzimidazole (227 mg, 1.38 mmol) in dry DMF (1.5 mL) was treated with potassium tert-butoxide (155 mg, 1.38 mmol) then heated to 50° C. for 8 hours. The solution was cooled, quenched with saturated aq. ammonium chloride solution (to pH 6-7), diluted with water (30 mL) and extracted with EtOAc (40 mL). The organics were washed with water (2×30 mL) and brine, dried (MgSO$_4$), triturated with DCM and the liquors were chromatographed eluting with 20-50% EtOAc/PE to give 1-(5-chloropyrimidin-4-yl)-2-(methylthio)-1H-benzo[d]imidazole S1 (193 mg, 50%) as a colourless gum.

$^1$H NMR (500 MHz, CDCl$_3$) δ 9.20 (s, 1H), 9.01 (s, 1H), 7.78-7.71 (m, 1H), 7.30 (ddd, J=8.1, 7.4, 1.1 Hz, 1H), 7.22 (ddd, J=8.4, 7.4, 1.1 Hz, 1H), 7.08-7.01 (m, 1H), 2.79 (s, 3H); LCMS (method B): 2.58 min (277.0, MH$^+$).

1-(1-Methyl-1H-tetrazol-5-yl)-2-(methylsulfonyl)-1H-benzo[d]imidazole T

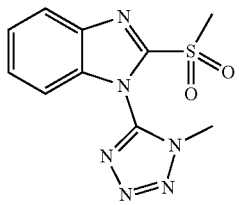 [SMILES: Cn1nnnc1-n1c(S(C)(=O)=O)nc2ccccc21]

An ice-cooled solution of 1-(1-methyl-1H-tetrazol-5-yl)-2-(methylthio)-1H-benzo[d]imidazole S (4.55 g, 18.5 mmol) in DCM (100 mL) was treated with 75% 3-chloroperbenzoic acid (10.6 g, 46.2 mmol), stirred for 10 min then cooling was removed. After a further 4 hours the mixture was filtered and the solid washed with DCM. The filtrates were combined, washed with saturated aq. sodium hydrogen carbonate solution (2×100 mL) and brine and the aq. back-extracted with DCM (100 mL). The organics were dried (MgSO$_4$) and chromatographed on silica, eluting with 25-50% EtOAc/PE, to give 1-(1-methyl-1H-tetrazol-5-yl)-2-(methylsulfonyl)-1H-benzo[d]imidazole T (4.39 g, 85%) as a white solid.

$^1$H NMR (500 MHz, CDCl$_3$) δ 8.04 (ddd, J=4.1, 2.9, 0.7 Hz, 1H), 7.65-7.50 (m, 2H), 7.15 (ddd, J=4.9, 2.9, 0.7 Hz, 1H), 4.00 (s, 3H), 3.43 (s, 3H); LCMS (method B): 2.07 min (279.1, MH$^+$).

1-(5-Chloropyrimidin-4-yl)-2-(methylsulfonyl)-1H-benzo[d]imidazole T1

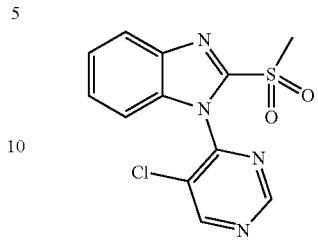

Following the same procedure as for T, but using 1-(5-chloropyrimidin-4-yl)-2-(methylthio)-1H-benzo[d]imidazole S1 in place of sulfide S, there was thus obtained the title compound T1 in 83% yield as a white solid.

$^1$H NMR (500 MHz, CDCl$_3$) δ 9.21 (s, 1H), 9.06 (s, 1H), 8.08-7.93 (m, 1H), 7.59-7.46 (m, 2H), 7.19-7.08 (m, 1H), 3.49 (s, 3H); LCMS (method B): 2.33 min (309.0, MH$^+$).

1-(1-Methyl-1H-tetrazol-5-yl)-2-((pyridin-2-ylmethyl)thio)-6-((trimethylsilyl)ethynyl)-1H-benzo[d]imidazole U

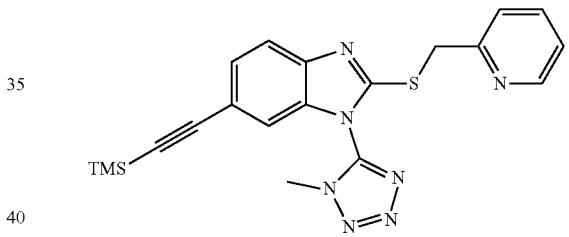

A suspension of copper (I) iodide (0.138 mg, 0.726 μmol) and bis(triphenylphosphine) palladium(II) dichloride (0.255 mg, 0.363 μmol) in dry triethylamine (1 mL, 7 mmol) was evacuated and backfilled with nitrogen 3 times. A solution of 6-iodo-1-(1-methyl-1H-tetrazol-5-yl)-2-((pyridin-2-ylmethyl)thio)-1H-benzo[d]imidazole Example 54 (16 mg, 0.04 mmol) in dry triethylamine (0.5 mL) was added followed by trimethylsilylacetylene (5 μL, 0.04 mmol) and the reaction mixture was stirred at RT for 24 hours. The reaction mixture was diluted with EtOAc (20 mL) and washed with saturated aqueous ammonium chloride solution (10 mL), water (10 mL), brine, then dried (MgSO$_4$), and concentrated in vacuo. The residue was chromatographed on silica, eluting with 0-100% EtOAc/PE to give 1-(1-methyl-1H-tetrazol-5-yl)-2-((pyridin-2-ylmethyl)thio)-6-((trimethylsilyl)ethynyl)-1H-benzo[d]imidazole U (21 mg, 100%) as a brown gum.

$^1$H NMR (500 MHz, CDCl$_3$) δ 8.53 (s, 1H), 7.66 (d, J=6.6 Hz, 2H), 7.51-7.43 (m, 2H), 7.20 (d, J=9.5 Hz, 1H), 7.15 (s, 1H), 4.78 (s, 2H), 3.92 (s, 3H), 0.22 (s, 9H); LCMS (method B): 3.56 min (420.3, MH$^+$).

2,2-Difluoro-N-(6-((((6-iodo-1-(1-methyl-1H-tetrazol-5-yl)-1H-benzo[d]imidazol-2-yl)thio)methyl)pyridin-2-yl)-2-phenoxyacetamide U1

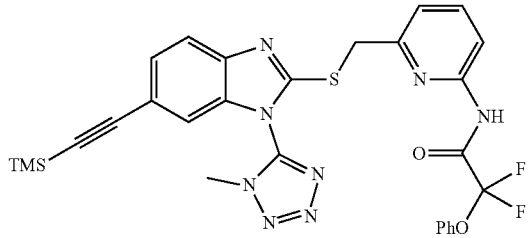 [SMILES: Cn1nnnc1-n1c(SCc2cccc(NC(=O)C(F)(F)Oc3ccccc3)n2)nc2ccc(C#C[Si](C)(C)C)cc21]

Following the same procedure as for Int. U, but using Example 44 as starting material in place of Example 54, there was thus obtained 2,2-difluoro-N-(6-(((6-iodo-1-(1-methyl-1H-tetrazol-5-yl)-1H-benzo[d]imidazol-2-yl)thio)methyl)pyridin-2-yl)-2-phenoxyacetamide U1 in a 37% yield.

$^1$H NMR (500 MHz, CDCl$_3$) δ 8.86 (s, 1H), 8.15 (d, J=7.8 Hz, 1H), 7.74 (t, J=7.8 Hz, 1H), 7.67 (d, J=8.1 Hz, 1H), 7.46 (d, J=7.4 Hz, 1H), 7.41 (t, J=7.9 Hz, 2H), 7.29 (t, J=8.8 Hz, 4H), 7.15 (s, 1H), 4.67 (s, 2H), 3.93 (s, 3H), 0.23 (s, 9H); LCMS (method B): 4.13 min (635.2, MH$^+$).

Following the same procedure as for Synthetic Intermediate ("Int.") F, substituting 1-fluoro-2-nitrobenzene and/or 5-amino-1-methyltetrazole with the required o-fluoronitrobenzene (optionally substituted with (R$^5$)$_y$) and/or aminoheterocycle (R$^4$—NH$_2$), and generally with all of the NaH added at the start of the reaction, there were thus obtained the following intermediates:

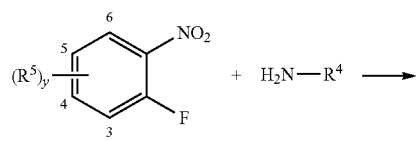

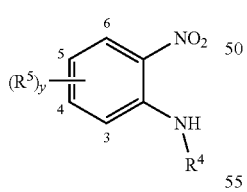

| Int. | (R$^5$)$_y$ | R$^4$—NH$_2$ | Yield | RT$^a$ | MH$^+$ |
|---|---|---|---|---|---|
| F14 | 5-Cl | 5-amino-1-methyltetrazole | 27% | 2.88 (B) | 255.1 |
| F15 | 3-Cl | 5-amino-1-methyltetrazole | 89%$^b$ | 2.17 (B) | 255.1 |
| F16$^c$ | 6-MeO,4-F | 5-amino-1-methyltetrazole | 87% | 2.62 (B) | 269.1 |

$^a$RT = LCMS retention time in minutes using indicated Method (A-D or F);
$^b$Yield after correction for 30% water content in bulk after drying a small sample.
$^c$Product obtained using an aqueous work-up, extracting with EtOAc; no further purification was required.

4-Chloro-N$^1$-(1-methyl-1H-tetrazol-5-yl)benzene-1,2-diamine G14

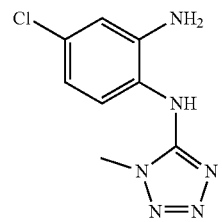

Following the same procedure as for G12, but using N-(4-chloro-2-nitrophenyl)-1-methyl-1H-tetrazol-5-amine F14 in place of F12, the title compound G14 was obtained in 97% yield as a brown gum.

$^1$H NMR (500 MHz, CDCl$_3$) δ 7.10 (d, J=8.4 Hz, 1H), 6.82 (d, J=17.6 Hz, 1H), 6.77-6.71 (m, 2H), 3.73 (s, J=3.4 Hz, 2H), 3.72 (s, J=9.1 Hz, 3H); LCMS (method B): 1.97 min (225.1, MH$^+$).

6-Chloro-N$^1$-(1-methyl-1H-tetrazol-5-yl)benzene-1,2-diamine G15

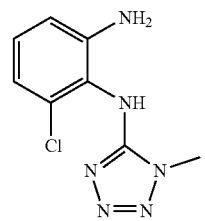

Following the same procedure as for G13, but using N-(4-chloro-2-nitrophenyl)-1-methyl-1H-tetrazol-5-amine F15 (containing 30% water by weight) in place of F13, and a simple extractive work-up sufficed following filtration through Celite since the product was more soluble in EtOAc, the title compound G15 was obtained in 95% yield as a beige solid.

$^1$H NMR (500 MHz, DMSO) δ 8.41 (s, 1H), 6.99 (t, J=8.0 Hz, 1H), 6.67 (dd, J=8.2, 1.3 Hz, 1H), 6.62 (dd, J=7.9, 1.3 Hz, 1H), 5.45 (s, 2H), 3.83 (s, 3H); LCMS (method B): 1.76 min (225.1, MH$^+$).

5-Fluoro-3-methoxy-N$^1$-(1-methyl-1H-tetrazol-5-yl)benzene-1,2-diamine G16

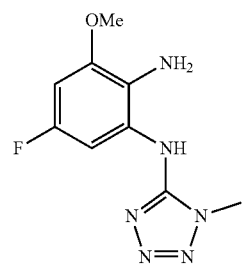 [SMILES: COc1cc(F)cc(Nc2nnnn2C)c1N]

Following the same procedure as for G, but using N-(5-fluoro-3-methoxy-2-nitrophenyl)-1-methyl-1H-tetrazol-5-amine F16 in place of F, and the filtrate was concentrated until precipitation commenced then cooled in ice-water, filtered, washed with cold ethanol, and dried, the title compound G16 was obtained as an off-white solid in 47% yield.

$^1$H NMR (500 MHz, DMSO) δ 6.91 (dd, J=10.6, 2.8 Hz, 1H), 6.66 (dd, J=10.5, 2.8 Hz, 1H), 4.50 (br s, 2H), 3.88 (s, 3H), 3.81 (s, 3H); LCMS (method B): 1.72 min (239.1, MH$^+$).

5-Chloro-1-(1-methyl-1H-tetrazol-5-yl)-1,3-dihydro-2H-benzo[d]imidazole-2-thione H15

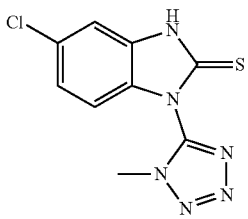 [SMILES: Cn1nnnc1-n1c(=S)[nH]c2cc(Cl)ccc21]

Following the same procedure as for H11, but using 4-chloro-N$^1$-(1-methyl-1H-tetrazol-5-yl)benzene-1,2-diamine G14 in place of G11, and with purification by chromatography on silica, eluting with 20-100% EtOAc/PE, the title compound H15 was obtained as a brown solid in 68% yield.

$^1$H NMR (500 MHz, CDCl$_3$) δ 10.13 (s, 1H), 7.33-7.30 (m, 1H), 7.24-7.22 (m, 1H), 6.98 (d, J=8.5 Hz, 1H), 4.17 (s, 3H). LCMS (method A): 1.61 min (267.0, MH$^+$)

7-Chloro-1-(1-methyl-1H-tetrazol-5-yl)-1,3-dihydro-2H-benzo[d]imidazole-2-thione H16

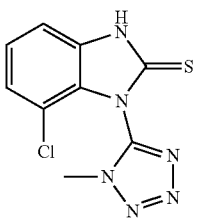 [SMILES: Cn1nnnc1-n1c(=S)[nH]c2cccc(Cl)c21]

A solution of 6-chloro-N$^1$-(1-methyl-1H-tetrazol-5-yl)benzene-1,2-diamine G15 (453 mg, 2.02 mmol) in dry DMF (3 mL) was treated with thiocarbonyldiimidazole (457 mg, 2.56 mmol), stirred under nitrogen at 90° C. for 5 h then cooled, diluted with EtOAc (40 mL) washed with water (3×40 mL) and brine then dried (MgSO$_4$) to give 7-chloro-1-(1-methyl-1H-tetrazol-5-yl)-1,3-dihydro-2H-benzo[d]imidazole-2-thione H16 (502 mg, 93%) as an olive-green solid.

$^1$H NMR (500 MHz, DMSO) δ 13.96 (s, 1H), 7.38-7.27 (m, 3H), 4.07 (s, 3H); LCMS (method B): 2.55 min (267.1, MH$^+$).

6-Fluoro-4-methoxy-1-(1-methyl-1H-tetrazol-5-yl)-1,3-dihydro-2H-benzo[d]imidazole-2-thione H17

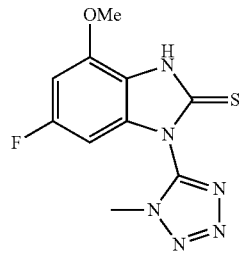 [SMILES: COc1cc(F)cc2c1[nH]c(=S)n2-c1nnnn1C]

Following the same procedure as for H16, but using 5-fluoro-3-methoxy-N$^1$-(1-methyl-1H-tetrazol-5-yl)benzene-1,2-diamine G16 in place of G15 and without the need for chromatographic purification, the title compound H17 was obtained as a pale orange solid in 89% yield.

$^1$H NMR (500 MHz, DMSO) δ 13.93 (s, 1H), 6.98 (dd, J=11.9, 2.2 Hz, 1H), 6.67 (dd, J=8.3, 2.2 Hz, 1H), 4.05 (s, 3H), 3.95 (s, 3H); LCMS (method B): 2.42 min (281.1, MH$^+$).

tert-Butyl N-[(tert-butoxy)carbonyl]-N-(6-{[(tert-butyldimethylsilyl)oxy]methyl}pyridin-2-yl)carbamate K1

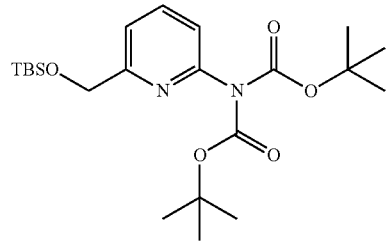 [SMILES: CC(C)(C)OC(=O)N(C(=O)OC(C)(C)C)c1cccc(CO[Si](C)(C)C(C)(C)C)n1]

Following the same procedure as for Int. K, but using 6-(((tert-butyldimethylsilyl)oxy)methyl)pyridin-2-amine B instead of J, the title compound K1 was obtained as a yellow oil in 85% yield.

$^1$H NMR (500 MHz, CDCl$_3$) δ 7.74 (t, J=7.8 Hz, 1H), 7.43 (dd, J=7.7, 0.7 Hz, 1H), 7.08 (dd, J=7.8, 0.5 Hz, 1H), 4.79 (s, 2H), 1.42 (s, 18H), 0.95 (s, 9H), 0.11 (d, J=1.6 Hz, 6H); LCMS (method A): 4.04 min (439.3, MH$^+$).

tert-Butyl N-[(tert-butoxy)carbonyl]-N-[6-(hydroxymethyl)pyridin-2-yl]carbamate L1

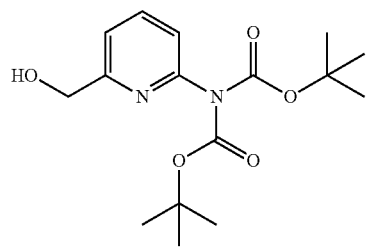 [SMILES: CC(C)(C)OC(=O)N(C(=O)OC(C)(C)C)c1cccc(CO)n1]

Following the same procedure as for Int. L, but using tert-butyl N-[(tert-butoxy)carbonyl]-N-(6-{[(tert-butyldimethylsilyl)oxy]methyl}pyridin-2-yl)carbamate K1 in place of K, the title compound L1 was obtained by trituration with petroleum ether as a white solid in 70% yield.

$^{1}$H NMR (500 MHz, CDCl$_{3}$) δ 7.78-7.73 (m, 1H), 7.19 (d, J=8.0 Hz, 1H), 7.15 (dd, J=7.6, 0.6 Hz, 1H), 4.74 (s, 2H), 1.45 (s, 18H); LCMS (method B): 2.65 min (225.1, [M-Boc+H]$^{+}$)

tert-Butyl (6-(hydroxymethyl)pyridin-2-yl)carbamate M1

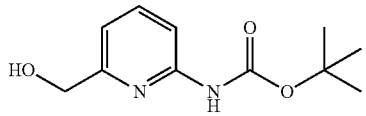 [SMILES: CC(C)(C)OC(=O)Nc1cccc(CO)n1]

Following the same procedure as for Int. M, but using tert-butyl N-[(tert-butoxy)carbonyl]-N-[6-(hydroxymethyl)pyridin-2-yl]carbamate L1 in place of L, the title compound M1 was obtained as a colourless oil in 84% yield.

$^{1}$H NMR (500 MHz, CDCl$_{3}$) δ 7.82 (d, J=8.3 Hz, 1H), 7.68-7.61 (m, 1H), 7.33 (br s, 1H), 6.89 (dd, J=7.5, 0.6 Hz, 1H), 4.64 (s, 2H), 3.51 (br s, 1H), 1.52 (s, 9H); LCMS (method A) 2.29 min (No product mass).

2-(6-(((4-Chloro-1-(1-methyl-1H-tetrazol-5-yl)-1H-benzo[d]imidazol-2-yl)thio)methyl)pyridin-2-yl)isoindoline-1,3-dione O1

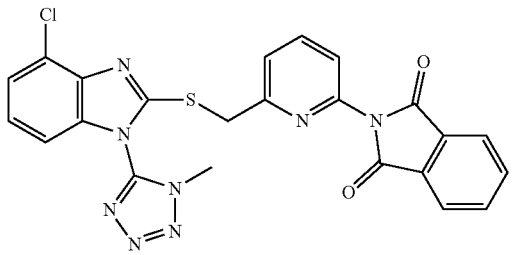 [SMILES: Cn1nnnc1-n1c(SCc2cccc(N3C(=O)c4ccccc4C3=O)n2)nc2c(Cl)cccc21]

Following the method described in Example 86, using 2-(6-(bromomethyl)pyridin-2-yl)isoindoline-1,3-dione in place of P18, there was thus obtained 6-(((4-chloro-1-(1-methyl-1H-tetrazol-5-yl)-1H-benzo[d]imidazol-2-yl)thio)methyl)pyridin-2-amine O1 in quantitative yield. LCMS (method B): 3.51 min (503.1, MH$^{+}$).

Following the same procedure as for Synthetic Intermediate ("Int.") P, substituting 2,2-difluoro-N-(6-(hydroxymethyl)pyridin-2-yl)-2-phenoxyacetamide starting material ("SM") D with the required alcohol, there were thus obtained the following mesylated intermediates P11-P18:

| Int. | R  | Yield | RT$^{a}$ | MH$^{+}$ |
|---|---|---|---|---|
| P11$^{b}$ | 4-methoxy-pyridin-2-yl-methanol | 100% | 2.19 (A) | 218.1 |
| P12$^{b}$ | 5-methyl-pyridin-2-yl-methanol | 100% | 1.81 (B) | 202.1 |
| P13$^{b}$ | 4-cyano-pyridin-2-yl-methanol | 100% | 2.07 (B) | 213.1 |
| P14$^{b}$ | 5-methoxy-pyridin-2-yl-methanol | 100% | 1.91 (B) | 218.1 |
| P15$^{b}$ | 5-bromo-pyridin-2-yl-methanol | 100% | 2.57 (B) | 268.0 |
| P16$^{b}$ | 3,5-dichloro-pyridin-2-yl-methanol | 100% | 2.69 (B) | 256.0 |
| P17$^{b}$ | 4-trifluoromethyl-pyridin-2-yl-methanol | 100% | 2.71 (B) | 256.0 |
| P18$^{b}$ | M1 | 90% | 3.01 (B) | 303.1 |

$^{a}$RT = LCMS retention time in minutes using indicated Method (A-D or F);
$^{b}$Product used directly in next step without need for chromatographic purification.

Example 1—2,2-Difluoro-N-(6-(((1-(1-methyl-1H-tetrazol-5-yl)-1H-benzo[d]imidazol-2-yl)thio)methyl)pyridin-2-yl)-2-phenoxyacetamide 1

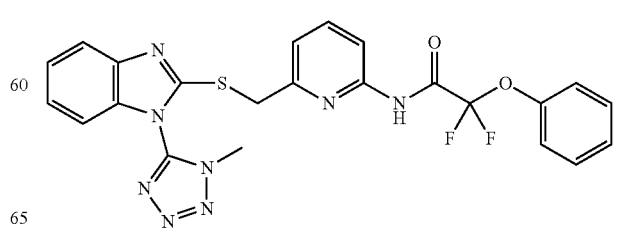

A solution of 1-(1-methyl-1H-tetrazol-5-yl)-1,3-dihydro-2H-benzo[d]imidazole-2-thione H (26 mg, 0.11 mmol) in dry DMF (1 mL) was treated with a solution of N-(6-(bromomethyl)pyridin-2-yl)-2,2-difluoro-2-phenoxyacetamide E (49 mg, 0.14 mmol) in dry THF (0.7 mL) and caesium carbonate (60 mg, 0.18 mmol) was added. The mixture was stirred at RT for 100 min then diluted with EtOAc (20 mL), washed with water (3×20 mL) and brine, dried (MgSO$_4$) and chromatographed on silica (4 g Puriflash cartridge) eluting with 0-50% EtOAc/PE to give 2,2-difluoro-N-(6-(((1-(1-methyl-1H-tetrazol-5-yl)-1H-benzo[d]imidazol-2-yl)thio)methyl)pyridin-2-yl)-2-phenoxyacetamide 1 (48 mg, 84%) as a colourless gum.

$^1$H NMR (500 MHz, CDCl$_3$) δ 8.90 (s, 1H), 8.13 (d, J=8.3 Hz, 1H), 7.77 (d, J=8.0 Hz, 1H), 7.74-7.68 (m, 1H), 7.45-7.33 (m, 3H), 7.32-7.26 (m, 5H), 7.07-7.00 (m, 1H), 4.67 (s, 2H), 3.92 (s, 3H); LCMS (method B): 3.28 min (509, MH$^+$).

Using the method described in Example 1, substituting either or both of the halide E or the benzimidazol-2-thione derivative H with the appropriate building block, and with additional base if "E" was a salt, and DMF was generally used as solvent in place of THF, there were thus obtained the following Examples (thioethers, Ex. 2-25):

"E" + "H" $\xrightarrow{Cs_2CO_3, DMF}$ Thioether

| Ex. | "E" | "H" | Yield | $^1$H NMR δ(CDCl$_3$) | RT$^a$ | Structure |
|---|---|---|---|---|---|---|
| 2 | 2-(chloromethyl)pyridine·HCl | H | 34% | 8.56-8.49 (m, 1H), 7.77 (d, J = 8.0 Hz, 1H), 7.64 (td, J = 7.7, 1.8 Hz, 1H), 7.47 (d, J = 7.8 Hz, 1H), 7.36 (td, J = 7.8, 1.1 Hz, 1H), 7.28 (dd, J = 8.1, 1.0 Hz, 1H), 7.22-7.15 (m, 1H), 7.04 (d, J = 8.0 Hz, 1H), 4.78 (s, 2H), 3.91 (s, 3H). | 5.68 (D) | benzimidazole-tetrazole-S-CH$_2$-pyridine |
| 3 | 4-(chloromethyl)-2-aminothiazole·HCl | H | 46% | 7.77 (d, J = 8.0 Hz, 1H), 7.36 (td, J = 7.9, 1.1 Hz, 1H), 7.32-7.20 (m, 1H) 7.05 (d, J = 8.0 Hz, 1H), 6.46 (s, 1H), 5.21 (br s, 2H), 4.49 (s, 2H), 3.89 (s, 3H) | 6.15 (C) | benzimidazole-tetrazole-S-CH$_2$-(2-aminothiazole) |
| 4 | E | H1 | 60% | 8.91 (s, 1H), 8.53 (ddd, J = 4.7, 1.8, 0.5 Hz, 1H), 8.09 (d, J = 8.2 Hz, 1H), 7.78 (ddd, J = 7.7, 1.8, 0.7 Hz, 1H), 7.77-7.74 (m, 1H), 7.68 (t, J = 7.9 Hz, 1H), 7.43-7.36 (m, 3H), 7.32 (d, J = 7.6 Hz, 1H), 7.30-7.26 (m, 3H), 7.25-7.23 (m, 1H), 7.19-7.14 (m, 1H), 6.95-6.89 (m, 1H), 4.68 (s, 2H), 2.06 (s, 3H) | 9.14 (D) | benzimidazole-(methylpyridyl)-S-CH$_2$-pyridine-NH-CF$_2$-OPh |
| 5 | 2-(chloromethyl)pyridine·HCl | H2 | 80% | 8.54 (dd, J = 4.8, 0.6 Hz, 1H), 7.75 (d, J = 8.0 Hz, 1H), 7.66-7.60 (m, 2H), 7.51 (d, J = 7.8 Hz, 1H), 7.32-7.27 (m, 1H), 7.24-7.20 (m, 1H), 7.18 (dd, J = 7.8, 5.4 Hz, 1H), 6.99 (d, J = 8.0 Hz, 1H), 6.40 (d, J = 2.0 Hz, 1H), 4.80 (d, J = 13.5 Hz, 1H), 4.76 (d, J = 13.5 Hz, 1H), 3.56 (s, 3H) | 2.05 (B) | benzimidazole-(methylpyrazole)-S-CH$_2$-pyridine |
| 6 | 2-(chloromethyl)pyridine·HCl | H3 | 66% | 8.55 (ddd, J = 4.8, 1.5, 0.7 Hz, 1H), 7.76-7.70 (m, 1H), 7.64 (td, J = 7.7, 1.8 Hz, 1H), 7.51 (d, J = 7.8 Hz, 1H), 7.33-7.28 (m, 1H), 7.23 (td, J = 7.8, 1.1 Hz, 1H), 7.19 (ddd, J = 7.5, 4.9, 0.9 Hz, 1H), 7.15-7.10 (m, 1H), 4.78 (s, 2H), 2.33 (s, 3H), 1.86 (s, 3H) | 2.59 (B) | benzimidazole-(dimethylisoxazole)-S-CH$_2$-pyridine |

-continued

"E" + "H" $\xrightarrow{Cs_2CO_3, DMF}$ Thioether

| Ex. | "E" | "H" | Yield | $^1$H NMR δ(CDCl$_3$) | RT$^a$ | Structure |
|---|---|---|---|---|---|---|
| 7 | 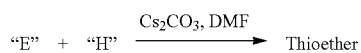 Cl-CH$_2$-pyridine·HCl | H4 | 81% | 8.54 (d, J = 4.3 Hz, 1H), 7.69 (dt, J = 10.4, 5.2 Hz, 2H), 7.49 (d, J = 7.8 Hz, 1H), 7.25-7.20 (m, 1H), 7.14-7.07 (m, 1H), 6.79 (dd, J = 7.8, 2.4 Hz, 1H), 4.77 (s, 2H), 3.94 (s, 3H) | 2.25 (B) | 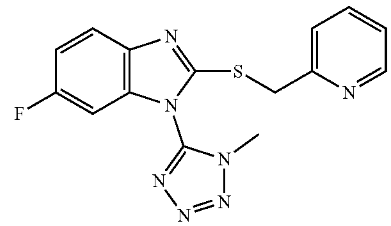 [SMILES: Cn1nnnc1-n1c(SCc2ccccn2)nc2ccc(F)cc21] |
| 8 | E | H4 | 59% | 1.66 (s, 1H), 7.89-7.86 (m, 2H), 7.76 (dd, J = 8.9, 4.7 Hz, 1H), 7.48 (ddd, J = 9.4, 5.5, 2.6 Hz, 3H), 7.43 (dd, J = 8.8, 4.4 Hz, 1H), 7.38 (d, J = 7.8 Hz, 2H), 7.36-7.32 (m, 1H), 7.26-7.20 (m, 1H), 4.73 (s, 2H), 3.98 (s, 3H) | 3.36 (B) | 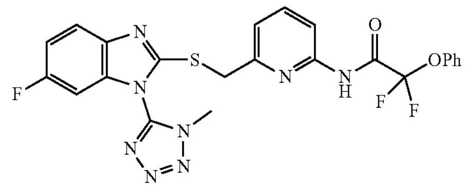 [SMILES: Cn1nnnc1-n1c(SCc2cccc(NC(=O)C(F)(F)Oc3ccccc3)n2)nc2ccc(F)cc21] |
| 9 | Br-CH$_2$-pyridine-NHBoc Ref.$^b$ | H | 62% | 7.82 (d, J = 8.4 Hz, 1H), 7.77 (d, J = 8.0 Hz, 1H), 7.58 (t, J = 7.9 Hz, 1H), 7.40-7.34 (m, 1H), 7.31-7.27 (m, 1H), 7.21 (s, 1H), 7.08 (d, J = 7.5 Hz, 1H), 7.05 (d, J = 8.0 Hz, 1H), 4.64 (s, 2H), 3.89 (s, 3H), 1.51 (s, 9H) | 8.53 (C) | 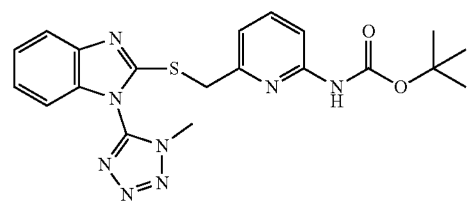 [SMILES: Cn1nnnc1-n1c(SCc2cccc(NC(=O)OC(C)(C)C)n2)nc2ccccc21] |
| 10 | Cl-CH$_2$-pyridine·HCl | H1 | 79% | 8.50 (d, J = 1.4 Hz, 1H), 8.49 (d, J = 1.5 Hz, 1H), 7.79-7.69 (m, 2H), 7.59 (td, J = 7.7, 1.8 Hz, 1H), 7.51 (d, J = 7.8 Hz, 1H), 7.37 (dd, J = 7.7, 4.7 Hz, 1H), 7.29-7.22 (m, 1H), 7.18-7.10 (m, 2H), 6.90 (d, J = 8.0 Hz, 1H), 4.83 (d, J = 13.5 Hz, 1H), 4.73 (d, J = 13.5 Hz, 1H), 2.03 (s, 3H) | 6.17 (D) | 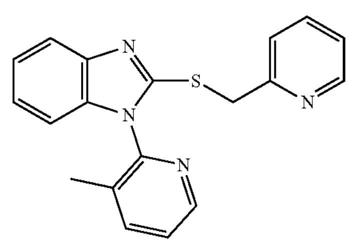 [SMILES: Cc1cccnc1-n1c(SCc2ccccn2)nc2ccccc21] |
| 11 | Cl-CH$_2$-thiazole-NHAc | H | 49% | 9.04 (s, 1H), 7.79 (d, J = 8.0 Hz, 1H), 7.40-7.35 (m, 1H), 7.33-7.28 (m, 1H), 7.08-7.04 (m, 1H), 6.89 (s, 1H), 4.59 (s, 2H), 3.90 (s, 3H), 2.25 (d, J = 4.7 Hz, 3H) | 6.33 (D) | 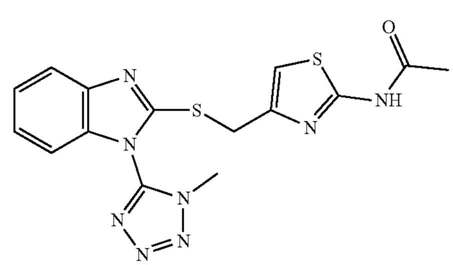 [SMILES: CC(=O)Nc1nc(CSc2nc3ccccc3n2-c2nnnn2C)cs1] |

-continued

"E"  +  "H"  $\xrightarrow{\text{Cs}_2\text{CO}_3, \text{DMF}}$  Thioether

| Ex. | "E" | "H" | Yield | ¹H NMR δ(CDCl₃) | RT$^a$ | Structure |
|---|---|---|---|---|---|---|
| 12 | ClCH₂-(4-thiazolyl)·HCl | H | 64% | 8.75 (d, J = 1.9 Hz, 1H), 7.78 (d, J = 8.0 Hz, 1H), 7.41 (d, J = 1.9 Hz, 1H), 7.37 (td, J = 7.9, 1.1 Hz, 1H), 7.31-7.26 (m, 1H), 7.07-7.03 (m, 1H), 4.80 (s, 2H), 3.87 (s, 3H) | 6.39 (D) | 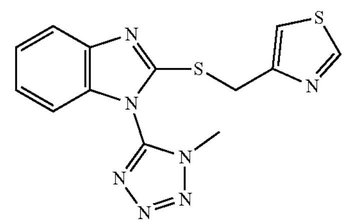 [SMILES: Cn1nnnc1-n1c(SCc2cscn2)nc2ccccc21] |
| 13 | ClCH₂-(6-methyl-2-pyridyl) | H | 53% | 7.79-7.75 (m, 1H), 7.51 (t, J = 7.7 Hz, 1H), 7.36 (td, J = 7.9, 1.1 Hz, 1H), 7.30-7.25 (m, 2H), 7.07-7.03 (m, 2H), 4.73 (s, 2H), 3.91 (s, 3H), 2.51 (s, 3H) | 5.5 (D) | 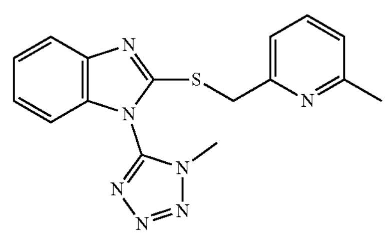 [SMILES: Cc1cccc(CSc2nc3ccccc3n2-c2nnnn2C)n1] |
| 14 | ClCH₂-(2-pyridyl)·HCl | H5 | 82% | 8.61-8.55 (m, 1H), 7.72 (d, J = 7.8 Hz, 1H), 7.67 (t, J = 7.7 Hz, 1H), 7.57 (d, J = 7.3 Hz, 1H), 7.40-7.36 (m, 1H), 7.31 (td, J = 7.7, 1.3 Hz, 1H), 7.25 (ddd, J = 8.5, 7.3, 1.2 Hz, 1H), 7.24-7.19 (m, 1H), 7.16 (s, 1H), 4.82 (s, 2H), 2.56 (s, 3H) | 6.95 (D) | 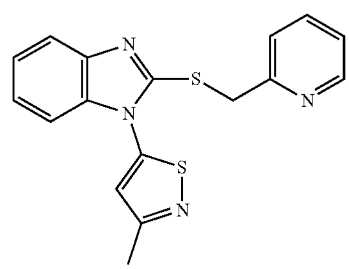 [SMILES: Cc1cc(-n2c(SCc3ccccn3)nc3ccccc32)sn1] |
| 15 | ClCH₂-(2-pyridyl)·HCl | H6 | 58% | 8.59-8.55 (m, 2H), 7.74-7.71 (m, 1H), 7.70-7.64 (m, 2H), 7.58 (d, J = 7.9 Hz, 1H), 7.32 (td, J = 7.6, 1.4 Hz, 1H), 7.30-7.26 (m, 1H), 7.22 (dd, J = 6.7, 5.3 Hz, 1H), 6.87 (d, J = 1.8 Hz, 1H), 4.85 (s, 2H) | 6.29 (D) | 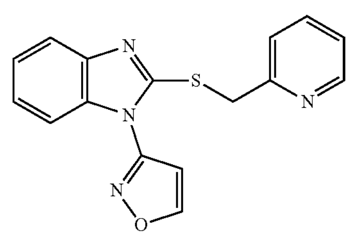 [SMILES: c1ccc(CSc2nc3ccccc3n2-c2ccon2)nc1] |
| 16 | ClCH₂-(2-methyl-4-thiazolyl) | H | 40% | 7.80-7.75 (m, 1H), 7.37 (td, J = 7.8, 1.0 Hz, 1H), 7.28 (td, J = 7.9, 1.1 Hz, 1H), 7.15 (s, 1H), 7.08-7.03 (m, 1H), 4.69 (s, 2H), 3.89 (s, 3H), 2.66 (s, 3H) | 6.79 (D) | 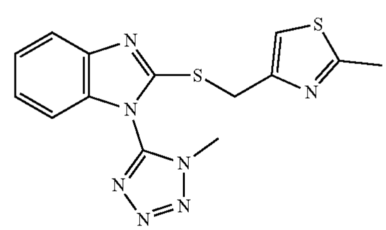 [SMILES: Cc1nc(CSc2nc3ccccc3n2-c2nnnn2C)cs1] |
| 17 | ClCH₂-(2-methylamino-4-thiazolyl) | H | 62% | 7.79-7.75 (m, 1H), 7.39-7.34 (m, 1H), 7.31-7.26 (m, 1H), 7.05 (d, J = 8.0 Hz, 1H), 6.46 (s, 1H), 5.26 (s, 1H), 4.51 (s, 2H), 3.89 (s, 3H), 2.92 (d, J = 5.0 Hz, 3H). | 6.55 (C) | 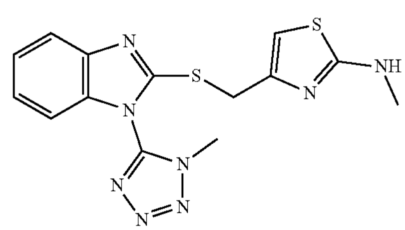 [SMILES: CNc1nc(CSc2nc3ccccc3n2-c2nnnn2C)cs1] |

-continued

"E" + "H" →(Cs₂CO₃, DMF) Thioether

| Ex. | "E" | "H" | Yield | ¹H NMR δ(CDCl₃) | RT$^a$ | Structure |
|---|---|---|---|---|---|---|
| 18 | (bromomethyl pyridine methyl ester) | H | 66% | 8.03 (dd, J = 7.4, 1.3 Hz, 1H), 7.83-7.74 (m, 3H), 7.37 (td, J = 7.9, 1.1 Hz, 1H), 7.29 (td, J = 7.8, 1.0 Hz, 1H), 7.05 (d, J = 8.0 Hz, 1H), 4.84 (s, 2H), 3.98 (s, 3H), 3.94 (s, 3H) | 6.81 (C) | 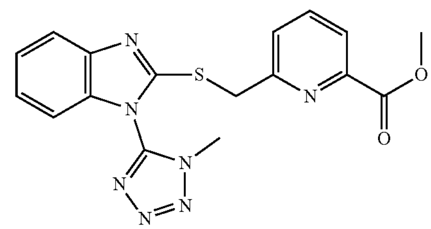 [SMILES: COC(=O)c1cccc(CSc2nc3ccccc3n2-c2nnnn2C)n1] |
| 19 | (bromomethyl isoquinoline · HBr) | H | 58% | 8.41 (t, J = 6.3 Hz, 2H), 7.86 (d, J = 8.2 Hz, 1H), 7.74-7.69 (m, 1H), 7.67 (d, J = 5.6 Hz, 1H), 7.61 (ddd, J = 8.3, 7.0, 1.1 Hz, 1H), 7.53 (br s, 2H), 7.43 (s, 1H), 7.26 (s, 1H), 7.23-7.17 (m, 2H), 4.02-3.99 (m, 3H) | 7.03 (C) | 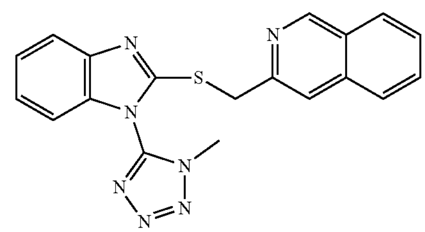 [SMILES: Cn1nnnc1-n1c(SCc2cc3ccccc3cn2)nc2ccccc21] |
| 20 | (2-chloromethyl pyridine · HCl) | H7 | 70% | 8.67 (s, 1H), 8.52 (d, J = 10.9 Hz, 2H), 7.80 (t, J = 9.3 Hz, 1H), 7.62 (t, J = 7.4 Hz, 1H), 7.53 (t, J = 9.0 Hz, 1H), 7.36-7.28 (m, 1H), 7.24-7.12 (m, 2H), 6.92 (t, J = 9.3 Hz, 1H), 4.93-4.81 (m, 1H), 4.76 (t, J = 12.1 Hz, 1H), 2.38-2.28 (m, 3H) | 2.05 (B) | 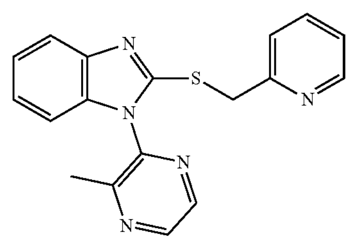 [SMILES: Cc1nccnc1-n1c(SCc2ccccn2)nc2ccccc21] |
| 21 | (2-chloromethyl pyridine · HCl) | H8 | 68% | 8.54 (ddd, J = 4.9, 1.7, 0.9 Hz, 1H), 7.67 (td, J = 7.7, 1.8 Hz, 1H), 7.49 (d, J = 7.8 Hz, 1H), 7.22 (ddd, J = 7.5, 4.9, 1.0 Hz, 1H), 6.88 (td, J = 9.9, 2.2 Hz, 1H), 6.62 (ddd, J = 7.4, 2.1, 0.8 Hz, 1H), 4.80 (s, 2H), 3.96 (s, 3H) | 1.65 (F) | 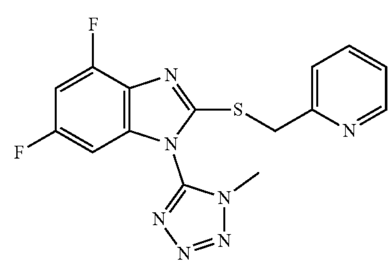 [SMILES: Cn1nnnc1-n1c(SCc2ccccn2)nc2c(F)cc(F)cc21] |
| 22 | I | H | 22% | 7.78 (d, J = 8.1 Hz, 1H), 7.44-7.34 (m, 3H), 7.32-7.27 (m, 3H), 7.24 (d, J = 8.6 Hz, 1H), 7.10-7.03 (m, 2H), 4.63 (s, 2H), 3.92 (s, 3H) | 1.74 (A) | 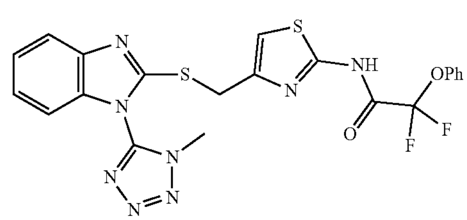 [SMILES: Cn1nnnc1-n1c(SCc2csc(NC(=O)C(F)(F)Oc3ccccc3)n2)nc2ccccc21] |
| 23 | N | H | 28% | 9.16 (br s, 1H), 7.77 (d, J = 8.0 Hz, 1H), 7.36 (td, J = 7.9, 1.1 Hz, 1H), 7.31-7.26 (m, 1H), 7.05 (d, J = 8.0 Hz, 1H), 6.88 (s, 1H), 4.65 (d, J = 8.4 Hz, 2H), 3.86 (s, J = 8.4 Hz, 3H), 1.53 (s, 9H) | 8.06 (C) | 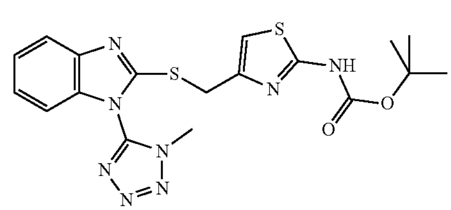 [SMILES: Cn1nnnc1-n1c(SCc2csc(NC(=O)OC(C)(C)C)n2)nc2ccccc21] |

-continued

| Ex. | "E" | "H" | Yield | ¹H NMR δ(CDCl₃) | RTᵃ | Structure |
|---|---|---|---|---|---|---|
| 24 | Br-CH₂-C(=O)-O-CH₃ | H | 13% | 7.74 (d, J = 8.0 Hz, 1H), 7.38-7.33 (m, 1H), 7.32-7.27 (m, 1H), 7.07-7.04 (m, 1H), 4.22 (s, 2H), 4.04 (s, 3H), 3.76 (s, 3H). | 6.53 (C) | 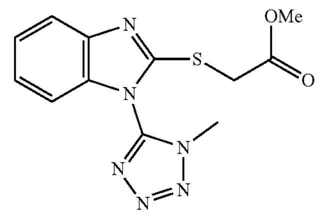 [SMILES: COC(=O)CSc1nc2ccccc2n1-c1nnnn1C] |
| 25 | Br-CH₂-C(=O)-N(pyrrolidine) | H | 85% | 7.70 (d, J = 8.1 Hz, 1H), 7.34 (td, J = 7.7, 1.1 Hz, 1H), 7.28 (dt, J = 4.4, 2.3 Hz, 1H), 7.06 (d, J = 7.9 Hz, 1H), 4.29 (d, J = 7.1 Hz, 2H), 4.08 (s, 3H), 3.63 (t, J = 6.9 Hz, 2H), 3.46 (t, J = 6.9 Hz, 2H), 2.03 (p, J = 6.8 Hz, 2H), 1.90 (p, J = 6.8 Hz, 2H) | 6.23 (C) | 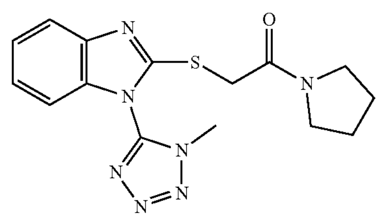 [SMILES: Cn1nnnc1-n1c(SCC(=O)N2CCCC2)nc2ccccc21] |

ᵃRT = LCMS retention time in minutes using indicated Method (A-D or F);
ᵇCommercially available or see procedure described in Bioconjugate Chem., 2014, 25, 724-737 or prepared from (6-aminopyridin-2-yl)methanol by procedures analogous to those described for Intermediate N.

Example 26—6-(((1-(1-Methyl-1H-tetrazol-5-yl)-1H-benzo[d]imidazol-2-yl)thio)methyl)pyridin-2-amine 26

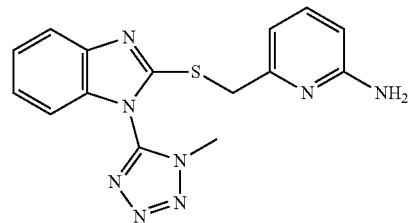 [SMILES: Cn1nnnc1-n1c(SCc2cccc(N)n2)nc2ccccc21]

A partial solution of 2-(6-(((1-(1-methyl-1H-tetrazol-5-yl)-1H-benzo[d]imidazol-2-yl)thio)methyl)pyridin-2-yl) isoindoline-1,3-dione O (184 mg, 0.393 mmol) in THF (5 mL) and methanol (2 mL) was treated with hydrazine hydrate (50-60% by wt.) (21 μl, 0.43 mmol) and stirred at RT for 50 minutes then loaded onto silica (1 g) and chromatographed on silica (10 g Biotage KP-Sil cartridge) eluting with 50-100% EtOAc/PE then 0-20% MeOH/EtOAc to give 6-(((1-(1-methyl-1H-tetrazol-5-yl)-1H-benzo[d]imidazol-2-yl)thio)methyl)pyridin-2-amine 26 (88 mg, 66%) as a white solid.

¹H NMR (500 MHz, CDCl₃+d₄-MeOH) δ 8.18 (d, J=8.1 Hz, 1H), 7.75 (dtd, J=15.5, 7.7, 4.2 Hz, 3H), 7.47 (d, J=8.1 Hz, 1H), 7.14 (d, J=7.3 Hz, 1H), 6.81 (d, J=8.2 Hz, 1H), 4.95 (s, 2H), 4.31 (s, 3H); LCMS (method D): 4.89 min (339.2, MH⁺).

Example 27—N-(6-(((1-(1-Methyl-1H-tetrazol-5-yl)-1H-benzo[d]imidazol-2-yl)thio)methyl)pyridin-2-yl)acetamide 27

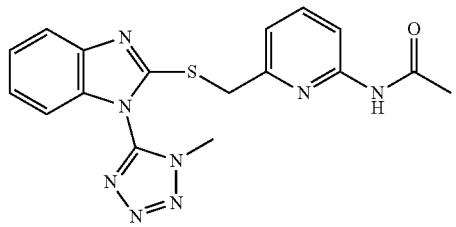 [SMILES: CC(=O)Nc1cccc(CSc2nc3ccccc3n2-c2nnnn2C)n1]

A suspension of 6-(((1-(1-methyl-1H-tetrazol-5-yl)-1H-benzo[d]imidazol-2-yl)thio)methyl)pyridin-2-amine 26 (40 mg, 0.12 mmol) in dry DCM (1 mL) was treated with pyridine (14 μL, 0.18 mmol) then acetyl chloride (10 μL, 0.14 mmol) and stirred at RT for 1 h then transferred to a column of silica (4 g Puriflash cartridge) and eluted with 50-100% EtOAc/PE to give N-(6-(((1-(1-methyl-1H-tetrazol-5-yl)-1H-benzo[d]imidazol-2-yl)thio)methyl)pyridin-2-yl)acetamide 27 (5.5 mg, 12%) as an opaque, colourless gum.

¹H NMR (500 MHz, CDCl₃) δ 8.16-8.07 (m, 1H), 8.07-8.01 (m, 1H), 7.79-7.73 (m, 1H), 7.64-7.55 (m, 1H), 7.40-7.35 (m, 1H), 7.33-7.28 (m, 1H), 7.13-7.10 (m, 1H), 7.09-7.06 (m, 1H), 4.63 (s, 2H), 3.93 (s, 3H), 2.21 (s, 3H); LCMS (method D): 6.43 min (381.0, MH⁺).

Example 28—Ethyl (6-(((1-(1-methyl-1H-tetrazol-5-yl)-1H-benzo[d]imidazol-2-yl)thio)methyl)pyridin-2-yl)carbamate 28

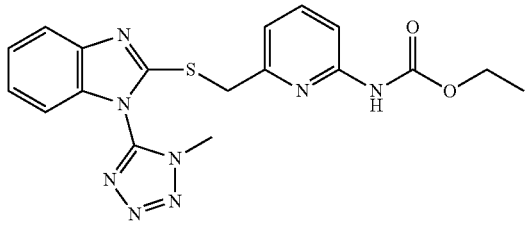 [SMILES: CCOC(=O)Nc1cccc(CSc2nc3ccccc3n2-c2nnnn2C)n1]

Ethyl chloroformate (0.012 mL, 0.12 mmol) was added to a solution of 6-(((1-(1-methyl-1H-tetrazol-5-yl)-1H-benzo[d]imidazol-2-yl)thio)methyl)pyridin-2-amine 26 (22.8 mg, 0.067 mmol) and 4-(dimethylamino)pyridine (0.66 mg, 5.4 µmol) in 1,4-dioxane (1 mL) and pyridine (7.1 µL, 0.088 mmol) and the reaction mixture was stirred at RT for 3 days. More pyridine (7.1 µL, 0.088 mmol) and ethyl chloroformate (0.012 mL, 0.12 mmol) were added and the mixture stirred a further 4 h then an aqueous solution of sodium bicarbonate (10 g/L, 7 mL) was added and the mixture was extracted with EtOAc (12 mL). The organics were washed with brine, dried (MgSO4) then concentrated and chromatographed on silica (4 g Puriflash cartridge) eluting with 50-100% EtOAc/PE to give ethyl (6-(((1-(1-methyl-1H-tetrazol-5-yl)-1H-benzo[d]imidazol-2-yl)thio)methyl)pyridin-2-yl)carbamate 28 (11 mg, 40%) as a gum.

$^1$H NMR (500 MHz, CDCl$_3$) δ 7.85 (d, J=8.3 Hz, 1H), 7.79-7.74 (m, 1H), 7.63-7.57 (m, 1H), 7.38 (br s, 1H), 7.38-7.34 (m, 1H), 7.31-7.26 (m, 1H), 7.10 (d, J=7.4 Hz, 1H), 7.07-7.03 (m, 1H), 4.64 (s, 2H), 4.22 (q, J=7.1 Hz, 2H), 3.89 (s, 3H), 1.31 (t, J=7.1 Hz, 3H); LCMS (method D): 7.51 min (411.1, MH$^+$).

The following example compounds can be made analogously to the methods described above:

29

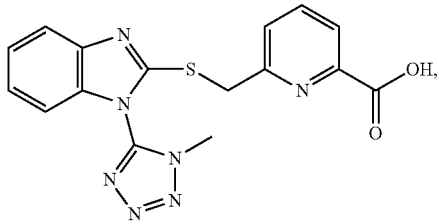

30

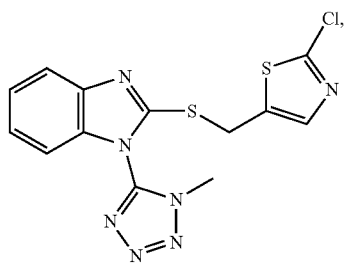

31

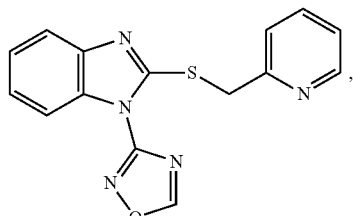

32

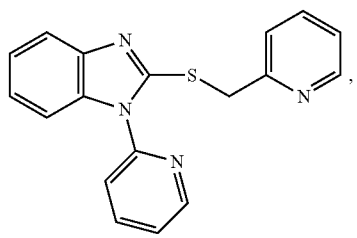

33

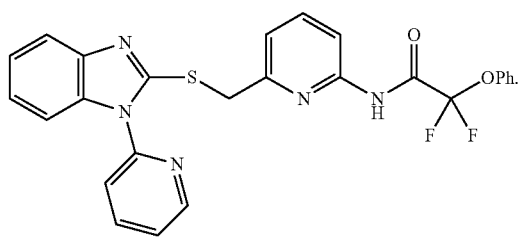

Using the method described in Example 1, substituting either or both of E or H with the appropriate electrophile "E" or benzimidazol-2-thione derivative "H", and with additional base if "E" was a salt, and DMF was generally used as solvent in place of THF, there were thus obtained the following Examples (thioethers, Ex. 34-58):

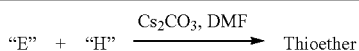

"E" + "H" →(Cs$_2$CO$_3$, DMF)→ Thioether

| Ex. | "E" | "H" | Yield | $^1$H NMR δ(CDCl$_3$) | RT$^a$ | Structure |
|---|---|---|---|---|---|---|
| 34 | ![Cl-CH2-thiazole] | H | 47% | 7.80 (d, J = 8.1 Hz, 1H), 7.72 (d, J = 3.3 Hz, 1H), 7.41-7.36 (m, 1H), 7.31 (t, J = 7.8 Hz, 1H), 7.28 (d, J = 3.3 Hz, 1H), 7.06 (d, J = 8.0 Hz, 1H), 5.00 (s, 2H), 3.91 (s, 3H) | 2.43 (B) | ![structure] |

-continued

"E" + "H" $\xrightarrow{Cs_2CO_3, DMF}$ Thioether

| Ex. | "E" | "H" | Yield | $^1$H NMR δ(CDCl$_3$) | RT$^a$ | Structure |
|---|---|---|---|---|---|---|
| 35 | P1 | H | 38% | 8.14 (s, 1H), 7.79 (d, J = 8.0 Hz, 1H), 7.69 (d, J = 7.9 Hz, 1H), 7.40-7.36 (m, 1H), 7.33-7.29 (m, 1H), 7.18 (d, J = 7.7 Hz, 1H), 7.08-7.05 (m, 1H), 4.68 (s, 2H), 3.94 (s, 3H), 1.54-1.47 (m, 1H), 1.12-1.07 (m, 2H), 0.97-0.91 (m, 2H) | 2.67 (B) | 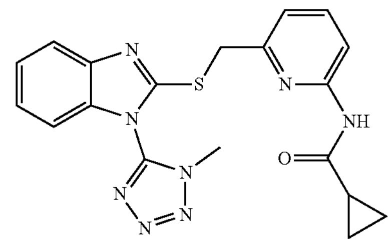 [SMILES: Cn1nnnc1-n1c(SCc2cccc(NC(=O)C3CC3)n2)nc2ccccc21] |
| 36 | P3 | H | 12% | 8.18 (s, 1H), 7.80 (d, J = 8.1 Hz, 1H), 7.72 (d, J = 7.8 Hz, 1H), 7.40-7.36 (m, 1H), 7.33-7.28 (m, 1H), 7.19 (s, 1H), 7.07 (d, J = 8.1 Hz, 1H), 4.67 (s, 2H), 3.95 (s, 3H), 2.55-2.46 (m, 2H), 1.25 (t, J = 7.5 Hz, 3H) | 2.57 (B) | 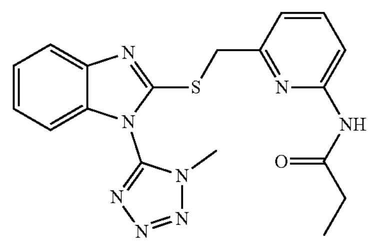 [SMILES: CCC(=O)Nc1cccc(CSc2nc3ccccc3n2-c2nnnn2C)n1] |
| 37 | P4 | H | 10% | 8.41 (d, J = 5.3 Hz, 1H), 7.77 (d, J = 8.0 Hz, 1H), 7.48 (s, J = 7.3 Hz, 1H), 7.37 (t, J = 7.7 Hz, 1H), 7.29 (t, J = 7.5 Hz, 1H), 7.17 (s, 1H), 7.05 (d, J = 8.0 Hz, 1H), 4.87 (s, 2H), 3.97 (s, 3H), 2.41 (s, 3H) | 2.03 (B) | 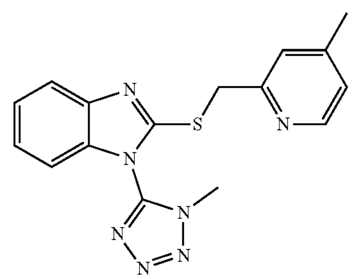 [SMILES: Cc1ccnc(CSc2nc3ccccc3n2-c2nnnn2C)c1] |
| 38 | P5 | H | 50% | 8.17 (s, 1H), 7.77 (d, J = 8.0 Hz, 1H), 7.36 (t, J = 7.7 Hz, 1H), 7.29 (t, J = 7.7 Hz, 1H), 7.05 (d, J = 8.0 Hz, 1H), 4.84 (s, 2H), 4.00 (s, 3H), 3.79 (s, 3H), 2.35 (s, 3H), 2.26 (s, 3H) | 2.43 (B) | 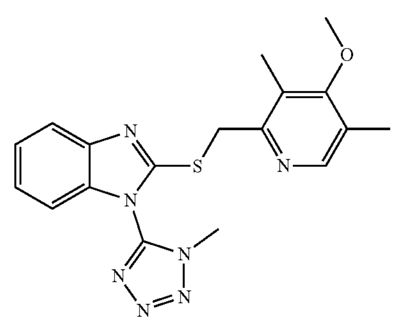 [SMILES: COc1c(C)cnc(CSc2nc3ccccc3n2-c2nnnn2C)c1C] |
| 39 | P6 | H | 12% | 8.18 (d, J = 5.7 Hz, 1H), 7.78 (d, J = 8.0 Hz, 1H), 7.36 (t, J = 7.3 Hz, 1H), 7.31-7.27 (m, 1H), 7.05 (d, J = 8.0 Hz, 1H), 6.85 (d, J = 5.7 Hz, 1H), 4.88 (s, 2H), 4.00 (s, 3H), 3.95 (s, 3H), 3.91 (s, 3H) | 2.11 (B) | 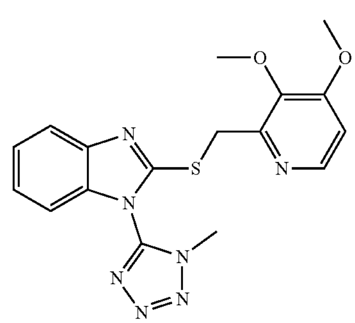 [SMILES: COc1ccnc(CSc2nc3ccccc3n2-c2nnnn2C)c1OC] |

-continued

"E" + "H" $\xrightarrow{Cs_2CO_3, DMF}$ Thioether

| Ex. | "E" | "H" | Yield | $^1$H NMR δ(CDCl$_3$) | RT$^a$ | Structure |
|---|---|---|---|---|---|---|
| 40 | P7 | H | 34% | 8.25 (d, J = 5.8 Hz, 1H), 7.77 (d, J = 8.0 Hz, 1H), 7.36 (t, J = 7.7 Hz, 1H), 7.28 (t, J = 8.1 Hz, 1H), 7.05 (d, J = 8.0 Hz, 1H), 6.74 (d, J= 5.8 Hz, 1H), 4.87 (s, 2H), 4.13 (t, J = 6.2 Hz, 2H), 4.00 (s, 3H), 3.56 (t, J = 6.0 Hz, 2H), 3.35 (s, 3H), 2.29 (s, 3H), 2.09 (p, J = 6.1 Hz, 2H). | 2.39 (B) | 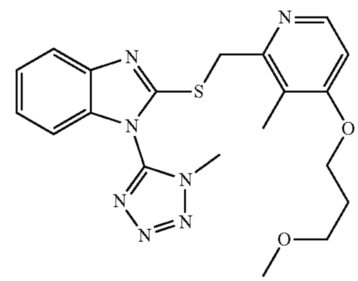 [SMILES: COCCCOc1ccnc(CSc2nc3ccccc3n2-c2nnnn2C)c1C] |
| 41 | P8 | H | 39% | 8.32 (d, J = 5.7 Hz, 1H), 7.77 (d, J = 8.0 Hz, 1H), 7.37 (t, J = 7.4 Hz, 1H), 7.29 (t, J = 7.4 Hz, 1H), 7.05 (d, J = 7.9 Hz, 1H), 6.70 (d, J = 5.7 Hz, 1H), 4.88 (s, 2H), 4.42 (q, J = 7.8 Hz, 2H), 4.00 (s, 3H), 2.35 (s, 3H). | 2.82 (B) | 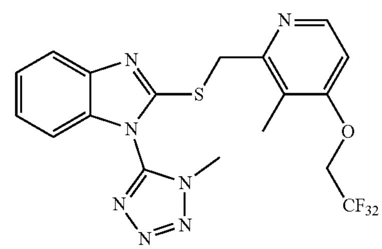 |
| 42$^b$ | P9 | H | 21% | 8.36 (d, J = 6.0 Hz, 1H), 7.76 (d, J = 8.0 Hz, 1H), 7.37 (t, J = 7.3 Hz, 1H), 7.28 (d J = 6.0 Hz, 1H), 7.20 (s, 1H), 7.05 (d, J = 8.0 Hz, 1H), 6.82 (d, J = 4.3 Hz, 1H), 4.83 (s, 2H), 3.95 (s, 3H), 3.88 (s, 3H). | 1.91 (B) | |
| 43$^b$ | P10 | H | 2% | 9.16 (s, 1H), 8.71 (d, J = 5.2 Hz, 1H), 7.76 (d, J = 8.1 Hz, 1H), 7.63 (d, J = 5.5 Hz, 1H), 7.38 (t, J = 7.4 Hz, 1H), 7.33-7.28 (m, 1H), 7.05 (d, J = 8.1 Hz, 1H), 4.74 (s, 2H), 3.97 (s, 3H). | 2.04 (B) | |
| 44 | P | H12 | 58% | 8.89 (s, 1H), 8.15 (d, J = 8.3 Hz, 1H), 7.73 (t, J = 7.9 Hz, 1H), 7.66 (d, J = 8.5, 1H), 7.50 (d, J = 8.5 Hz, 1H), 7.40 (d, J = 7.7 Hz, 3H), 7.29 (d, J = 8.1 Hz, 4H), 4.66 (s, 2H), 3.95 (s, 3H). | 3.66 (B) | 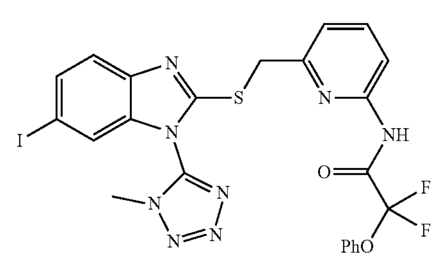 [SMILES: Cn1nnnc1-n1c(SCc2cccc(NC(=O)C(F)(F)Oc3ccccc3)n2)nc2ccc(I)cc21] |

-continued

"E" + "H" $\xrightarrow{Cs_2CO_3, DMF}$ Thioether

| Ex. | "E" | "H" | Yield | $^1$H NMR δ(CDCl$_3$) | RT$^a$ | Structure |
|---|---|---|---|---|---|---|
| 45 | P | H14 | 39% | 9.16 (s, 1H), 8.98 (s, 1H), 8.83 (br s, 1H), 8.11 (d, J = 7.9 Hz, 1H), 7.81-7.75 (m, 1H), 7.72-7.66 (m, 1H), 7.42-7.38 (m, 2H), 7.35-7.21 (m, 6H), 7.09-7.06 (m, 1H), 4.66 (s, 2H) | 3.44 (B) | 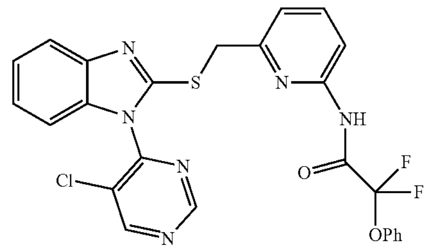 [SMILES: O=C(Nc1cccc(CSc2nc3ccccc3n2-c2ncncc2Cl)n1)C(F)(F)Oc1ccccc1] |
| 46 | (structure: methyl 6-(bromomethyl)picolinate) | H1 | 77% | 8.51 (d, J = 1.4 Hz, 1H), 7.99 (d, J = 7.7 Hz, 1H), 7.87 (d, J = 7.8 Hz, 1H), 7.79-7.72 (m, 3H), 7.40 (d, J = 7.7 Hz, 1H), 7.28 (t, J = 6.7 Hz, 1H), 7.18 (t, J = 7.4 Hz, 1H), 6.92 (d, J = 8.0 Hz, 1H), 4.87 (m, 2H), 3.97 (s, 3H), 2.04 (s, 3H) | 2.86 (A) | 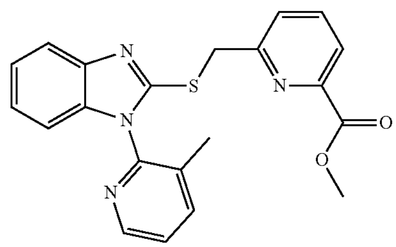 [SMILES: COC(=O)c1cccc(CSc2nc3ccccc3n2-c2ncccc2C)n1] |
| 47 | P2 | H4 | 58% | 8.91 (s, 1H), 8.18 (d, J = 8.2 Hz, 1H), 7.72-7.69 (m, 1H), 7.68 (t, J = 8.0 Hz, 1H), 7.35 (dd, J = 8.7, 7.4 Hz, 2H), 7.22 (d, J = 7.4 Hz, 1H), 7.11 (ddd, J = 9.4, 9.0, 2.5 Hz, 1H), 7.07 (t, J = 7.4 Hz, 1H), 7.01 (dd, J = 8.7, 1.0 Hz, 2H), 6.79 (dd, J = 7.8, 2.4 Hz, 1H), 4.63 (s, 2H), 4.63 (s, 2H), 3.90 (s, 3H) | 3.21 (B) | 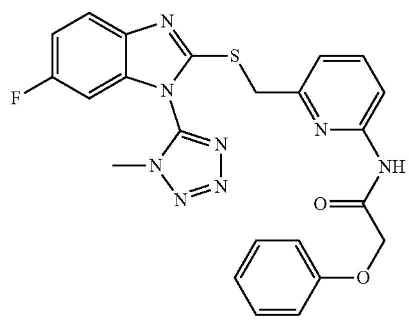 [SMILES: Cn1nnnc1-n1c(SCc2cccc(NC(=O)COc3ccccc3)n2)nc2ccc(F)cc21] |
| 48 | E1 | H4 | 61% | 7.75-7.70 (m, 2H), 7.29 (d, J = 3.4 Hz, 1H), 7.16-7.10 (m, 1H), 6.80 (dd, J = 7.8, 2.4 Hz, 1H), 4.97 (s, 2H), 3.93 (s, 3H) | 2.25 (B) | 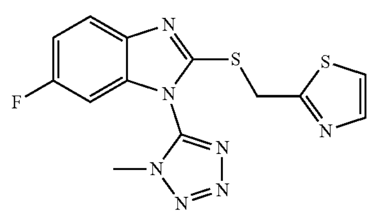 [SMILES: Cn1nnnc1-n1c(SCc2nccs2)nc2ccc(F)cc21] |
| 49$^c$ | (structure: 2-(chloromethyl)pyridine·HCl) | H9 | 50% | 8.53 (ddd, J = 4.7, 1.4, 0.7 Hz, 1H), 7.73 (d, J = 8.0 Hz, 1H), 7.62 (td, J = 7.7, 1.8 Hz, 1H), 7.52 (d, J = 7.8 Hz, 1H), 7.31-7.26 (m, 1H), 7.23-7.18 (m, 1H), 7.18-7.14 (m, 2H), 7.06-7.02 (m, 2H), 4.82 (d, J = 13.0 Hz, 1H), 4.72 (d, J = 13.3 Hz, 1H), 3.37 (s, 3H) | 1.25 (B) | |

-continued

"E" + "H" $\xrightarrow{Cs_2CO_3, DMF}$ Thioether

| Ex. | "E" | "H" | Yield | $^1$H NMR δ(CDCl$_3$) | RT$^a$ | Structure |
|---|---|---|---|---|---|---|
| 50 | E | H9 | 37% | 9.33 (s, 1H), 8.09 (d, J = 8.2 Hz, 1H), 7.72 (d, J = 8.0 Hz, 1H), 7.68 (t, J = 7.9 Hz, 1H), 7.41-7.36 (m, 2H), 7.31-7.26 (m, 5H), 7.22-7.18 (m, 2H), 7.06 (d, J = 1.4 Hz, 1H), 7.04 (d, J = 8.1 Hz, 1H), 4.73 (d, J = 12.9 Hz, 1H), 4.62 (d, J = 13.3 Hz, 1H), 3.41 (s, 3H) | 3.12 (B) | 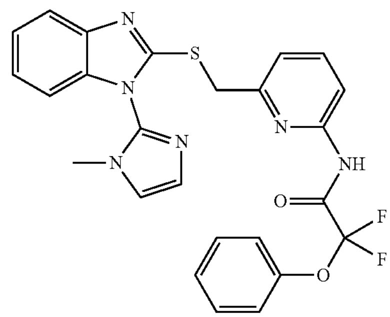 [SMILES: Cn1ccnc1-n1c(SCc2cccc(NC(=O)C(F)(F)Oc3ccccc3)n2)nc2ccccc21] |
| 51 | 2-(chloromethyl)pyridine·HCl | H10 | 61% | 8.73 (s, 2H), 8.53 (d, J = 4.8 Hz, 1H), 7.79 (d, J = 8.1 Hz, 1H), 7.62 (t, J = 7.7 Hz, 1H), 7.50 (d, J = 7.8 Hz, 1H), 7.32 (t, J = 7.7 Hz, 1H), 7.22 (t, J = 7.7 Hz, 1H), 7.18 (dd, J = 6.9, 5.5 Hz, 1H), 6.86 (d, J = 8.0 Hz, 1H), 4.81 (s, 2H) | 2.74 (B) | 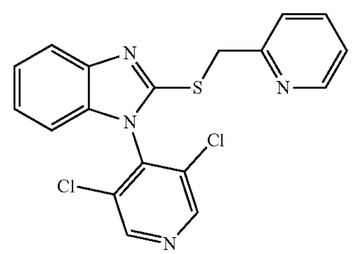 [SMILES: Clc1cncc(Cl)c1-n1c(SCc2ccccn2)nc2ccccc21] |
| 52 | 2-(chloromethyl)pyridine·HCl | H11 | 42% | 8.55 (d, J = 4.2 Hz, 1H), 7.70 (t, J = 7.2 Hz, 1H), 7.61 (d, J = 8.6 Hz, 1H), 7.52 (d, J = 7.6 Hz, 1H), 7.47 (dd, J = 8.5, 1.8 Hz, 1H), 7.25 (d, J = 8.3 Hz, 1H), 7.22 (m, 1H), 4.81 (s, 2H), 3.95 (s, 3H) | 2.70 (B) | 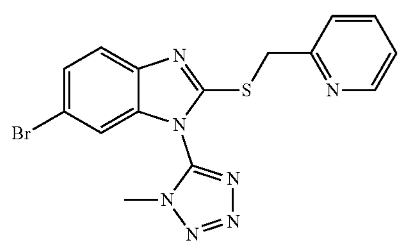 [SMILES: Cn1nnnc1-n1c(SCc2ccccn2)nc2ccc(Br)cc21] |
| 53 | N | H11 | 49% | 7.63 (d, J = 8.6 Hz, 1H), 7.48 (d, J = 8.6 Hz, 1H), 7.22 (m, 1H), 6.87 (s, 1H), 4.60 (s, 2H), 3.92 (s, 3H), 1.53 (s, 9H) | 3.42 (B) | 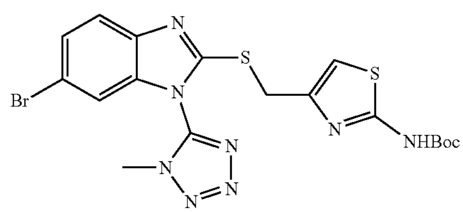 [SMILES: Cn1nnnc1-n1c(SCc2csc(NC(=O)OC(C)(C)C)n2)nc2ccc(Br)cc21] |
| 54 | Q | H12 | 26% | 8.54 (d, J = 4.6 Hz, 1H), 7.74-7.61 (m, 2H), 7.50 (d, J = 8.4 Hz, 2H), 7.39 (s, 1H), 7.24 (d, J = 7.2 Hz, 1H), 4.79 (s, 2H), 3.94 (s, 3H) | 2.82 (B) | 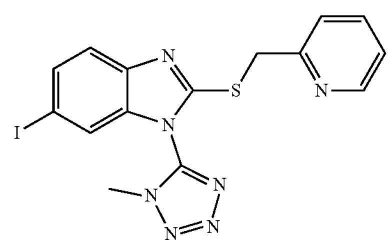 [SMILES: Cn1nnnc1-n1c(SCc2ccccn2)nc2ccc(I)cc21] |
| 55 | 2-chloro-N-ethylacetamide | H | 29% | 7.73 (d, J = 8.0 Hz, 1H), 7.41-7.37 (m, 1H), 7.35-7.30 (m, 1H), 7.07 (dd, J = 7.2, 0.7 Hz, 1H), 4.02 (s, 3H), 3.94 (s, 2H), 3.30 (qd, J = 7.3, 5.6 Hz, 2H), 1.13 (t, J = 7.3 Hz, 3H) | 2.07 (B) | 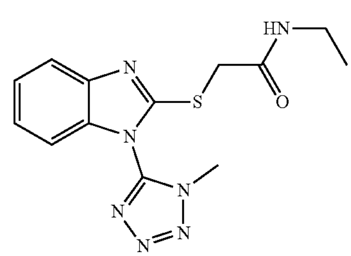 [SMILES: CCNC(=O)CSc1nc2ccccc2n1-c1nnnn1C] |

| Ex. | "E" | "H" | Yield | ¹H NMR δ(CDCl₃) | RTᵃ | Structure |
|---|---|---|---|---|---|---|
| 56 | Cl-CH₂-C(O)-N-morpholine | H | 19% | 7.78 (d, J = 8.0 Hz, 1H), 7.41 (td, J = 7.9, 1.1 Hz, 1H), 7.34 (td, J = 7.9, 1.1 Hz, 1H), 7.08 (d, J = 8.1 Hz, 1H), 4.52 (s, 2H), 4.08 (s, 3H), 3.80-3.75 (m, 2H), 3.68 (dt, J = 8.0, 4.5 Hz, 4H), 3.64-3.58 (m, 2H) | 2.32 (B) | benzimidazole-tetrazole-thioether-morpholine |
| 57ᵈ | PhNH-C(O)-CH₂-Cl | H | 97% | 10.21 (s, 1H), 7.87 (d, J = 8.1 Hz, 1H), 7.56 (dd, J = 8.6, 1.0 Hz, 2H), 7.47 (td, J = 7.9, 1.0 Hz, 1H), 7.41-7.36 (m, 1H), 7.31 (dd, J = 8.4, 7.6 Hz, 2H), 7.13-7.08 (m, 2H), 4.13 (s, 2H), 4.03 (s, 3H) | 2.81 (B) | benzimidazole-tetrazole-thioether-NHPh |
| 58ᵈ | (CH₃)₂N-C(O)-CH₂-Cl | H | 79% | 7.74 (d, J = 8.0 Hz, 1H), 7.37 (td, J = 7.8, 1.1 Hz, 1H), 7.30 (td, J = 7.8, 1.1 Hz, 1H), 7.06 (d, J = 7.9 Hz, 1H), 4.45 (s, 2H), 4.08 (s, 3H), 3.18 (s, 3H), 2.98 (s, 3H) | 2.17 (B) | benzimidazole-tetrazole-thioether-NMe₂ |

ᵃRT = LCMS retention time in minutes using indicated Method (A-D or F);
ᵇPurified by prep. HPLC (acidic);
ᶜReaction was heated at 50° C. for 72 hours and then KI was added and stirred for a further 6 hours at RT;
ᵈNaHCO₃ was used as a base instead of Cs₂CO₃.

Example 59—1-(5-Chloropyrimidin-4-yl)-2-((pyridin-2-ylmethyl)thio)-1H-benzo[d]imidazole 59

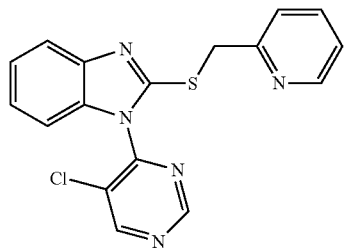 [SMILES: Clc1cncnc1-n1c(SCc2ccccn2)nc2ccccc21]

A solution of 4,5-dichloropyrimidine (0.15 mL, 1.5 mmol) and 2-((pyridin-2-ylmethyl)thio)-1H-benzo[d]imidazole R (300 mg, 1.24 mmol) in dry DMF (1.5 mL) was treated with a 60% mineral oil dispersion of sodium hydride (55 mg, 1.4 mmol), stirred at RT for 5 min then heated to 70° C. for 90 min. The mixture was treated with saturated aqueous ammonium chloride solution (2 mL), diluted with EtOAc (40 mL), washed with water (3×40 mL) and brine, dried (MgSO₄) and chromatographed on a basic silica column eluting with 0-100% EtOAc/PE. The product was purified further by mass-directed prep. HPLC eluting with MeCN—H₂O to give 1-(5-chloropyrimidin-4-yl)-2-((pyridin-2-ylmethyl)thio)-1H-benzo[d]imidazole 59 (22 mg, 5%) as a pale orange gum.

¹H NMR (500 MHz, CDCl₃) δ 9.15 (s, 1H), 8.96 (s, 1H), 8.52 (d, J=4.3 Hz, 1H), 7.76 (d, J=8.0 Hz, 1H), 7.60 (td, J=7.7, 1.8 Hz, 1H), 7.47 (d, J=7.8 Hz, 1H), 7.36-7.29 (m, 1H), 7.25-7.20 (m, 1H), 7.16 (dd, J=6.8, 5.0 Hz, 1H), 7.05 (d, J=8.0 Hz, 1H), 4.77 (s, 2H); LCMS (method B): 2.23 min (354.2, MH⁺).

Example 60—1-(1-Methyl-1H-tetrazol-5-yl)-2-(pyrimidin-2-ylthio)-1H-benzo[d]imidazole 60

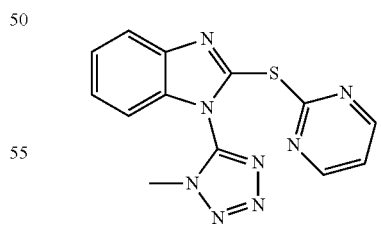

A solution of 1-(1-methyl-1H-tetrazol-5-yl)-2-(methylsulfonyl)-1H-benzo[d]imidazole T (66 mg, 0.24 mmol) and 2-mercaptopyrimidine (30 mg, 0.27 mmol) in dry DMF (1 mL) was treated with sodium carbonate (35 mg, 0.33 mmol) and stirred at 90° C. for 4 hours. The reaction mixture was diluted with EtOAc (20 mL), washed with water (3×20 mL) and brine, dried (MgSO₄) and chromatographed on silica eluting with 40-90% EtOAc/PE to give 1-(1-methyl-1H- tetrazol-5-yl)-2-(pyrimidin-2-ylthio)-1H-benzo[d]imidazole 60 (39 mg, 53%) as a white foam.

$^1$H NMR (500 MHz, CDCl$_3$) δ 8.40 (d, J=4.9 Hz, 2H), 7.95 (ddd, J=5.0, 2.4, 0.6 Hz, 1H), 7.52-7.39 (m, 2H), 7.17 (ddd, J=4.2, 2.4, 0.6 Hz, 1H), 7.03 (t, J=4.9 Hz, 1H), 4.00 (s, 3H); LCMS (method B): 2.34 min (311.2, MH$^+$).

Example 61—1-(1-Methyl-1H-tetrazol-5-yl)-2-(pyridin-2-ylthio)-1H-benzo[d]imidazole 61

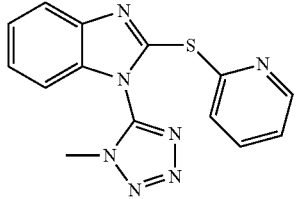 [SMILES: Cn1nnnc1-n1c(Sc2ccccn2)nc2ccccc21]

Using the method described in Example 60, substituting 2-mercaptopyrimidine with 2-mercaptopyridine, there was thus obtained 1-(1-methyl-1H-tetrazol-5-yl)-2-(pyridin-2-ylthio)-1H-benzo[d]imidazole 61 in 84% yield.

$^1$H NMR (500 MHz, CDCl$_3$) δ 8.27 (ddd, J=4.9, 1.9, 0.9 Hz, 1H), 7.95-7.87 (m, 1H), 7.62-7.54 (m, 1H), 7.48-7.38 (m, 2H), 7.32 (dt, J=8.0, 0.9 Hz, 1H), 7.15-7.07 (m, 2H), 4.01 (s, 3H); LCMS (method B): 2.41 min (310.2, MH$^+$).

Example 62—4-Chloro-1-(1-methyl-1H-tetrazol-5-yl)-2-((pyridin-2-ylmethyl)thio)-1H-benzo[d]imidazole 62

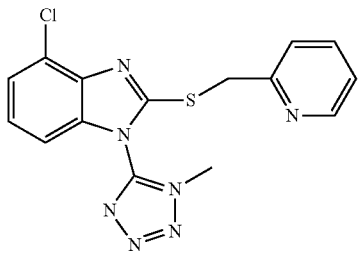

A solution of 3-chloro-N$^1$-(1-methyl-1H-tetrazol-5-yl)benzene-1,2-diamine G13 (45 mg, 0.20 mmol) in dry DMF (0.5 mL) was treated with TCDI (53 mg, 0.30 mmol) and stirred at 85° C. for 21 hours then cooled. Caesium carbonate (195 mg, 0.60 mmol) and 2-(chloromethyl)pyridine hydrochloride (46 mg, 0.28 mmol) were added and the mixture was stirred at RT for 5 hours then cooled, diluted with water (20 mL) and extracted with EtOAc (20 mL). The organics were washed with water (20 mL), dried (MgSO$_4$), chromatographed on silica eluting with 40-100% EtOAc/PE and triturated with DCM/PE to give 4-chloro-1-(1-methyl-1H-tetrazol-5-yl)-2-((pyridin-2-ylmethyl)thio)-1H-benzo[d]imidazole 62 (17 mg, 24%) as a pale pink solid.

$^1$H NMR (500 MHz, CDCl$_3$) δ 8.54 (d, J=4.2 Hz, 1H), 7.70 (dd, J=12.2, 4.6 Hz, 1H), 7.62 (d, J=7.8 Hz, 1H), 7.37 (dd, J=7.9, 0.8 Hz, 1H), 7.25-7.23 (m, 1H), 7.20 (t, J=8.0 Hz, 1H), 6.95 (dd, J=8.1, 0.8 Hz, 1H), 4.85 (s, 2H), 3.92 (s, 3H); LCMS (method B): 2.90 min (358.1, MH$^+$).

Example 63—N-(6-(((4-Chloro-1-(1-methyl-1H-tetrazol-5-yl)-1H-benzo[d]imidazol-2-yl)thio)methyl)pyridin-2-yl)cyclopropanecarboxamide 63

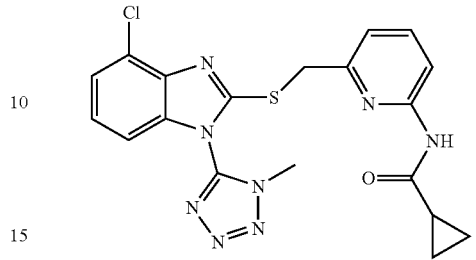

A solution of 3-chloro-N$^1$-(1-methyl-1H-tetrazol-5-yl)benzene-1,2-diamine G13 (44.5 mg, 0.198 mmol) in ethanol (2 mL) was treated with potassium ethylxanthate (96 mg, 0.60 mmol) and water (0.1 mL) then heated under reflux for 23 hours and cooled. A solution of (6-(cyclopropanecarboxamido)pyridin-2-yl)methyl methanesulfonate P1 (193 mg, 0.710 mmol) in DMF (2 mL) was added, followed by caesium carbonate (175 mg, 0.540 mmol) and the mixture was stirred for 40 min. Aqueous potassium carbonate solution (1M, 20 mL) was added and the mixture was extracted with EtOAc (20 mL). The organics were washed with water (3×20 mL) and brine, dried (MgSO$_4$) and chromatographed on silica eluting with 0-50% EtOAc/PE then triturated with DCM/PE and dried in vacuo overnight to give N-(6-(((4-chloro-1-(1-methyl-1H-tetrazol-5-yl)-1H-benzo[d]imidazol-2-yl)thio)methyl)pyridin-2-yl)cyclopropanecarboxamide 63 (42 mg, 48%) as a slightly gummy white solid.

$^1$H NMR (500 MHz, CDCl$_3$) δ 8.31 (s, 1H), 8.06 (d, J=8.3 Hz, 1H), 7.62 (t, J=7.9 Hz, 1H), 7.38 (dd, J=7.9, 0.9 Hz, 1H), 7.22 (t, J=8.0 Hz, 1H), 7.18 (d, J=7.4 Hz, 1H), 6.98 (dd, J=8.1, 0.9 Hz, 1H), 4.70 (s, 2H), 3.92 (s, 3H), 1.68-1.54 (m, 1H), 1.10-1.07 (m, 2H), 0.92-0.88 (m, 2H); LCMS (method B): 3.28 min (441.1, MH$^+$).

Example 64—6-Ethynyl-1-(1-methyl-1H-tetrazol-5-yl)-2-((pyridin-2-ylmethyl)thio)-1H-benzo[d]imidazole 64

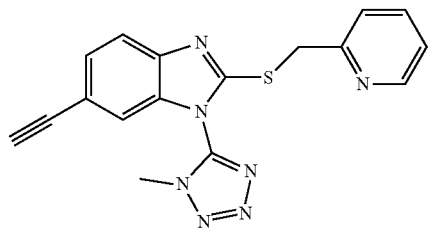 [SMILES: C#Cc1ccc2nc(SCc3ccccn3)n(-c3nnnn3C)c2c1]

TBAF (1M in THF) (0.05 mL, 0.05 mmol) was added to a solution of 1-(1-methyl-1H-tetrazol-5-yl)-2-((pyridin-2-ylmethyl)thio)-6-((trimethylsilyl)ethynyl)-1H-benzo[d]imidazole U (21 mg, 0.05 mmol) in dry THF (2 mL) at 0° C. The reaction mixture was stirred at 0° C. for 3.5 hours then diluted with EtOAc (20 mL), washed with water (3×20 mL) and brine, dried (MgSO$_4$) and concentrated in vacuo. The residue was chromatographed on silica, eluting with 0-100% EtOAc/PE to give 6-ethynyl-1-(1-methyl-1H-tetrazol-5-yl)-2-((pyridin-2-ylmethyl)thio)-1H-benzo[d]imidazole 64 (7 mg, 39%) as a white solid.

¹H NMR (500 MHz, CDCl₃) δ 8.55 (d, J=4.8 Hz, 1H), 7.69 (d, J=8.3 Hz, 2H), 7.54-7.47 (m, 2H), 7.24 (s, 1H), 7.18 (s, 1H), 4.81 (s, 2H), 3.94 (s, 3H), 3.08 (s, 1H); LCMS (method A): 2.55 min (348.3, MH⁺).

Example 65—N-(6-(((6-Ethynyl-1-(1-methyl-1H-tetrazol-5-yl)-1H-benzo[d]imidazol-2-yl)thio)methyl)pyridin-2-yl)-2,2-difluoro-2-phenoxyacetamide 65

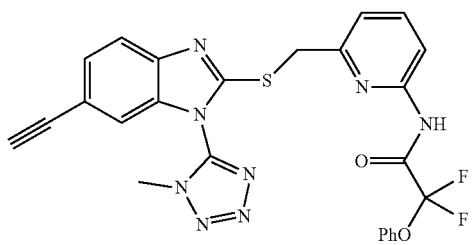 [SMILES: C#Cc1ccc2nc(SCc3cccc(NC(=O)C(F)(F)Oc4ccccc4)n3)n(-c3nnnn3C)c2c1]

Using the method described in Example 64, substituting Int. U with 2,2-difluoro-N-(6-(((6-iodo-1-(1-methyl-1H-tetrazol-5-yl)-1H-benzo[d]imidazol-2-yl)thio)methyl)pyridin-2-yl)-2-phenoxyacetamide U1, there was thus obtained N-(6-(((6-ethynyl-1-(1-methyl-1H-tetrazol-5-yl)-1H-benzo[d]imidazol-2-yl)thio)methyl)pyridin-2-yl)-2,2-difluoro-2-phenoxyacetamide 65 in 40% yield.

¹H NMR (500 MHz, CDCl₃) δ 8.96 (s, 1H), 8.17 (d, J=8.3 Hz, 1H), 7.75 (t, J=7.9 Hz, 1H), 7.69 (d, J=8.4 Hz, 1H), 7.49 (d, J=8.3 Hz, 1H), 7.41 (t, J=7.8 Hz, 2H), 7.30 (d, J=7.9 Hz, 4H), 7.18 (s, 1H), 4.69 (s, 2H), 3.95 (s, 3H), 3.08 (s, 1H); LCMS (method A): 3.46 min (533.2, MH⁺).

Using the method described in Example 1, substituting either or both of E or H with the appropriate electrophile "E" or benzimidazol-2-thione derivative "H", and with additional base if "E" was a salt, and DMF was generally used as solvent in place of THF, there were thus obtained the following Examples (thioethers, Ex. 66-86):

"E" + "H" →[Cs₂CO₃, DMF] Thioether

| Ex. | "E" | "H" | Yield | ¹H NMR δ(CDCl₃) | RTᵃ | Structure |
|-----|-----|-----|-------|-----------------|-----|-----------|
| 66 | P11 | H15 | 20% | 8.38 (d, J = 6.1 Hz, 1H), 7.73 (d, J = 1.8 Hz, 1H), 7.27-7.22 (m, 2H), 6.98 (d, J = 8.6 Hz, 1H), 6.87 (d, J = 4.1 Hz, 1H), 4.86 (s, 2H), 3.98 (s, 3H), 3.92 (s, 3H) | 2.90 (B) | 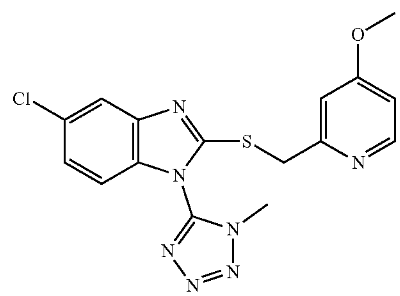 [SMILES: COc1ccnc(CSc2nc3cc(Cl)ccc3n2-c2nnnn2C)c1] |
| 67 | Cl-CH₂-pyridine·HCl | H15 | 38% | 8.55 (d, J = 4.2 Hz, 1H), 7.76-7.69 (m, 2H), 7.55 (d, J = 7.8 Hz, 1H), 7.29-7.26 (m, 1H), 7.25 (d, J = 1.9 Hz, 1H), 6.98 (d, J = 8.5 Hz, 1H), 4.82 (s, 2H), 3.94 (s, 3H) | 3.02 (B) | 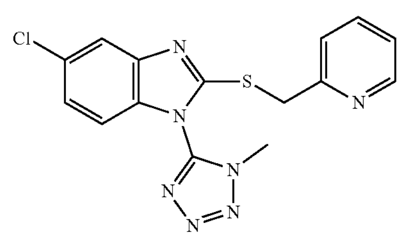 [SMILES: Cn1nnnc1-n1c(SCc2ccccn2)nc2cc(Cl)ccc21] |
| 68 | isoquinoline-CH₂Br·HBr | H | 45% | 8.43 (d, J = 5.8 Hz, 1H), 8.33 (d, J = 8.4 Hz, 1H), 7.87 (s, 1H), 7.81 (d, J = 8.1 Hz, 1H), 7.72-7.59 (m, 4H), 7.42-7.36 (m, 1H), 7.07 (d, J = 8.1 Hz, 1H), 5.43 (s, 2H), 3.97 (s, 3H) | 3.08 (B) | 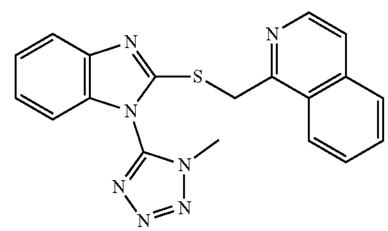 [SMILES: Cn1nnnc1-n1c(SCc2nccc3ccccc23)nc2ccccc21] |

-continued

"E" + "H" →(Cs₂CO₃, DMF) Thioether

| Ex. | "E" | "H" | Yield | ¹H NMR δ(CDCl₃) | RT$^a$ | Structure |
|---|---|---|---|---|---|---|
| 69 | P12 | H | 49% | 8.36 (s, 1H), 7.77 (d, J = 8.1 Hz, 1H), 7.46 (dd, J = 7.9, 1.8 Hz, 1H), 7.41-7.33 (m, 2H), 7.31-7.27 (m, 1H), 7.05 (d, J = 8.0 Hz, 1H), 4.76 (s, 2H), 3.92 (s, 3H), 2.31 (s, 3H) | 2.57 (B) | 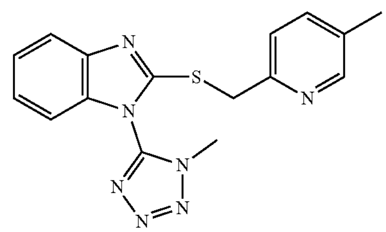 [SMILES: Cc1ccc(CSc2nc3ccccc3n2-c2nnnn2C)nc1] |
| 70 | P13 | H | 12% | 8.72 (d, J = 5.0 Hz, 1H), 7.85 (s, 1H), 7.78 (d, J = 8.1 Hz, 1H), 7.44 (d, J = 6.4 Hz, 1H), 7.39 (t, J = 7.7 Hz, 1H), 7.33-7.28 (m, 1H), 7.05 (d, J = 8.0 Hz, 1H), 4.80 (s, 2H), 3.96 (s, 3H) | 2.90 (B) | 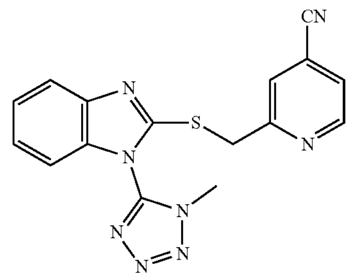 [SMILES: Cn1nnnc1-n1c(SCc2cc(C#N)ccn2)nc2ccccc21] |
| 71 | | H | 55% | 8.10 (d, J = 4.7 Hz, 1H), 7.81-7.77 (m, 1H), 7.39-7.33 (m, 1H), 7.31-7.26 (m, 1H), 7.24 (d, J = 4.7 Hz, 1H), 7.20 (d, J = 8.1 Hz, 1H), 7.08-7.04 (m, 1H), 4.87 (s, 2H), 3.98 (s, 3H), 3.83 (s, 3H) | 2.65 (B) | 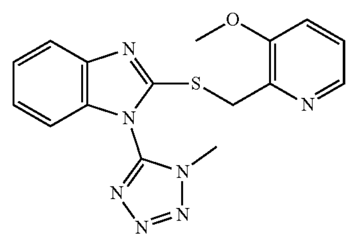 [SMILES: COc1cccnc1CSc1nc2ccccc2n1-c1nnnn1C] |
| 72$^b$ | | H | 45% | 7.82-7.78 (m, 2H), 7.74 (d, J = 8.0 Hz, 1H), 7.63-7.57 (m, 1H), 7.39-7.35 (m, 1H), 7.32-7.28 (m, 1H), 7.06 (d, J = 8.1 Hz, 1H), 4.78 (s, 2H), 4.00 (s, 3H) | 2.96 (B) | |
| 73 | P14 | H | 35% | 8.22 (s, 1H), 7.77 (d, J = 8.0 Hz, 1H), 7.49 (d, J = 8.6 Hz, 1H), 7.37 (t, J = 7.7 Hz, 1H), 7.28 (t, J = 6.8 Hz, 1H), 7.20 (d, J = 8.5 Hz, 1H), 7.05 (d, J = 8.0 Hz, 1H), 4.77 (s, 2H), 3.93 (s, 3H), 3.85 (s, 3H) | 2.65 (B) | 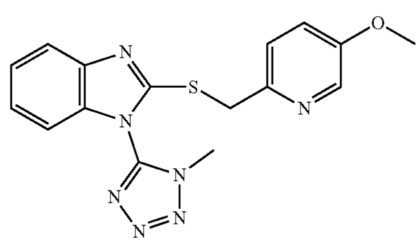 [SMILES: COc1ccc(CSc2nc3ccccc3n2-c2nnnn2C)nc1] |
| 74$^b$ | | H | 11% | 8.80 (s, 1H), 7.92 (d, J = 8.1 Hz, 1H), 7.75 (d, J = 8.0 Hz, 1H), 7.72 (d, J = 8.1 Hz, 1H), 7.37 (d, J = 11.2 Hz, 1H), 7.33-7.28 (m, 1H), 7.07-7.02 (m, 1H), 4.79 (s, 2H), 3.96 (s, 3H) | 2.90 (B) | |

-continued $$\text{"E"} + \text{"H"} \xrightarrow{\text{Cs}_2\text{CO}_3, \text{DMF}} \text{Thioether}$$

| Ex. | "E" | "H" | Yield | ¹H NMR δ(CDCl₃) | RT[a] | Structure |
|---|---|---|---|---|---|---|
| 75 | P15 | H | 56% | 8.60 (s, 1H), 7.81-7.74 (m, 2H), 7.47 (d, J = 8.3 Hz, 1H), 7.37 (dd, J = 9.7, 5.7 Hz, 1H), 7.29 (dd, J = 13.8, 6.5 Hz, 1H), 7.05 (d, J = 8.0 Hz, 1H), 4.73 (s, 2H), 3.94 (s, 3H) | 3.28 (B) | 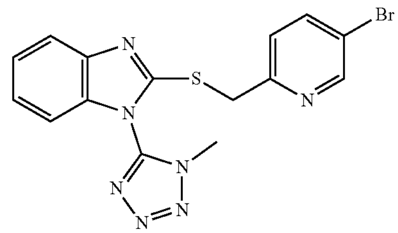 [SMILES: Cn1nnnc1-n1c(SCc2ccc(Br)cn2)nc2ccccc21] |
| 76 | (2-(chloromethyl)-5-cyanopyridine) | H | 68% | 8.49 (s, 1H), 7.76 (d, J = 8.1 Hz, 1H), 7.64 (d, J = 8.3 Hz, 1H), 7.52 (d, J = 8.3 Hz, 1H), 7.40-7.34 (m, 1H), 7.32-7.27 (m, 1H), 7.05 (d, J = 8.0 Hz, 1H), 4.76 (s, 2H), 3.94 (s, 3H) | 3.14 (B) | 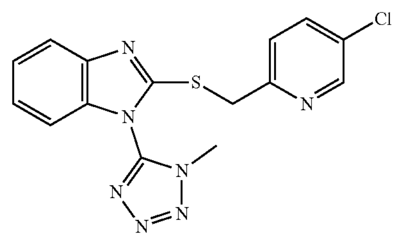 [SMILES: Cn1nnnc1-n1c(SCc2ccc(Cl)cn2)nc2ccccc21] |
| 77[b] | P16 | H | 3% | 8.36 (s, 1H), 7.78 (d, J = 8.1 Hz, 1H), 7.73 (s, 1H), 7.41-7.35 (m, 1H), 7.30 (t, J = 7.7 Hz, 1H), 7.06 (d, J = 8.1 Hz, 1H), 4.91 (s, 2H), 3.99 (s, 3H) | 3.61 (B) | 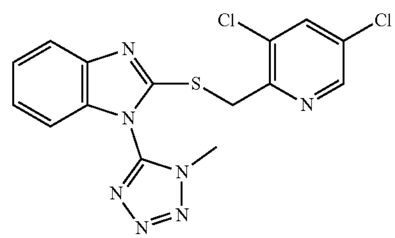 [SMILES: Cn1nnnc1-n1c(SCc2ncc(Cl)cc2Cl)nc2ccccc21] |
| 78[b] | P17 | H | 9% | 8.73 (s, 1H), 7.82 (s, 1H), 7.77 (d, J = 8.0 Hz, 1H), 7.44 (d, J = 4.9 Hz, 1H), 7.40-7.35 (m, 1H), 7.32-7.27 (m, 2H), 7.07-7.02 (m, 1H), 4.83 (s, 2H), 3.95 (s, 3H) | 3.26 (B) | 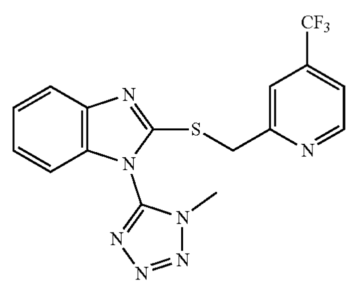 |
| 79 | (2-(chloromethyl)-4-chloropyridine·HCl) | H | 13% | 8.44 (d, J = 5.4 Hz, 1H), 7.78 (d, J = 8.0 Hz, 1H), 7.60 (s, 1H), 7.38 (t, J = 7.7 Hz, 1H), 7.29 (t, J = 7.3 Hz, 1H), 7.26-7.21 (m, 1H), 7.07-7.03 (m, 1H), 4.77 (s, 2H), 3.94 (s, 3H) | 3.12 (B) | 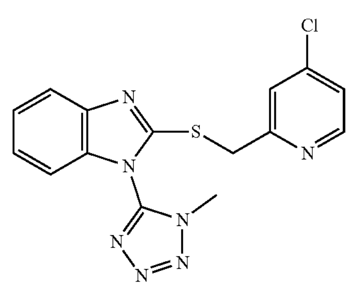 [SMILES: Cn1nnnc1-n1c(SCc2cc(Cl)ccn2)nc2ccccc21] |
| 80 | (2-(chloromethyl)-3-chloropyridine) | H | 50% | 8.34 (s, 1H), 7.67 (d, J = 3.2 Hz, 2H), 7.57-7.51 (m, 1H), 7.28 (d, J = 7.2 Hz, 1H), 7.21 (dd, J = 12.9, 5.4 Hz, 1H), 7.05 (s, 1H), 4.91-4.84 (m, 2H), 3.97-3.89 (m, 3H) | 3.24 (B) | 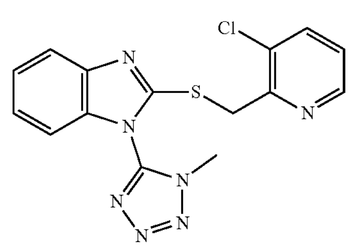 [SMILES: Cn1nnnc1-n1c(SCc2ncccc2Cl)nc2ccccc21] |

-continued

"E" + "H" $\xrightarrow{Cs_2CO_3, DMF}$ Thioether

| Ex. | "E" | "H" | Yield | $^1$H NMR δ(CDCl$_3$) | RT$^a$ | Structure |
|---|---|---|---|---|---|---|
| 81$^c$ | P1 | H16 | 32% | 8.38 (br s, 1H), 8.08-8.00 (m, 1H), 7.67 (d, J = 8.0 Hz, 1H), 7.61 (t, J = 7.7 Hz, 1H), 7.29 (dd, J = 8.5, 7.5 Hz, 1H), 7.21 (dd, J = 14.3, 7.0 Hz, 1H), 7.12 (d, J = 7.3 Hz, 1H), 4.64 (ABq, J = 24.0, 13.9 Hz, 2H), 3.89 (s, 3H), 1.62-1.56 (m, 1H), 1.13-1.02 (m, 2H), 0.92-0.79 (m, 2H) | 3.27 (B) | |
| 82 | Cl-CH$_2$-pyridine·HCl | H16 | 68% | 8.53 (br d, J = 4.3 Hz, 1H), 7.71-7.63 (m, 2H), 7.49 (d, J = 7.8 Hz, 1H), 7.29 (t, J = 8.0 Hz, 1H), 7.24-7.18 (m, 2H), 4.77 (ABq, J = 49.7, 13.7 Hz, 2H), 3.88 (s, 3H) | 3.19 (A) | 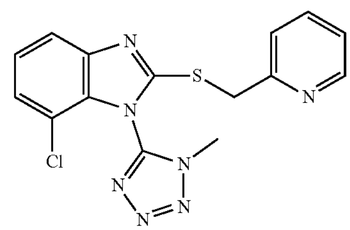 [SMILES: Cn1nnnc1-n1c(SCc2ccccn2)nc2cccc(Cl)c21] |
| 83 | P18 | H16 | 75% | 7.83 (d, J = 8.3 Hz, 1H), 7.67 (dd, J = 8.0, 0.9 Hz, 1H), 7.60 (t, J = 7.9 Hz, 1H), 7.29 (t, J = 8.0 Hz, 1H), 7.21 (dd, J = 8.0, 0.9 Hz, 1H), 7.08 (d, J = 7.5 Hz, 1H), 4.62 (ABq, J = 37.8, 13.6 Hz, 2H), 3.86 (s, 3H), 1.50 (s, 9H) | 3.79 (B) | 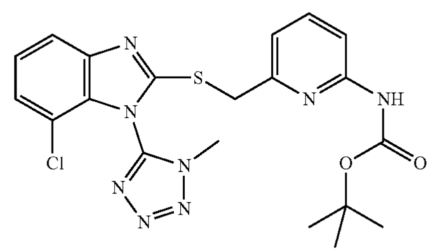 [SMILES: Cn1nnnc1-n1c(SCc2cccc(NC(=O)OC(C)(C)C)n2)nc2cccc(Cl)c21] |
| 84 | P18 | H17 | 49% | 7.82 (d, J = 8.2 Hz, 1H), 7.58 (t, J = 7.8 Hz, 1H), 7.02 (d, J = 7.4 Hz, 1H), 6.60 (dd, J = 11.4, 2.1 Hz, 1H), 6.40 (dd, J = 7.6, 2.1 Hz, 1H), 4.64 (s, 2H), 4.06 (s, 3H), 3.89 (s, 3H), 1.51 (s, 9H) | 3.59 (B) | 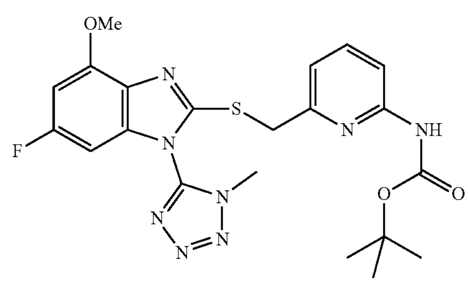 [SMILES: COc1cc(F)cc2c1nc(SCc1cccc(NC(=O)OC(C)(C)C)n1)n2-c1nnnn1C] |
| 85$^d$ | Cl-CH$_2$-pyridine·HCl | H17 | 50% | 8.52 (dd, J = 4.8, 0.7 Hz, 1H), 7.64 (td, J = 7.7, 1.8 Hz, 1H), 7.41 (d, J = 7.8 Hz, 1H), 7.23-7.16 (m, 1H), 6.60 (dd, J = 11.4, 2.1 Hz, 1H), 6.39 (dd, J = 7.7, 2.1 Hz, 1H), 4.79 (s, 2H), 4.06 (s, 3H), 3.91 (s, 3H) | 2.99 (A) | |

-continued

| Ex. | "E" | "H" | Yield | $^1$H NMR δ(CDCl$_3$) | RT$^a$ | Structure |
|---|---|---|---|---|---|---|
| 86$^e$ | P18 | H13 | 76% | 7.85 (d, J = 7.9 Hz, 1H), 7.62 (t, J = 7.7 Hz, 1H), 7.37 (dd, J = 7.9, 0.8 Hz, 1H), 7.30 (br s, 1H), 7.20 (t, J = 8.0 Hz, 1H), 7.17 (br s, 1H), 6.95 (dd, J = 8.1, 0.9 Hz, 1H), 4.70 (s, 2H), 3.90 (s, 3H), 1.51 (s, 9H) | 3.94 (B) | |

$^a$RT = LCMS retention time in minutes using indicated Method (A-D or F);
$^b$Potassium carbonate was used instead of caesium carbonate;
$^c$Purity ca. 75% by LCMS;
$^d$Sodium hydrogen carbonate (2.3 equiv.) was used as base (4 h) then caesium carbonate (1 equiv.) was added and reaction quenched after a further 2.5 h;
$^e$Sodium hydrogen carbonate (1.2 equiv.) was used as base, with reaction at RT for 18 h.

Example 87—6-(((4-Chloro-1-(1-methyl-1H-tetrazol-5-yl)-1H-benzo[d]imidazol-2-yl)thio)methyl)pyridin-2-amine

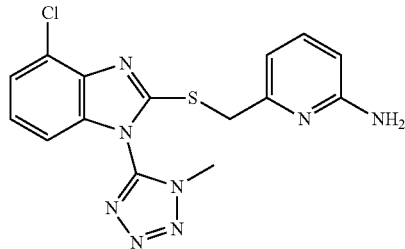 [SMILES: Cn1nnnc1-n1c(SCc2cccc(N)n2)nc2c(Cl)cccc21]

Following the method described in Example 26, using 2-(6-(((4-chloro-1-(1-methyl-1H-tetrazol-5-yl)-1H-benzo[d]imidazol-2-yl)thio)methyl)pyridin-2-yl)isoindoline-1,3-dione O1 in place of O, there was thus obtained 6-(((4-chloro-1-(1-methyl-1H-tetrazol-5-yl)-1H-benzo[d]imidazol-2-yl)thio)methyl)pyridin-2-amine in 73% yield.

$^1$H NMR (500 MHz, CDCl$_3$) δ 7.38 (ddd, J=8.8, 8.1, 4.1 Hz, 2H), 7.20 (t, J=8.0 Hz, 1H), 6.96 (dd, J=8.1, 0.8 Hz, 1H), 6.85 (d, J=7.3 Hz, 1H), 6.43 (d, J=8.3 Hz, 1H), 4.75 (br s, 2H), 4.65 (s, 2H), 3.92 (s, 3H); LCMS (method B): 2.70 min (373.1, MH$^+$).

Example 88—N-Benzyl-6-(((1-(1-methyl-1H-tetrazol-5-yl)-1H-benzo[d]imidazol-2-yl)thio)methyl)pyridin-2-amine

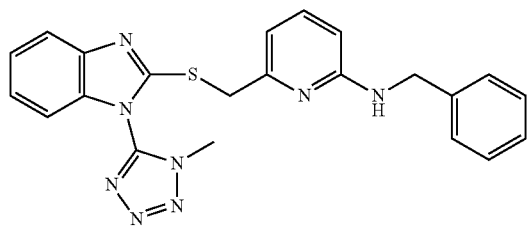 [SMILES: Cn1nnnc1-n1c(SCc2cccc(NCc3ccccc3)n2)nc2ccccc21]

A solution of Example 26 (20 mg, 0.059 mmol) and benzaldehyde (6.0 µL, 0.06 mmol) in MeOH (1 mL) was treated with sodium cyanoborohydride (9.3 mg, 0.15 mmol) and acetic acid (1 drop). The reaction mixture was stirred at RT for 18 hours. The reaction was quenched with a saturated aq. solution of ammonium chloride (10 mL) and water (5 mL) and extracted into DCM (20 mL). Organics were washed with brine, dried (MgSO$_4$) and evaporated in vacuo. The residue was chromatographed on silica eluting with 0-100% EtOAc/PE, to give N-benzyl-6-(((1-(1-methyl-1H-tetrazol-5-yl)-1H-benzo[d]imidazol-2-yl)thio)methyl)pyridin-2-amine 88 (17 mg, 67% yield) as a gum which was triturated with DCM/PE to give a white foam.

$^1$H NMR (500 MHz, CDCl$_3$) δ 7.77 (d, J=8.0 Hz, 1H), 7.39-7.27 (m, 8H), 7.05 (dd, J=8.1, 0.8 Hz, 1H), 6.70 (d, J=7.3 Hz, 1H), 6.29 (d, J=8.4 Hz, 1H), 4.62 (s, 2H), 4.45 (d, J=5.9 Hz, 2H), 3.86 (s, 3H); LCMS (method B): 3.31 min (429.3, MH$^+$).

Example 89—N-(Cyclopropylmethyl)-6-(((1-(1-methyl-1H-tetrazol-5-yl)-1H-benzo[d]imidazol-2-yl)thio)methyl)pyridin-2-amine

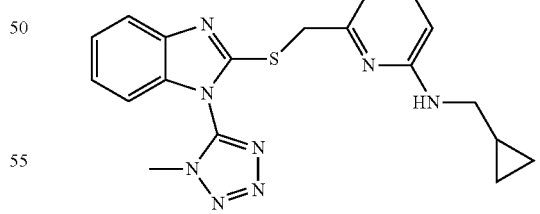

Following the method described in Example 88, using cyclopropanecarboxaldehyde (11 µL, 0.15 mmol) in place of benzaldehyde, there was thus obtained N-(cyclopropylmethyl)-6-(((1-(1-methyl-1H-tetrazol-5-yl)-1H-benzo[d]imidazol-2-yl)thio)methyl)pyridin-2-amine 89 (26 mg, 50% yield) as an off white gum.

$^1$H NMR (500 MHz, CDCl$_3$) δ 7.77 (d, J=8.0 Hz, 1H), 7.47 (d, J=8.2 Hz, 1H), 7.39-7.35 (m, 1H), 7.29 (t, J=7.7 Hz, 1H), 7.05 (dd, J=7.3, 0.7 Hz, 1H), 6.79-6.69 (m, 1H), 6.52-6.33 (m, 1H), 4.66 (s, 2H), 3.97 (s, 3H), 3.09 (t, J=5.9 Hz, 2H), 1.11-1.04 (m, 1H), 0.59 (q, J=4.8 Hz, 2H), 0.27 (q, J=4.9 Hz, 2H); LCMS (method B): 3.14 min (393.2, MH⁺).

Example 90—6-(((4-Chloro-1-(1-methyl-1H-tetrazol-5-yl)-1H-benzo[d]imidazol-2-yl)thio)methyl)-N-(cyclopropylmethyl)pyridin-2-amine

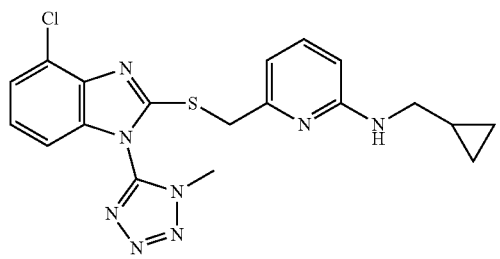 [SMILES: Cn1nnnc1-n1c(SCc2cccc(NCC3CC3)n2)nc2c(Cl)cccc21]

Following the method described in Example 89, but using Example 87 (10 mg, 0.027 mmol) in place of 26, there was thus obtained 6-(((4-chloro-1-(1-methyl-1H-tetrazol-5-yl)-1H-benzo[d]imidazol-2-yl)thio)methyl)-N-(cyclopropylmethyl)pyridin-2-amine 90 (8 mg, 62% yield) as a colourless gum.

$^1$H NMR (500 MHz, CDCl$_3$) δ 7.44 (br s, 1H), 7.37 (dd, J=7.9, 0.8 Hz, 1H), 7.20 (t, J=8.0 Hz, 1H), 6.96 (dd, J=8.1, 0.8 Hz, 1H), 6.79 (br s, 1H), 6.36 (br s, 1H), 4.68 (s, 2H), 3.94 (s, 3H), 3.13-3.00 (m, 2H), 1.11-1.01 (m, 1H), 0.56 (d, J=5.5 Hz, 2H), 0.25 (d, J=4.3 Hz, 2H); LCMS (method F): 1.42 min (427.3, MH⁺).

Example 91—Testing the Fungicidal Activity of Compounds of the Invention

The activity of compounds of the invention was assessed by testing against certain oomycete plant pathogens and representative data are presented in Table 1.

Amended Agar Assay

Testing was carried out on potato dextrose agar (PDA) amended with each compound at a test concentration of 20 ppm. Amended agar was poured into three replicate 9 cm petri dishes. Each replicate dish was inoculated in the centre with a 5 mm agar plug taken from the leading edge of a culture aged between 2 and 7 days old; the age of the culture was dependant on the growth rate of the pathogen being tested. The test pathogens were *Pythium ultimum* and *Phytophthora cinnamomi*. Plates were incubated at 18° C. and the diameter of each colony measured before growth on the fastest growing plate reached the plate edge. This varied between 2 and 7 days depending on the growth rate of test pathogens. The % reduction in colony growth compared to the control plate was calculated for each pathogen. The results are provided in Table 1, in which D represents no control detected at this concentration; C represents up to 50% control; B from 50 to 99% control; and A represents a control of greater than 99%, i.e. no detectable colony growth.

Alternatively, or in addition, the same assay was conducted at descending test concentrations with 5-fold dilutions typically down to 0.032 ppm though sometimes as low as 0.00026 ppm, and an EC$_{50}$ (the concentration at which 50% control would be achieved) was determined. The results are provided in Table 1 in which G represents an EC$_{50}$ above 20 ppm, F represents an EC$_{50}$ of 1-20 ppm and E represents and EC$_{50}$ less than 1 ppm.

96 Well Plate Test

Compounds were screened in 96 well plates with 10 compounds per plate. Each compound was screened using agar amended to 20, 2, 0.2 and 0.02 ppm, with Proline at 50 and 10 ppm and 0.2% DMSO used as controls. Each test concentration and standard was replicated twice on a plate. Compounds were screened against *Phytophthora cactorum*. The agar used in the test is a 1% PDA. 1000 spores/mL agar were added to the appropriate agar.

A ×10 stock solution in 2% DMSO was produced for each dose i.e. 200, 20, 2 and 0.2 ppm, and 10 μl of this added to the appropriate wells on the plate. An equivalent amount of 2% DMSO and Proline stock at 500 and 100 ppm were added for the controls. To each well 90 μl of the appropriate agar spore suspension was added to give the required final well concentrations. Plates were incubated at room temperature (18° C.) and assessed after 2 to 3 days. The amount of pathogen growth in each well was compared to the DMSO controls and an EC$_{50}$ concentration was calculated. The results are provided in Table 1 in which G represents an EC$_{50}$ above 20 ppm, F represents an EC$_{50}$ of 1-20 ppm and E represents an EC$_{50}$ less than 1 ppm.

TABLE 1

| | % control or EC$_{50}$ | | | | |
| | *Pythium ultimum* | | | *Phytophthora* spp. | |
| Compound | 20 ppm | 2 ppm | EC$_{50}$ | 20 ppm | EC$_{50}$ |
|---|---|---|---|---|---|
| 1 | A | | E | A | E |
| 2 | A | A | F | B | E |
| 3 | A | | | A | |
| 4 | | | F | | F |
| 5 | C | | | C | |
| 6 | B | | | B | |
| 7 | | | E | | E |
| 8 | | B | E | | E |
| 9 | | | E | | E |
| 10 | B | | | C | |
| 11 | | | E | | E |
| 12 | | | E | | E |
| 13 | C | | G | D | G |
| 14 | C | | | C | |
| 15 | C | | G | D | G |
| 16 | A | | F | B | F |
| 17 | A | | E | A | E |
| 18 | C | | | D | |
| 19 | B | | | B | |
| 20 | C | | G | D | G |
| 21 | A | | E | A | E |
| 22 | | | E | | E |
| 23 | | | E | | E |
| 24 | C | | | B | |
| 25 | | B | E | | E |
| 26 | A | | | A | |
| 27 | A | | | B | |
| 28 | | | E | | E |
| 29 | D | | | C | |
| 30 | D | | G | D | G |
| 31 | C | | G | | G |
| 32 | D | | | D | |
| 33 | D | | G | D | G |
| 34 | A | B | | | F* |
| 35 | | B | | | F* |
| 36 | | B | | | G* |
| 37 | A | B | | | F* |
| 38 | | A | | | F* |
| 39 | | A | | | F* |
| 40 | | B | | | F* |
| 41 | | A | | | F* |
| 42 | | A | | | F* |
| 43 | D | | | | G* |

TABLE 1-continued

| | % control or EC$_{50}$ | | | | |
|---|---|---|---|---|---|
| | Pythium ultimum | | | Phytophthora spp. | |
| Compound | 20 ppm | 2 ppm | EC$_{50}$ | 20 ppm | EC$_{50}$ |
| 44 | | D | | | G* |
| 45 | | | E | | E |
| 46 | D | | | C | |
| 47 | | A | | | E* |
| 48 | | A | | | F* |
| 49 | A | | F | B | F |
| 50 | | | E | | E |
| 51 | | D | | | G* |
| 52 | B | | F | B | E |
| 53 | | | E | | E |
| 55 | | C | | | G* |
| 56 | | C | | | G* |
| 57 | | C | | | G* |
| 58 | | C | | | G* |
| 59 | A | A | B | A | F* |
| 60 | | C | | | G* |
| 61 | | D | | | G* |
| 62 | | A | | | E* |
| 63 | | A | | | F* |
| 64 | | C | | | G* |
| 65 | | B | | | G* |
| 66 | | A | | | F* |
| 67 | | A | | | F* |
| 68 | | B | | | G* |
| 69 | | A | | | F* |
| 70 | | A | | | G* |
| 71 | | C | | | G* |
| 72 | | D | | | G* |
| 73 | | A | | | F* |
| 74 | | C | | | G* |
| 75 | | A | | | F* |
| 76 | | A | | | F* |
| 77 | | B | | | G* |
| 78 | | A | | | F* |
| 81 | | | | | G* |
| 82 | | B | | | G* |
| 83 | | B | | | F* |
| 84 | | A | | | F* |
| 85 | | A | | | G* |
| 88 | | A | | | E* |

*Compound was tested in 96 well plate format vs. Phytophthora cactorum

Thus many of the compounds of the invention showed good to excellent control over the pathogens tested (e.g. examples 1, 2, 3, 7, 8, 9, 11, 12, 16, 17, 21, 22, 23, 25, 26, 27, 28, 34, 37, 38, 39, 40, 41, 42, 45, 47, 48, 49, 50, 52, 53, 59, 62, 63, 66, 67, 69, 70, 73, 75, 76, 78, 83, 84, 88).

The invention claimed is:
1. A compound of formula (I):

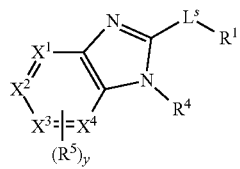

wherein -L$^S$- is independently —(CR$^2$R$^3$)$_n$—S—(CR$^2$R$^3$)$_n$—;
wherein X$^1$, X$^2$, X$^3$ and X$^4$ are each selected from carbon and nitrogen; wherein no more than three of X$^1$, X$^2$, X$^3$ and X$^4$ are nitrogen;
R$^1$ is independently selected from C(O)OR$^6$, C(O)NR$^7$R$^8$, and 5-, 6-, 9- or 10-membered heteroaryl group, wherein said heteroaryl group is optionally substituted with a single R$^9$ group and/or from 1 to 5 R$^{10}$ groups;
R$^2$ and R$^3$ are each independently selected from H, F, C$_1$-C$_4$-alkyl and C$_1$-C$_4$-haloalkyl;
or R$^2$ and R$^3$ together with the carbon to which they are attached form a C$_3$-C$_5$-cycloalkyl group;
R$^4$ is independently selected from 5- or 6-membered heteroaryl, further substituted with from 1 to 4 R$^{11}$ groups; wherein R$^4$ is substituted at a position adjacent to the point of connection of R$^4$ to the rest of the molecule with an R$^{11b}$ group, wherein R$^{11b}$ is selected from chloro, bromo, C$_1$-C$_4$-alkyl, C$_2$-C$_4$-alkenyl, C$_2$-C$_4$-alkynyl, phenyl, C$_3$-C$_6$-cycloalkyl, 3- to 6-membered heterocycloalkyl, 5- or 6-membered heteroaryl and C$_1$-C$_4$-haloalkyl;
R$^5$, R$^{10}$ and R$^{11}$ are each independently at each occurrence selected from: halo, nitro, cyano, NR$^{12}$R$^{13}$, NR$^{12}$S(O)$_2$R$^{12}$, NR$^{12}$C(O)R$^{12}$, NR$^{12}$CONR$^{12}$R$^{12}$, NR$^{12}$CO$_2$R$^{12}$, OR$^{12a}$, SR$^{12}$, S(O)R$^{12}$, OS(O)$_2$R$^{12}$, S(O)$_2$R$^{12}$, S(O)$_2$NR$^{12}$R$^{12}$, CO$_2$R$^{12}$, C(O)R$^{12}$, CONR$^{12}$R$^{12}$, C$_1$-C$_6$-alkyl, C$_2$-C$_6$-alkenyl, C$_2$-C$_6$-alkynyl, C$_1$-C$_6$-haloalkyl, phenyl, C$_3$-C$_6$-cycloalkyl, 3- to 6-membered heterocycloalkyl, 5- or 6-membered heteroaryl, and —O—C$_1$-C$_4$-haloalkyl;
R$^6$ is independently selected from C$_1$-C$_6$-alkyl, C$_1$-C$_6$-haloalkyl, C$_3$-C$_6$-alkenyl, C$_3$-C$_6$-alkynyl, and C$_0$-C$_3$-alkylene-R$^{14}$; wherein R$^{14}$ is independently selected from: C$_3$-C$_6$-cycloalkyl, 4- to 7-membered heterocycloalkyl, phenyl, 5- or 6-membered heteroaryl and —O—C$_1$-C$_4$-alkyl;
R$^7$ is independently selected from H, C$_1$-C$_6$-alkyl, C$_1$-C$_6$-haloalkyl, C$_3$-C$_6$-alkenyl, C$_3$-C$_6$-alkynyl, and C$_0$-C$_3$-alkylene-R$^{14}$; wherein R$^{14}$ is independently selected from: C$_3$-C$_6$-cycloalkyl, 4- to 7-membered heterocycloalkyl, phenyl, 5- or 6-membered heteroaryl and —O—C$_1$-C$_4$-alkyl;
R$^8$, R$^{12}$, R$^{15}$, R$^{18}$ and R$^{22}$ are each independently at each occurrence selected from H, C$_1$-C$_6$-alkyl and C$_3$-C$_6$-cycloalkyl;
or R$^7$ and R$^8$ together with the nitrogen to which they are attached form a 4- to 7-membered heterocycloalkyl ring;
or where two R$^{12}$ groups are attached to the same nitrogen atom, the two R$^{12}$ groups together with the nitrogen atom to which they are attached may form a 4- to 7-membered heterocycloalkyl ring;
R$^9$ is NR$^{15}$R$^{16}$;
R$^{12a}$ is independently at each occurrence selected from H, C$_1$-C$_6$-alkyl, C$_1$-C$_6$-haloalkyl, and C$_3$-C$_6$-cycloalkyl;
R$^{13}$ is independently at each occurrence selected from H, C$_3$-C$_6$-cycloalkyl, C$_1$-C$_6$-alkyl, C(O)—C$_1$-C$_6$-alkyl, C(O)O—C$_1$-C$_6$-alkyl and S(O)$_2$—C$_1$-C$_6$-alkyl;
or R$^{13}$ and R$^{12}$ together with the carbon to which they are attached form a 4 to 7-membered heterocycloalkyl ring;
R$^{16}$ is independently selected from: H, C$_1$-C$_6$-alkyl, C$_3$-C$_7$-cycloalkyl, C$_1$-C$_4$-alkylene-R$^{16a}$, 4 to 7-membered heterocycloalkyl, 5-, 6-, 9 or 10-membered heteroaryl, C(S)-L-R$^{17}$ and C(O)-L$^1$-R$^{17}$;
R$^{16a}$ is independently selected from: C$_3$-C$_6$-cycloalkyl, 4- to 7-membered heterocycloalkyl, phenyl, 5- or 6-membered heteroaryl, —C$_0$-C$_3$-alkylene-C$_3$-C$_6$-cycloalkyl and —O—C$_1$-C$_4$-alkyl;
-L$^1$- is absent or is independently selected from —O—, —S—, and -NR$^{18}$-;
R$^{17}$ is independently selected from C$_1$-C$_8$-alkyl, C$_1$-C$_8$-haloalkyl, C$_3$-C$_8$-alkenyl, C$_3$-C$_8$-alkynyl, C$_0$-C$_3$-alkylene-R$^{19}$; and —CR$^{20}$R$^{20}$L$^2$R$^{21}$;

-L²- is independently selected from —O—, —S— and —NR²²;

R²⁰ is independently at each occurrence selected from F, H and $C_1$-$C_4$-alkyl;

R²¹ is independently selected from H, $C_1$-$C_8$-alkyl, $C_1$-$C_8$-haloalkyl, $C_2$-$C_8$-alkenyl, $C_2$-$C_8$-alkynyl and $C_0$-$C_3$-alkylene-$R^{23}$;

R¹⁹ and R²³ are each independently at each occurrence selected from $C_3$-$C_6$-cycloalkyl, 3- to 6-membered heterocycloalkyl, 5- or 6-membered heteroaryl and phenyl;

y is an integer selected from 0, 1, 2, 3 and 4;

n is independently at each occurrence an integer selected from 0, 1 and 2;

wherein where any R¹-R² group is or forms part of an alkyl, alkenyl, alkynyl, haloalkyl, cycloalkyl, heterocycloalkyl, phenyl or heteroaryl group, that alkyl, haloalkyl, cycloalkyl, heterocycloalkyl, phenyl or heteroaryl group is optionally substituted, where chemically possible, by 1 to 5 substituents which are each independently selected at each occurrence from: oxo, =NRᵃ, =NORᵃ, halo, nitro, cyano, NRᵃRᵇ, NRᵃS(O)₂Rᵃ, NRᵃC(O)Rᵃ, NRᵃCONRᵃRᵃ, NRᵃCO₂Rᵃ, ORᵃ, SRᵃ, S(O)Rᵃ, S(O)₂Rᵃ, S(O)₂NRᵃRᵃ, CO₂Rᵃ C(O)Rᵃ, CONRᵃRᵃ, $C_1$-$C_4$-alkyl, $C_2$-$C_4$-alkenyl, $C_2$-$C_4$-alkynyl and $C_1$-$C_4$-haloalkyl; wherein Rᵃ is independently at each occurrence selected from H and $C_1$-$C_4$ alkyl; and Rᵇ is independently at each occurrence selected from H, $C_3$-$C_6$-cycloalkyl, $C_1$-$C_4$-alkyl, C(O)—$C_1$-$C_4$-alkyl and S(O)₂—$C_1$-$C_4$-alkyl;

or an agronomically acceptable salt or N-oxide thereof.

2. A compound of claim 1, wherein $L^s$ is —S—(CR²R³)—.

3. A compound of claim 1, wherein each of X¹, X², X³ and X⁴ is carbon.

4. A compound of claim 1, wherein a single one of X¹, X², X³ and X⁴ is nitrogen.

5. A compound of claim 1, wherein R¹ is a 5- or 6-membered heteroaryl group having a nitrogen atom in the ring neighbouring the carbon through which R¹ is connected to the rest of the molecule.

6. A compound of claim 5, wherein R¹ has the structure:

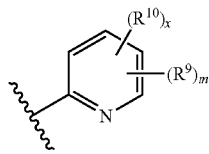

wherein x is an integer selected from 0, 1, 2, 3 and 4; and m is an integer selected from 0 and 1.

7. A compound of claim 6, wherein R¹ has the structure:

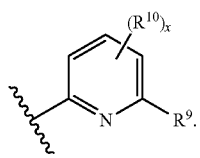

8. A compound of claim 5, wherein R¹ has the structure

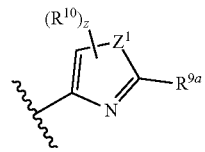

wherein Z is independently selected from O and S; $R^{9a}$ is either absent or is $NR^{15}R^{16}$; and wherein z is an integer independently selected from 0, 1 and 2.

9. A compound of claim 8, wherein R¹ has the structure

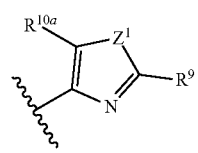

wherein Z is independently selected from O and S; $R^{10a}$ is independently selected from: H, halo, nitro, cyano, NR¹²R¹³, NR¹²S(O)₂R¹², NR¹²C(O)R¹², NR¹²CONR¹²R¹², NR¹²CO₂R¹², OR¹²a SR¹², S(O)R¹², OS(O)₂R¹², S(O)₂R¹², S(O)₂NR¹²R¹², CO₂R¹², C(O)R¹², CONR¹²R¹², $C_1$-$C_4$-alkyl, $C_2$-$C_4$-alkenyl, $C_2$-$C_4$-alkynyl, phenyl, $C_3$-$C_6$-cycloalkyl, 3- to 6-membered heterocycloalkyl, 5- or 6-membered heteroaryl and $C_1$-$C_4$-haloalkyl.

10. A compound of claim 8, wherein $Z^1$ is S.

11. A compound of claim 1, wherein R¹⁶ is selected from C(S)—L¹—R¹⁷ and C(O)—L¹—R¹⁷.

12. A compound of claim 1, wherein R¹⁶ is selected from $C_1$-$C_6$-alkyl and $C_1$-$C_4$-alkylene-$R^{16a}$.

13. A compound of claim 1, wherein R¹⁵ is H.

14. A compound of claim 1, wherein R² and R³ are each H.

15. A compound of claim 1, wherein R⁴ has the structure:

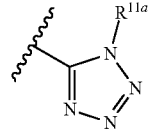

wherein $R^{11a}$ is selected from $C_1$-$C_4$-alkyl, $C_3$-$C_4$-alkenyl, $C_3$-$C_4$-alkynyl, phenyl, $C_3$-$C_6$-cycloalkyl, 3- to 6-membered heterocycloalkyl, 5- or 6-membered heteroaryl and $C_1$-$C_4$-haloalkyl.

16. A compound of claim 15, wherein $R^{11a}$ is $C_1$-$C_4$-alkyl.

17. A compound of claim 1, wherein

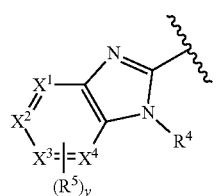

has the structure
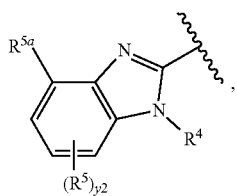
wherein R[5a] is selected from halo, cyano, nitro, $C_1$-$C_4$-alkyl and $C_1$-$C_4$-haloalkyl, O—$C_1$-$C_4$-alkyl and O—$C_1$-$C_4$-haloalkyl; and y2 is an integer independently selected from 0, 1, 2 and 3.
18. A compound of claim 1, wherein y is 0.
19. A compound of claim 1, wherein the compound of formula (I) is a compound selected from:
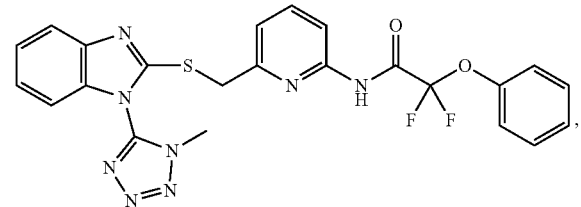
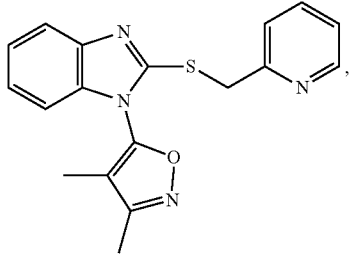
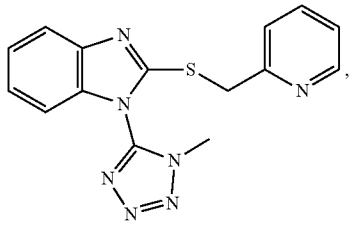
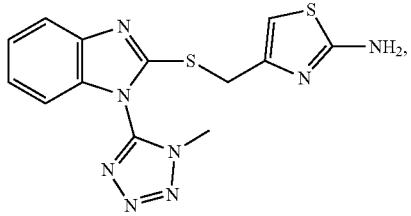
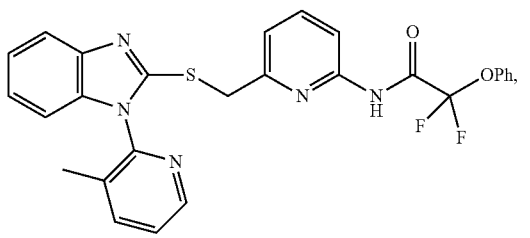
-continued
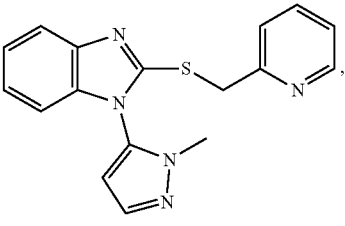
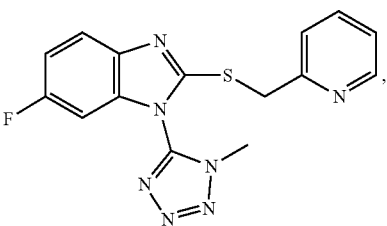
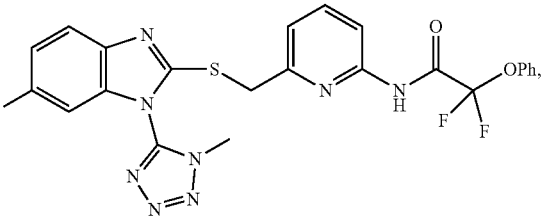
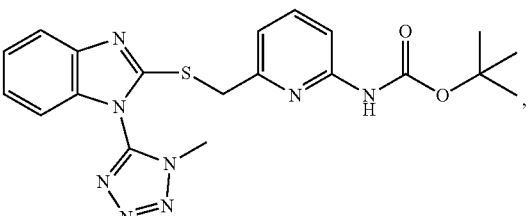
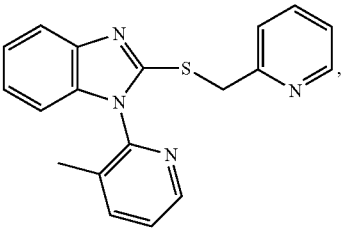
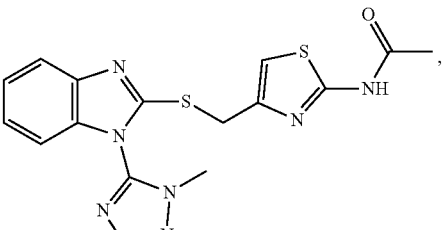
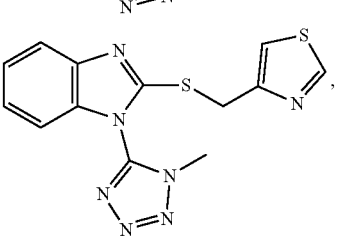

-continued
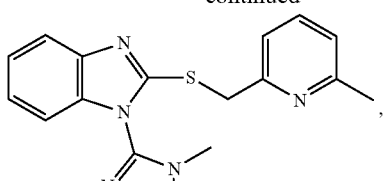
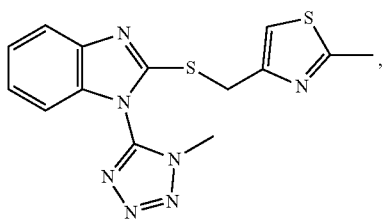
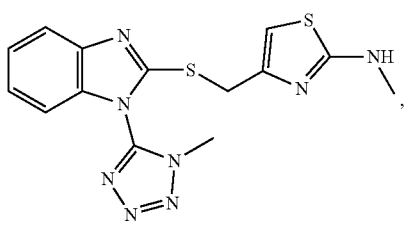
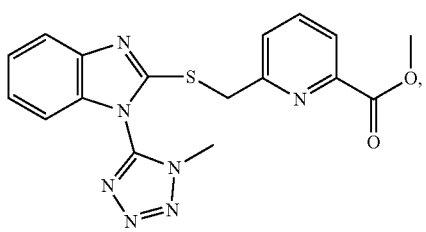
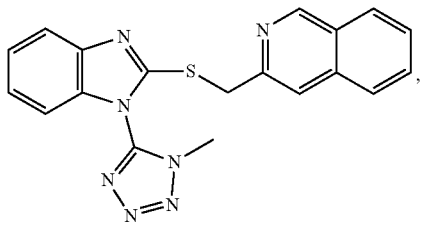
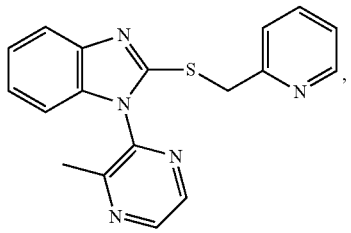
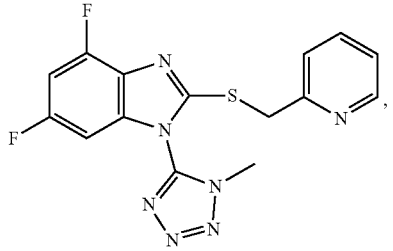
-continued
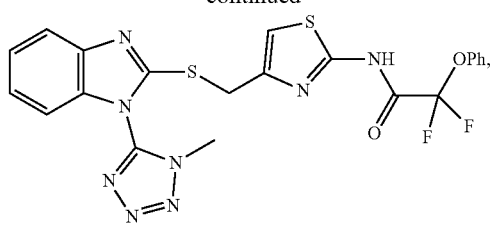
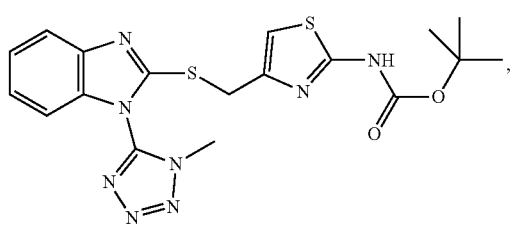
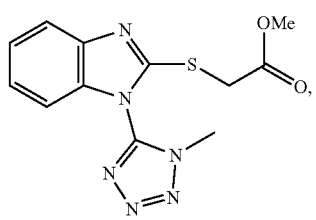
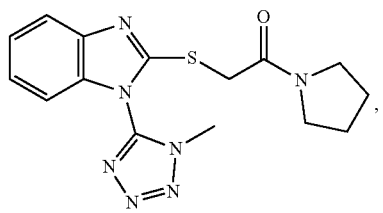
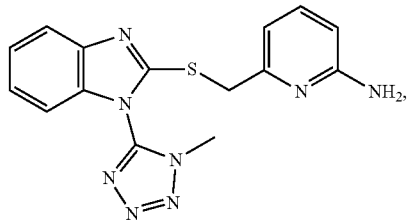
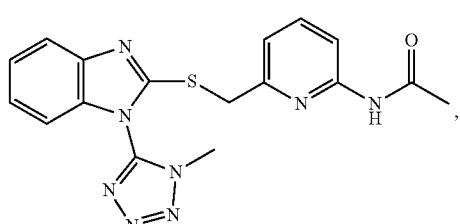
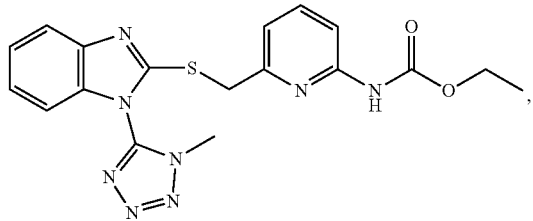

123
-continued
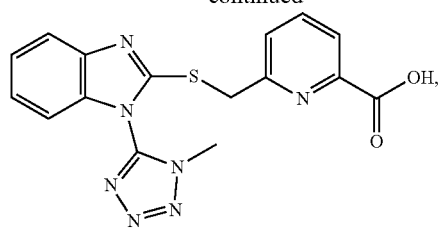
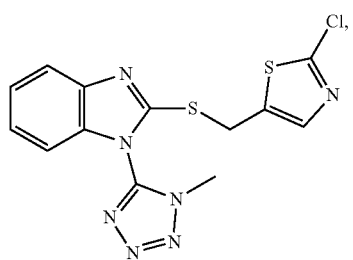
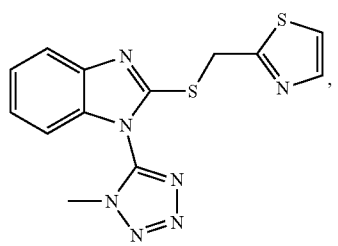
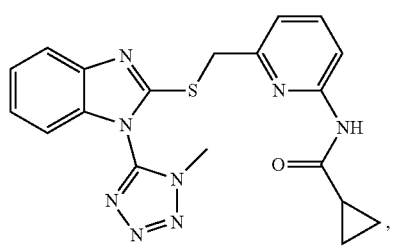
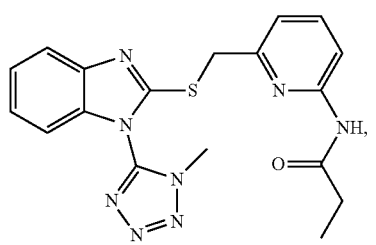
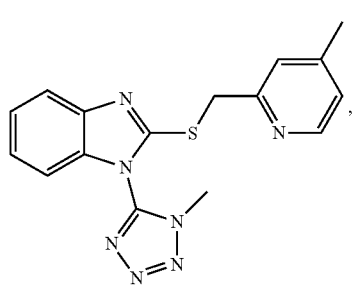
124
-continued
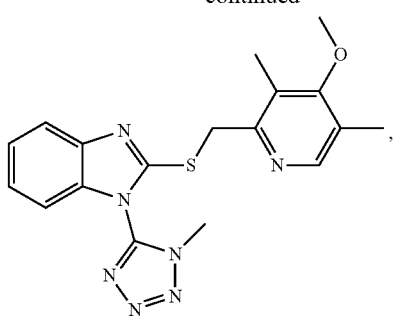
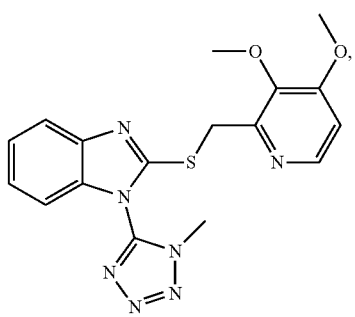
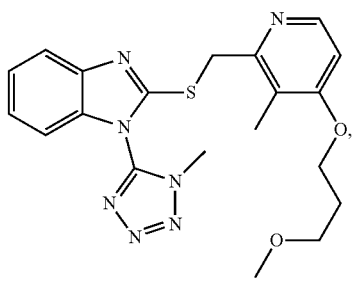
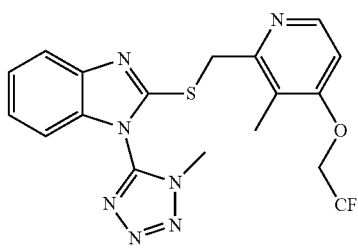
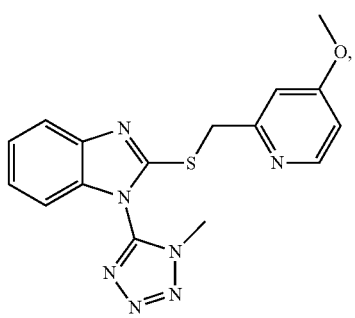
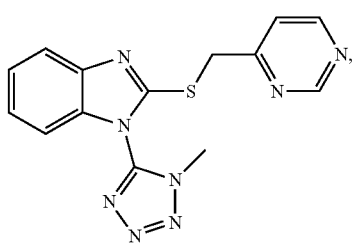

125
-continued
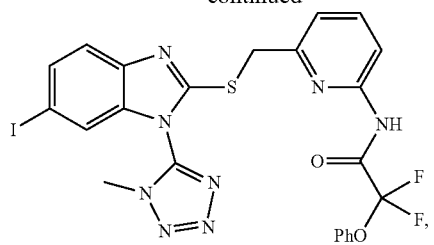
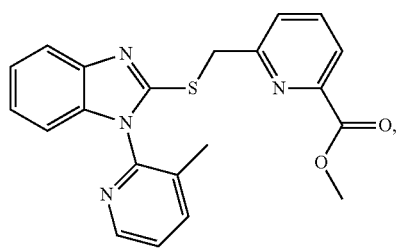
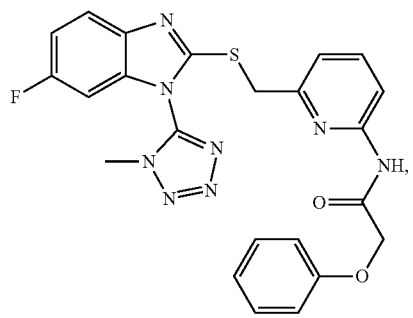
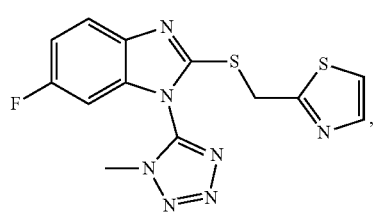
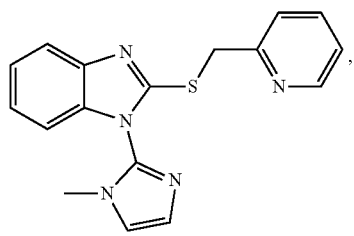
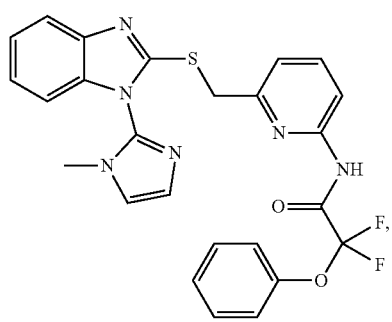
126
-continued
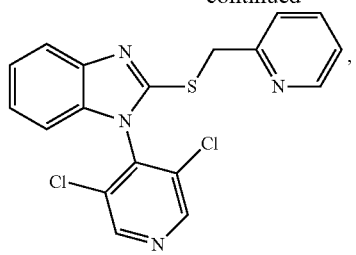
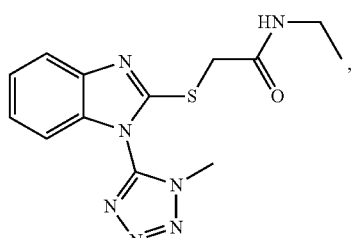
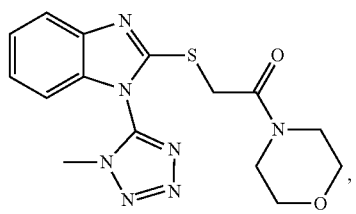
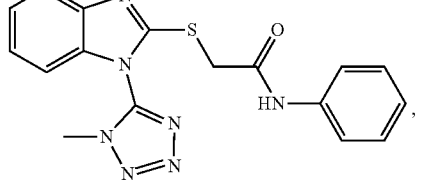

127
-continued
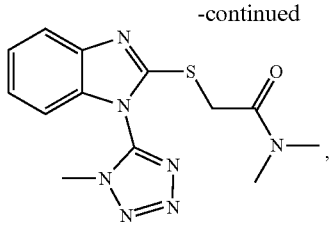
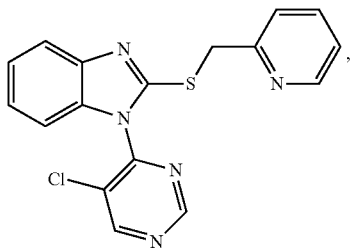
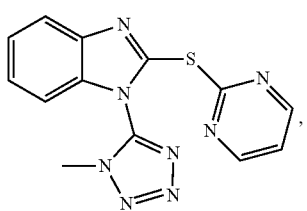
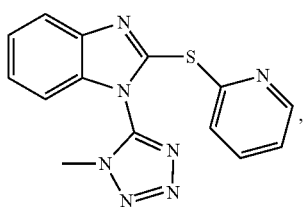
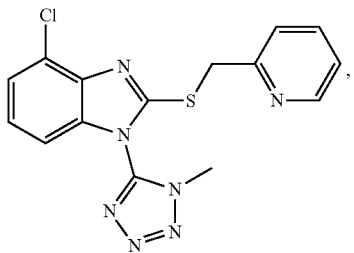
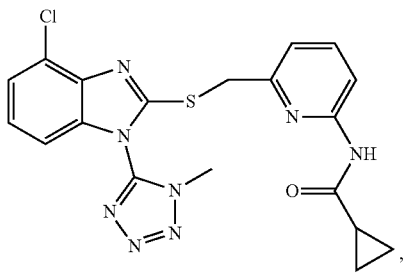
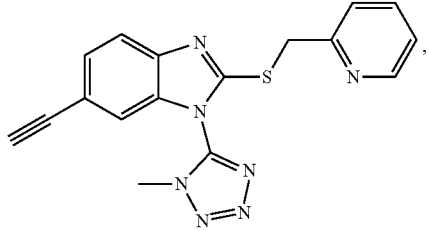
128
-continued
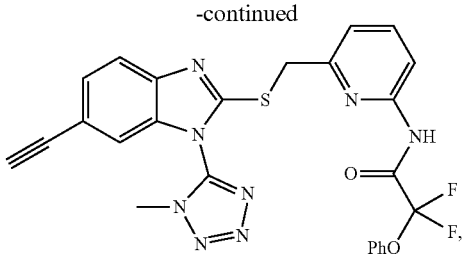
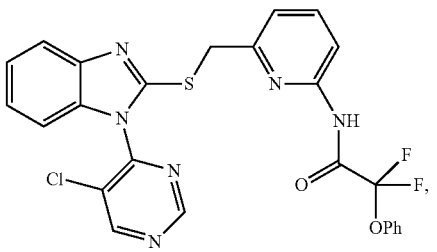
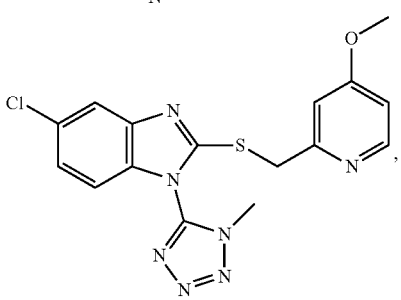
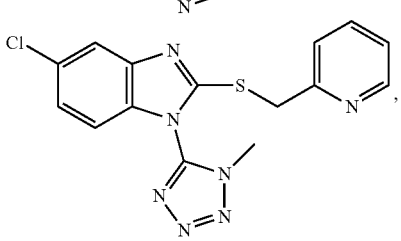
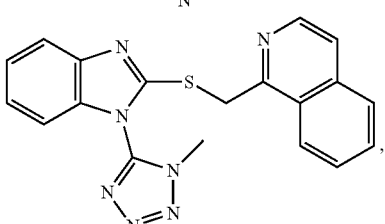
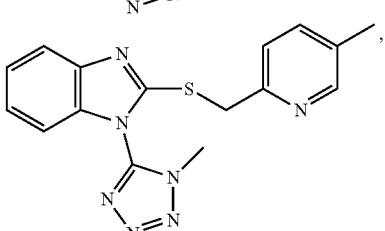
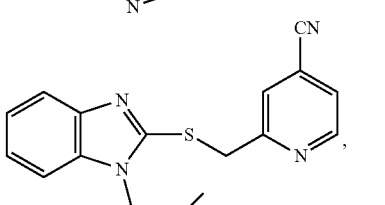
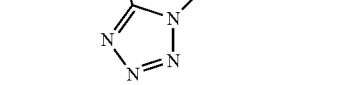

129
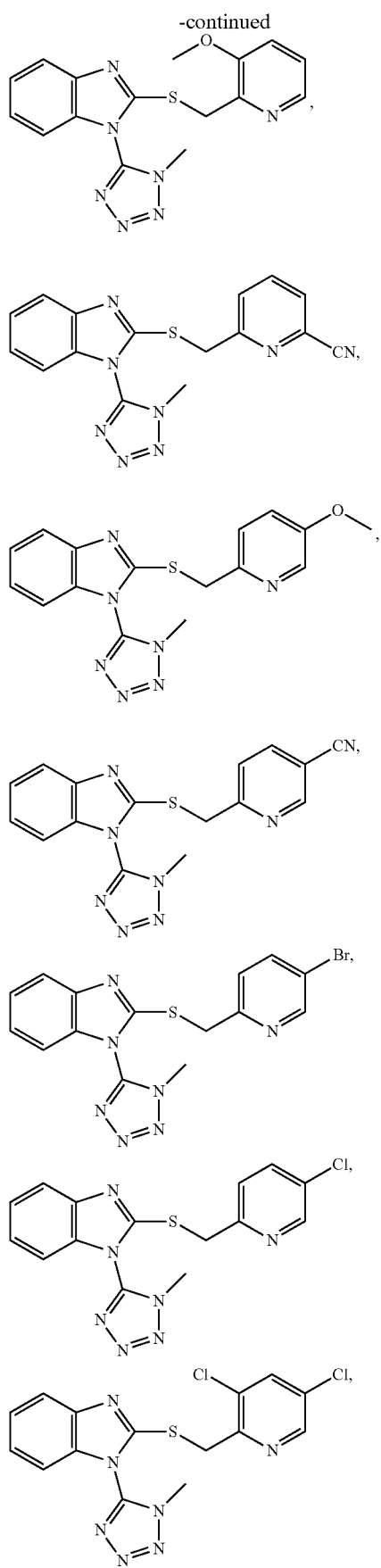
130
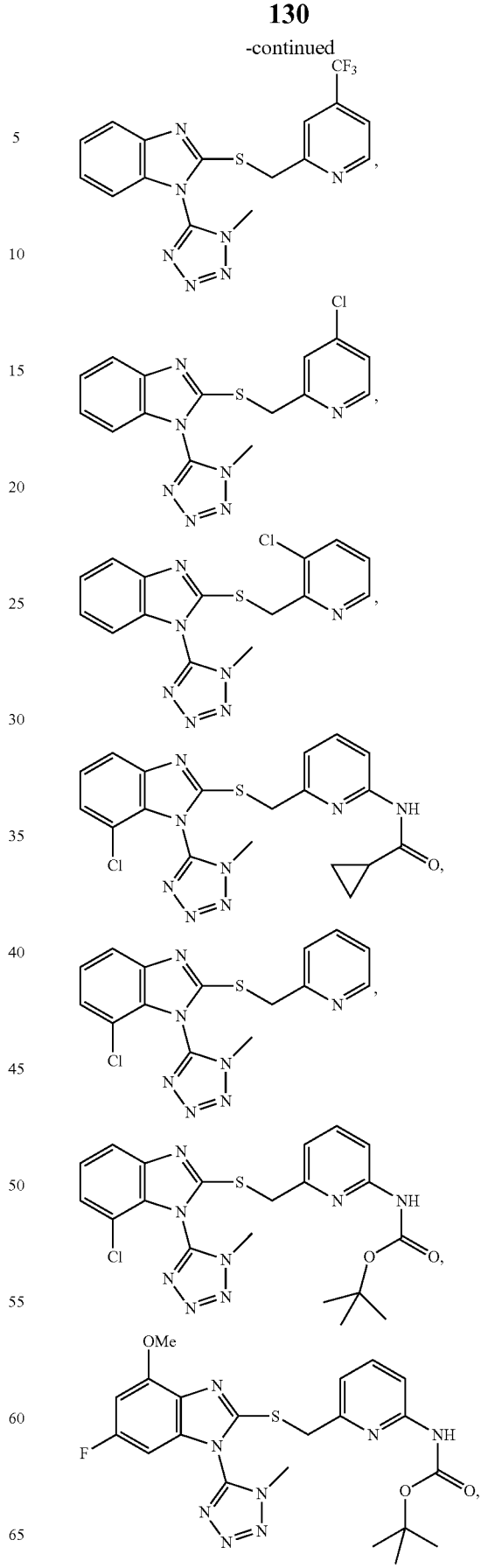

-continued

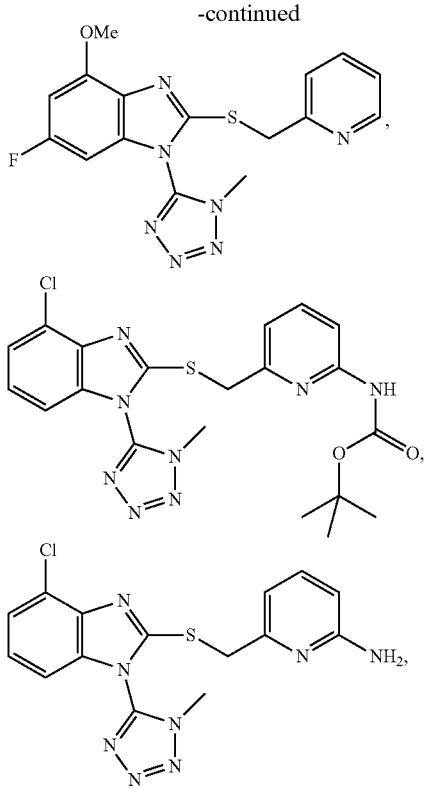

-continued

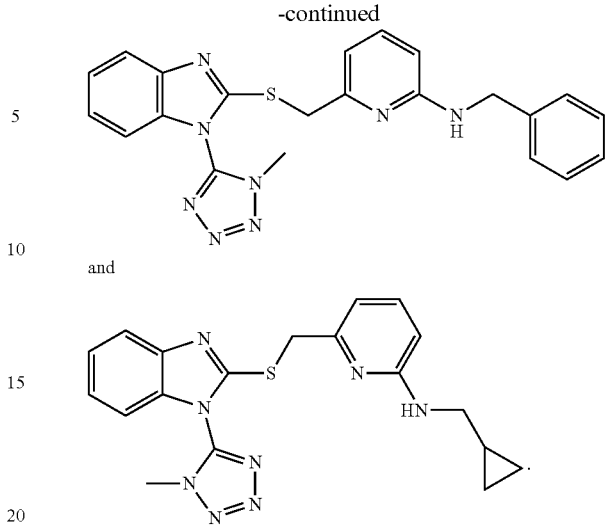

and

20. A fungicidal composition comprising an effective and non-phytotoxic amount of an active compound of claim 1.

21. A method for controlling fungal diseases, the method comprising applying an agronomically effective and substantially non-phytotoxic quantity of a compound of claim 1 to seeds of plants, to plants themselves or to an area where it is intended that plants will grow.

* * * * *